(12) United States Patent
Lone et al.

(10) Patent No.: US 7,663,017 B2
(45) Date of Patent: Feb. 16, 2010

(54) TRANSGENIC MICE HAVING A HUMAN MAJOR HISTOCOMPATABILITY COMPLEX (MHC) PHENOTYPE, EXPERIMENTAL USES AND APPLICATIONS

(75) Inventors: Yu-Chun Lone, Paris (FR); Anthony Pajot, Paris (FR); Claude Auriault, Nomoin (FR); Veronique Pancre, Orchies (FR); François Lemonnier, Bourg la Reine (FR)

(73) Assignee: Institut Pasteur, Paris (FR)

( * ) Notice: Subject to any disclaimer, the term of this patent is extended or adjusted under 35 U.S.C. 154(b) by 154 days.

(21) Appl. No.: 10/882,241

(22) Filed: Jul. 2, 2004

(65) Prior Publication Data

US 2005/0114910 A1    May 26, 2005

Related U.S. Application Data

(60) Provisional application No. 60/490,945, filed on Jul. 30, 2003.

(51) Int. Cl.
| | |
|---|---|
| *A01K 67/00* | (2006.01) |
| *A01K 67/033* | (2006.01) |
| *A01K 67/027* | (2006.01) |
| *C12N 15/00* | (2006.01) |
| *C12N 5/00* | (2006.01) |
| *C12N 5/10* | (2006.01) |
| *C12N 15/63* | (2006.01) |

(52) U.S. Cl. .............. 800/8; 800/3; 800/18; 800/21; 435/325; 435/354; 435/455

(58) Field of Classification Search .............. None
See application file for complete search history.

(56) References Cited

U.S. PATENT DOCUMENTS

2003/0101465 A1    5/2003 Lawman et al.

FOREIGN PATENT DOCUMENTS

| WO | WO 02/059263 A2 | 8/2002 |
| WO | WO 03/006639 A1 | 1/2003 |
| WO | WO 2005/004592 A2 | 1/2005 |

OTHER PUBLICATIONS

Rulicke and Hubischer, 2000, Experimental Physiology 85: 589-601.*
Holschneider et al., 2001, Int J. Devl. Neuroscience 18:615-618.*

(Continued)

*Primary Examiner*—Robert M. Kelly
*Assistant Examiner*—Kelaginamane Hiriyanna
(74) *Attorney, Agent, or Firm*—Finnegan, Henderson, Farabow, Garrett & Dunner, L.L.P.

(57) ABSTRACT

The present invention relates to transgenic mice and isolated transgenic mouse cells, the mice and mouse cells comprising a disrupted H2 class I gene, a disrupted H2 class II gene, a functional HLA class I transgene, and a functional HLA class II transgene. In embodiments, the transgenic mouse or mouse cells are deficient for both H2 class I and class II molecules, wherein the transgenic mouse comprises a functional HLA class I transgene and a functional HLA class II transgene. In embodiments, the transgenic mouse or mouse cell has the genotype HLA-A2$^+$HLA-DR1$^+$β2m°IAβ°. The invention also relates to methods of using a transgenic mouse of the invention.

4 Claims, 11 Drawing Sheets

OTHER PUBLICATIONS

Loirat et al (2000, J. immunology 165:4748-4755.*

Alexander, Jeff, et al., "Derivation of HLA-A11/K$^b$ Transgenic Mice," *Journal of Immunology*, vol. 159, No. 10, pp. 4753-4761 (1997).

Baker, Alexander G.H., et al., "Analogues of CTL Epitopes MHC Class-I Binding Capacity Elicit Anti-Melanoma CTL Recognizing the Wild-Type Epitope," *Journal of Cancer*, vol. 70, pp. 302-309 (1997).

Barra, Claude, et al., "Abrogation of H-2-Restricted CTL Responses and Efficient Recognition of HLA-A3 Molecules in DBA/2 HLA/A24 Responder Mice," *Journal of Immunology*, vol. 150, No. 9, pp. 3681-3689, (1993).

Benmohamed, Lbachir, et al., "Induction of CTL Response by a Minimal Epitope Vaccine in HLA A*0201/DR1 Transgenic Mice: Dependence on HLA Class II Restricted $T_H$ Response," *Human Immunology*, vol. 61, No. 8, pp. 764-779 (2000).

Carmon, Lior, et al., "Novel Breast-Tumor-Associated MUC1 Peptides: Characterization in D$^b$ -/- x β Microglobulin (β2m) Null Mice Transgenic for a Chimeric HLA-A2.1/D$^b$-β2 Microglobulin Single Chain," *International Journal of Cancer*, vol. 85, pp. 391-397 (2000).

Elliott, Suzanne L., et al., "Peptide based cytotoxic T-cell vaccines; delivery of multiple epitopes, help, memory and problems," *Vaccine*, vol. 17, pp. 2009-2019 (1999).

Epstein, Helen, et al., "Expression and Function of HLA-A2.1 in Transgenic Mice," *European Journal of Immunology*, vol. 7, pp. 1575-1583 (1989).

Hill, Adrian V.A., "The Immunogenetics of Human Infectious Diseases," *Annual Review of Immunology*, vol. 16, pp. 593-616 (1998).

Le, Al-Xuan T., "Cytotoxic T Cell Responses in HLA-A2.1 Transgenic Mice," *J. of Immunology*, vol. 142, No. 4, pp. 1366-1371 (1989).

Lustgarten, Joseph et al., "Identification of Her-2/Neu CTL Epitopes Using Double Transgenic Mice Expressing HLA-A-2.1 and Human CD.8," *Human Immunology*, vol. 52, No. 2, pp. 109-118 (1997).

Madson, Lars et al., "Mice lacking all conventional MHC class II genes," *Proceedings of the National Academy of Sciences*, vol. 96, pp. 10338-10343 (1999).

Nishimura, Yasuharu et al., "Expression of the Human MHC, HLA-DQW6 Genes Alters the Immune Response in C57BL/6 Mice," *Journal of Immunology*, vol. 145, No. 1, pp. 353-360 (1990).

Pajot, Anthony et al., "A mouse model of human adaptive immune functions: HLA-A2.1-/HLA-DR1-transgenic H-2 class I-/class II-knockout mice," *European Journal of Immunology*, vol. 34, No. 11, pp. 3060-3069 (2004).

Pajot, Anthony et al., "Comparison of HLA-DRI transgenic mice deficient for murine MHC class II and HLA-DRI transgenic mice expressing endogenous murine MHC class II molecules," *International Immunology*, vol. 16, No. 19, pp. 1275-1282 (2004).

Pascolo, Steve, et al., "HLA-A2.1-restricted Education and Cytolytic Activity of CD8* T.Lymphocytes from β2m) HLA-A2.1 Monochain Transgenic H-2D$^b$ β2m Double Knockout Mice.," *Journal of Experimental Medicine*, vol. 185, No. 12, pp. 2043-2051 (1997).

Steinmetz, Michael et al: "Recent experiments with MHC knock-out mice: More questions than answers," *BioEssays*, vol. 15, No. 9, pp. 613-615 (1993).

Vitiello, Antonella et al., "Development of a Lipopeptide-based Therapeutic Vaccine to Treat Chronic HBC Infection," *Journal of Clinical Investigation*, vol. 95, pp. 341-449 (1995).

Vitiello, Antonella et al., "Analysis of the HLA-restricted Influenza-specific Cytotoxic T Lymphocyte Response in Transgenic Mice Carrying a Chimeric Human-Mouse Class I Major Histocompatability Complex.," *Journal of Experimental Medicine*, vol. 173, No. 4, pp. 1007-1015 (1991).

Wentworth, Peggy A., et al., "Differences and similarities in the A2-1 restricted cytotoxic T Cell repertoire in humans and human leukocyte antigen-transgenic mice," *European Journal of Immunology*, vol. 29, No. 1 pp. 97-100 (1996).

U.S. Appl. No. 10/566,386, filed Jan. 30, 2006, as the national stage of PCT/IB2004/002374, filed on Jul. 5, 2004 (which published as WO 2005/004592 A2 on Jan. 20, 2005).

* cited by examiner

HLA-A2+DR1+CI-CII- T CD4 Proliferative Response to HLA-DR1 Restricted Epitopes
Following Immunization With PCMV S2-S

FIG 6

TRANSGENIC MICE HAVING A HUMAN MAJOR HISTOCOMPATABILITY COMPLEX (MHC) PHENOTYPE, EXPERIMENTAL USES AND APPLICATIONS

CROSS-REFERENCE TO RELATED APPLICATION

This application is based on and claims the benefit of U.S. Provisional Application No. 60/490,945, filed Jul. 30, 2003, the entire disclosure of which is relied upon and incorporated by reference herein for all purposes.

BACKGROUND OF THE INVENTION

Many vaccines are currently being developed for human cancer immunotherapy and for treatment of infectious diseases, such as malaria, AIDS, hepatitis C virus, and SARS. Given the rapidity with which new emerging pathogens can appear, it is important to improve animal models that could be used to evaluate vaccination strategies and the protective capacity of different epitopes quickly and reliably. Furthermore, in vivo studies are already required to assess crucial variables of vaccine behavior that are not easily evaluated or impossible to measure in vitro, such as vaccine immunogenicity, vaccine formulation, route of administration, tissue distribution, and involvement of primary and secondary lymphoid organs. Because of their simplicity and flexibility, small animals, such as mice represent an attractive alternative to more cumbersome and expensive model systems, such as nonhuman primates, at least for initial vaccine development studies.

The moderate efficacy observed in several clinical trials of vaccines, which were found to be protective in wild-type animal studies (McMichael, A. J. & Hanke, T. *Nat Med* 9, 874-880 (2003)), may be partly explained by the different influence that human and animal MHC have on the outcome of the immune response, since animal MHC and human HLA molecules do not present the same optimal epitopes (Rotzschke, O. et al. *Nature* 348, 252-254 (1990)). Thus, despite some limitations, transgenic mice expressing human HLA should represent a useful improvement over wild-type mice as a preclinical model for testing vaccine candidates, evaluating the potential risk that the vaccines could induce autoimmune disorders, and devising better therapeutic strategies based on the human restriction element.

Cytotoxic T Cells

Cytotoxic T cells (CTL) play a crucial role in the eradication of infectious diseases and in some cases, cancer (P. Aichele, H. Hengartner, R. M. Zinkernagel and M. Schulz, J Exp Med 171 (1990), p.1815; L. BenMohamed, H. Gras-Masse, A. Tartar, P. Daubersies, K Brahimi, M. Bossus, A. Thomas and P. Druhile, Eur J Immunol 27 (1997), p. 1242; D. J. Diamond, J. York, J. Sun, C. L. Wright and S. J. Forman, Blood 90 (1997), p. 1751). Recombinant protein vaccines do not reliably induce CTL responses (Habeshaw J A, Dalgleish A G, Bountiff L, Newell A L, Wilks, D, Walker L C, Manca F. 1990 November; 11 (11): 418-25; Miller S B, Tse H, Rosenspire A J, King S R. Virology. 1992 December; 191 (2):973-7). The use of otherwise immunogenic vaccines consisting of attenuated pathogens in humans is hampered, in several important diseases, by overriding safety concerns. In the last few years, epitope-based approaches have been proposed as a possible strategy to develop novel prophylactic and immunotherapeutic vaccines (Melief C J, Offringa R, Toes R E, Kast W M. Curr Opin Immunol. 1996 October, 8(5):651-7; Chesnut R W, Design testing of peptide based cytotoxic T-cell mediated immunotherapeutic to treat infction disease, cancer, in Ppowell, M F, Newman, M J (eds.): Vaccine Design: The Subunit, Adjuvant Approach, Plenum Press, New-York 1995, 847). This approach offers several advantages, including selection of naturally processed epitopes, which forces the immune system to focus on highly conserved and immunodominant epitopes of a pathogen (R. G. van der Most, A. Sette, C. Oseroff, J. Alexander, K. Murali-Krishna, L. L. Lau, S, Southwood, J. Sidney, R. W. Chesnut, M. Matioubian and R. Ahmed, J Immunol 157 (1996), p. 5543) and induction of multiepitopic responses to prevent escape by mutation such observed in HIV, hepatitis B virus (HBV) and hepatitis C virus (HCV) infections. It also allows the elimination of suppressive T cell determinants, which might preferably elicit a TH2 response, in conditions where a TH1 responses is desirable, or vice-versa (Pfeiffer C, Murray J, Madri J, Bottomly K. Immunol Rev. 1991 October; 123:65-84; P Chaturvedi, Q Yu, S Southwood, A Sette, and B Singh Int Immunol 1996 8: 745-755). It finally provides the possibility to get rid of autoimmune T cell determinants in antigens, which might induce undesirable autoimmune diseases. Protective antiviral or anti-tumoral immunity using CTL epitope-peptides has been achieved in several experimental models (D. J. Diamond, J. York, J. Sun, C. L. Wright and S. J. Forman, Blood 90 1997, p.1751; J. E. J. Blaney, E. Nobusawa, M. A. Brehm, R. H. Bonneau, L. M. Mylin, T. M. Fu, Y. Kawaoka and S. S. Tevethia, J Virol 72 (1998), p. 9567).

CTL epitope definition based on the usage of human lymphocytes might be misleading due to environmental and genetic heterogeneity that lead to incomplete results, and due to technical difficulties in isolating CTL clones. HLA class I or class II transgenic mice described to date have proved to be a valuable tool to overcome these limitations as illustrated by the identification with such animal models of novel CTL and T helper epitopes (Hill A V. Annu Rev Immunol. 1998;16: 593-617; Carmon L, El-Shami K M, Paz A., Pascolo S, Tzehoval E, Tirosb B, Koren R, Feldman M, Fridkin M, Lemonnier F A, Eisenbach L. Int J Cancer, Feb. 1, 2000; 85(3):391-7). These mice have also been used to demonstrate: i) good correlation between peptide HLA binding affinity and immunogenicity (Lustgarten J, Theobald M, Labadie C, LaFace D, Peterson P, Disis M L, Cheaver M A, Sherman L A. Hum Immunol. 1997 February; 52(2):109-18; Bakker A B, van der Burg S H, Huijbens R J, DRijfhout J W, Melief C J, Adema G J, Figdor C G. Int J Cancer. Jan. 27, 1997; 70(3):302-9), ii) significant overlap between the murine and human CTL system at the level of antigen processing (same epitopes generated), and iii) comparable mobilization against most antigens of the CTL repertoires in HLA transgenic mice and humans (Wentworth, P. A., A. Vifiello, J. Sidney, E. Keogh, P, W. Chesnut, H. Grey, A. Sette. 1996. Eur. J. Immunol. 26:97; Alexander, J., C. Oserof, J. Sidney, P. Wentworth, E. Keogh, G. Hermanson, F. V. Chisari R. T, Kubo, H. M, Grey, A, Sette, 1997. J. Immunol. 159:4753).

To date, synthetic peptide-based CTL epitope vaccines have been developed as immunotherapeutics against a number of human diseases [18-20]. However, only moderate efficacy was observed in several clinical trials (21). This may be partly explained by the failure of these vaccines to induce sufficiently strong CTL responses. Indeed, recent reports suggest the need for CD4+ T-cell help to obtain maximum CTL response (A. J. Zajac, K. Murali-Krishna, J. N. Blattman and R. Ahmed, Curr Opin Immunol 10 (1998), p. 444; Firat H, Garcia-Pons F, Tourdot S, Pascolo S, Scardino A, Garcia. Z, Michel M L, Jack R W, Jung O, Kosmatopoulos K, Mateo L, Suhrbier A, Lemonnier F A, Langlade-Dernoyen P Eur J Immunol 29, 3112,1999).

CTL are critical components of protective immunity against viral infections, but the requirements for in vivo priming of CTL are not completely understood. It is now accepted that Th cells are usually essential for CTL priming with synthetic peptides. With respect to synthetic CTL epitopic peptides, several studies point to a mandatory need for Th lymphocyte stimulation to induce optimal CTL responses (C. Fayolle, E. Deriaud and C. Leclerc, J Immunol 147 (1991), p, 4069; C. Widmann, P. Romero, J. L. Maryanski, G. Corradin and D. Valmori, J Immunol Meth 155 (1992), p. 95; M. Shirai, C. D. Pendkton, J. Ahlers, T. Takeshita, M. Newman and J. A. Berzofsky, J Immunol 152 (1994), p. 549; J. P. Sauet, H. Gras-Masse, J. G. Guillet and E. Gomard, Int Immunol 8 (1996). p. 457). Several of these studies showed that activation of a CD8+ T cell requires simultaneous interaction of a CD4+ T helper cell and a CD8+ T cell with the same antigen-presenting cell presenting their cognate epitopes (Ridge J P, Di Rosa F, Matzinger P. Nature. Jun. 4, 1998; 3 93 (6684): 474-8). The relevance of this three-cell interaction for priming of CTLs is confirmed by studies with viral epitopes, and animal models, since in vivo induction of CTLs was most efficient when CTL and Th epitopes were physically linked rather than administered as an unlinked mixture (Shirai M, Pendleton C D, Ahlers J, Takeshita T, Newman M, Berzohky J A. J Immunol. Jan. 15, 1994; 152(2): 549-56; Oseroff C, Sette A, Wentworth P, Celis E, Maewal A, Dahlberg C, Fikes J, Kubo R T, Chesnut R W, Grey B X Alexander J. Vaccine. 1998 May; 16(8): 823-33). The capacity of CTL and Th antigenic peptides to efficiently induce CTL responses has been demonstrated both in experimental models (C. Fayolle, E. Deriaud and C. Leclerc, J Immunol 147 (1991), p, 4069; C. Widmann, P. Romero, J. L. Maryanski, G. Corradin and D. Valmori, J Immunol Meth 155 (1992), p. 95) and in humans (A. Vitiello, G. Ishioka, H. M. Grey, R. Rose, P. Farness, R. LaFond, L. Yuan, F. V. Chisari, J. Furze and R. Bartholomeuz, J Clin Invest 95 (1995), p. 341; B. Livingston, C. Crimi, H. Grey, G. Ishioka, F. V. Chisari, J. Fikes, H. M. Grey, R. Chesnut and A. Sette, J Immunol 159 (1997), p.1383). Moreover, a potent Th response plays an important role not only for optimal induction of CTL responses, but also for maintenance of CTL memory (E. A. Walter, P. D. Greenberg, M. J. Gilbert, R. J. Finch, K-S. Watanabe, E. D. Tbomas and S. R. Riddell, N Engl J Med 333 (1995), p.1038; Riddell S R, Greenberg P D, In Thomas E D, Blume K G, Forman S J (eds): Hematopoietic Cell Transplantation, 2nd edn. Maiden, MA: Blackwell Science Inc., 1999). Finally, it has long been documented that CD4+ T "helper" cells are crucial in coordinating cellular and humoral immune responses against exogenous antigens.

Recently, a transgenic (Tg) mouse that expresses both HLA-A*0201 class I and HLA-DR1 class II molecules was established (BenMohamed L, Krishnan R, Longmate J, Auge C, Low L, Primus J, Diamond D J, Hum, Immunol. 2000 August;61 (8):764-79). The authors reported that both HLA-A*0201 and HLA-DR1 transgenes are functional in vivo, that both MHC class I and class II molecules were utilized as restriction elements, and that the product of the HLA-DR1 transgene enhances the HLA-A*0201-restricted antigen-specific CTL responses (BenMohamed L, Krishnan R, Longmate J, Auge C, Low L, Primus J, Diamond D J, Hum, Immunol. 2000 August;61 (8):764-79).

It is noteworthy that these HLA-A*0201/DR1 Tg mice expressed their own MHC H-2 class I and class II molecules. Because HLA class I transgenic mice expressing endogenous mouse MHC class I genes preferentially and often exclusively develop H-2 restricted CTL response (C Barra, H Gournier, Z Garcia, P N Marche, E Jouvin-Marche, P Briand, P Fillipi, and F A Lemonnier J Immunol 1993 150: 3681-3689; Epstein H, Hardy F., May J S, Johnson M H, Holmes N. Eur J Immunol. 1989 September;19(9):1575-83; Le A X; E J Bernhard, M J Holterman, S Strub, P Parham, E Lacy, and V H Engelhard J Immunol 1989 142: 13 66-1371; Vitiello A, Marchesini D, Furze J, Sherman L A, Chesnut R W., J Exp Med. Apr. 1, 1991;173(4):100715), and HLA class II transgenic mice expressing endogenous mouse MHC class II genes fail to induce reliable HLA class II restricted antigen-specific responses (Nishimura Y, Iwanaga T, Inamitsu T, Yanagawa Y, Yasunami M, Kimura A, Hirokawa K, Sasazuki T., J Immunol Jul. 1, 1990;145(1):353-60), these HLA-A*0201/DR1 Tg mice are of limited utility to assess human-specific responses to antigen.

However, in HLA class I transgenic H-2 class I knock-out mice, or HLA class II transgenic H-2 class II knock-out mice, only HLA-restricted CTL immune responses occur (Pascolo S, Bervas N, Ure J M, Smith A G, Lemonnier F A, Perarnau, B., J Exp Med. Jun. 16, 1997;185(12).2043-51; Madsen L, Labrecque N, Engberg J, Dierich A, Svejgaard A, Benoist C, Mathis D, Fugger L. Proc Natl Acad Sci USA—Aug. 31, 1999;96(18):10338-43). In fact, HLA-A2.1-transgenic H-2 class I-knock-out (KO) mice exhibit the ability to mount enhanced HLA-A2.1-restricted responses as compared to HLA-A2.1-transgenic mice that still express the endogenous murine H-2 class I molecules (Pascolo, S. et al. *J Exp Med* 185, 2043-2051 (1997); Ureta-Vidal, A., Firat, H., Perarnau, B. & Lemonnier, F. A. *J Immunol* 163, 2555-2560 (1999); Firat, H. et al., *Int Immunol* 14, 925-934 (2002); Rohrlich, P. S. et al., *Int Immunol* 15, 765-772 (2003)). The inventors have made similar observations with HLA-DR1-transgenic mice, depending on whether or not they are deficient in H-2 class II molecules (A. Pajot, unpublished results). Furthermore, in the absence of competition from murine MHC molecules, the HLA-A2.1-transgenic H-2 class I-KO or HLA-DRI-transgenic H-2 class II-KO mice generate only HLA-restricted immune responses (Pascolo, S. et al. *J Exp Med* 185, 2043-2051 (1997)) (A. Pajot, unpublished results), facilitating the monitoring of HLA-restricted $CD8^+$ and $CD4^+$ T cell responses. However, protective immune responses against pathogens, which often require collaboration between T helper and cytotoxic $CD8^+$ T cells, cannot be studied in the single HLA class I- or HLA class II-transgenic mice, which do not allow the simultaneous assessment of HLA class I and II human responses in the same mouse.

Accordingly, there exists a need in the art for a convenient animal model system to test the immunogenicity of human vaccine candidates comprising constructs containing human CTL epitopes and, in some cases, with the inclusion of high potency CD4+ Th (helper T lymphocyte) epitopes to sustain antiviral and antitumoral CD8+ T-cell activity (A. J. Zajac, K. Murali-Krishna, J. N. Blattman and R. Ahmed, Curr Opin Immunol 10 (1998), p. 444; Firat H, Garcia-Pons F, Tourdot S, Pascolo S, Scardino A, Garcia Z, Michel M L, Jack R W, Jung O, Kosmatopoulos K, Mateo L, Suhrbier A, Lemonnier F A, Langlade-Dernoyen P, Eur J Immunol 29,3112, 1999). There is also a need for a system that allows the simultaneous assessment of the mutual coordination between a CTL response, a TH response (in particular s $TH_1$ or $TH_2$ response), and, optionally, a humoral response.

SUMMARY OF THE INVENTION

The inventors have met this need and more by providing mice transgenic for both HLA-A2.1 and HLA-DR1 molecules, in a background that is deficient for both H-2 class I and class II molecules. Specifically, the invention provides mice comprising (1) mutated H-2 class I and class II molecules; and (2) expressing HLA class I transgenic molecules, or HLA class II transgenic molecules, or HLA class I transgenic molecules and HLA class II transgenic molecules. These mice provide a model useful in the development and optimization of vaccine constructs with maximum in vivo immunogenicity for human use. Specifically, such mice enable a complete analysis of the three components of the immune adaptive response (antibody, helper and cytolytic) in a single animal, as well as an evaluation of the protection specifically conferred by vaccination against an antigenic challenge.

Mice of the invention, which comprise a knock-out for both H-2 class I and class II molecules, and express HLA class I transgenic molecules and HLA class II transgenic molecules represent a completely humanized experimental mouse that can be used to simultaneously detect the presence of antigen-specific antibodies, an antigen-specific HLA-DRI restricted T cell response, and an antigen-specific HLA-A2 restricted T cell response. These mice will be useful to study how mutual coordination operates between a CTL response, a TH response (in particular a $TH_1$ or $TH_2$ response), and, optionally, a humoral response. These mice represent an optimized tool for basic and applied vaccinology studies.

A first embodiment of the invention provides a transgenic mouse comprising a disrupted H2 class I gene, a disrupted H2 class II gene, and a functional HLA class I or class II transgene.

A second embodiment of the invention provides a transgenic mouse comprising a disrupted H2 class I gene, a disrupted H2 class II gene, a functional HLA class I transgene, and a functional HLA class II transgene.

In some embodiments, the HLA class I transgene is an HLA-A2 transgene and the HLA class II transgene is an HLA-DR1 transgene. In other embodiments, the HLA-A2 transgene comprises the HLA-A2 sequence provided in the sequence listing and the HLA-DR1 transgene comprises the HLA-DR1 sequence provided in the sequence listing.

A further embodiment of the invention provides a transgenic mouse deficient for both H2 class I and class II molecules, wherein the transgenic mouse comprises a functional HLA class I transgene and a functional HLA class II transgene. In an embodiment, the mouse has the genotype HLA-A2$^+$HLA-DR1$^+$β2m°IAβ°. In some embodiments the HLA-A2 transgene comprises the HLA-A2 sequence provided in the sequence listing and the HLA-DR1 transgene comprises the HLA-DR1 sequence provided in the sequence listing.

Another embodiment of the invention provides a method of simultaneously identifying the presence of one or more epitopes in a candidate antigen or group of antigens, where the one or more epitopes elicits a specific humoral response, a TH HLA-DR1 restricted response, and/or a CTRL HLA-A2 restricted response. The method comprises administering the candidate antigen or group of candidate antigens to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$HLA-DR1$^+$β2m°IAα°; assaying for a specific humoral response in the mouse to the antigen; assaying for a TH HLA-DR1 restricted response in the mouse to the antigen; and assaying for a CTRL HLA-A2 restricted response in the mouse to the antigen. Observation of a specific humoral response in the mouse to the antigen identifies an epitope that elicits a humoral response in the antigen. Observation of a TH HLA-DR1 restricted response in the mouse to the antigen identifies an epitope that elicits a TH HLA-DR1 restricted response in the antigen. Observation of a CTRL HLA-A2 restricted response in the mouse to the antigen identifies an epitope which elicits a CTRL HLA-A2 restricted response in the antigen.

In some embodiments, the method includes assaying for a Th1-specific response in the mouse to the antigen and assaying for a Th2-specific response in the mouse to the antigen. In this case, observation of a Th1-specific response in the mouse to the antigen identifies an epitope that elicits a Th1-specific response in the mouse to the antigen, and observation of a Th2-specific response in the mouse to the antigen identifies an epitope that elicits a Th2-specific response in the mouse to the antigen.

This invention also provides a method of identifying the presence of an HLA DR1-restricted T helper epitope in a candidate antigen or group of candidate antigens, the method comprising administering the candidate antigen or group of candidate antigens to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$HLA-DR1$^+$β2m°IAβ°; and assaying for a TH HLA-DR1 restricted T helper epitope response in the mouse to the antigen. Observation of a TH HLA-DR1 restricted T helper epitope response in the mouse to the antigen identifies an epitope that elicits a TH HLA-DR1 restricted T helper epitope response in the antigen.

In addition, this invention provides an isolated antigen comprising an HLA DR1-restricted T helper epitope identified by the method of the preceding paragraph. In some embodiments, the isolated antigen further includes an epitope that elicits a humoral response and/or an epitope that elicits a CTRL HLA-A2 restricted response. In some embodiments, the antigen comprising an HLA DR1-restricted T helper epitope comprises a polypeptide. In other embodiments, the antigen comprising an HLA DR1-restricted T helper epitope comprises a polynucleotide. In further embodiments, the antigen comprising an HLA DR1-restricted T helper epitope comprises DNA, RNA, or DNA and RNA.

Further, this invention provides a method of identifying the presence of an HLA-A2-restricted T cytotoxic (CTL) epitope in a candidate antigen or group of candidate antigens, the method comprising administering the candidate antigen or group of candidate antigens to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$HLA-DR1$^+$β2m°IAβ°; and assaying for an HLA-A2-restricted T cytotoxic (CTL) response in the mouse to the antigen or group of antigens. Observation of an HLA-A2-restricted T cytotoxic (CTL) response in the mouse to the antigen or group of antigens identifies an epitope that elicits a an HLA-A2-restricted T cytotoxic (CTL) response in the antigen or group of antigens.

This invention provides an isolated antigen comprising an HLA-A2-restricted T cytotoxic (CTL) epitope identified by the method of the preceding paragraph. In some embodiments, the antigen further comprises an epitope that elicits a humoral response and/or an epitope that elicits a TH HLA-DR1 restricted T helper epitope response. In some embodiments, the antigen comprising an HLA-A2-restricted T cytotoxic (CTL) epitope comprises a polypeptide. In other embodiments, the antigen comprising an HLA-A2-restricted T cytotoxic (CTL) epitope comprises a polynucleotide. In further embodiments, the antigen comprising an HLA-A2-restricted T cytotoxic (CTL) epitope comprises, DNA, RNA, or DNA and RNA.

This invention also provides a method of comparing the efficiency of the T-helper cell response induced by two or more vaccines. This method comprises administering a first candidate vaccine to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$HLA-DR1$^+$ β2m°IAβ°, and measuring the T-helper cell response induced in the mouse by the first candidate vaccine; administering a second candidate vaccine to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$ HLA-DR1$^+$β2m°IAβ°, and measuring the T-helper cell response induced in the mouse by the second candidate vaccine; administering each additional candidate vaccine to be compared to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$HLA-DR1$^+$ β2m°IAβ°, and measuring the T-helper cell response induced in the mouse by the additional candidate vaccine, and determining the efficiency of each candidate vaccine to induce a T-helper cell response by comparing the T-helper cell responses to each of the vaccines to be compared with each other. In some embodiments the T-helper cell response is an HLA-DR1 restricted response.

In addition, this invention provides a method of comparing the efficiency of T cytotoxic cell responses induced by two or more vaccines. The method includes administering a first candidate vaccine to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$HLA-DR1$^+$ β2m°IAβ°, and measuring the T cytotoxic cell response induced in the mouse by the first candidate vaccine; administering a second candidate vaccine to a mouse of a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$HLA-DR1$^+$β2m°IAβ°, and measuring the T cytotoxic cell response induced in the mouse by the second candidate vaccine; administering each additional candidate vaccine to be compared to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$ HLA-DR1$^+$β2m°IAβ°, and measuring the T cytotoxic cell response induced in the mouse by the additional candidate vaccine; and determining the efficiency of each candidate vaccine to induce a T cytotoxic cell response by comparing the T cytotoxic cell responses to each of the vaccines to be compared with each other. In some embodiments the T cytotoxic cell response is an HLA-A2 restricted response.

Further, this invention provides a method of simultaneously comparing the efficiency of T-helper cell response and T cytotoxic cell response induced by two or more vaccines. The method comprises administering a first candidate vaccine to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$HLA-DR1$^+$ β2m°IAβ°, and measuring the T-helper cell response and T cytotoxic cell response induced in the mouse by the first candidate vaccine; administering a second candidate vaccine to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$HLA-DR1$^+$β2m°IAβ°, and measuring the T-helper cell response and T cytotoxic cell response induced in the mouse by the second candidate vaccine; administering each additional candidate vaccine to be compared to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$HLA-DR1$^+$β2m°IAβ°, and measuring the T-helper cell response and T cytotoxic cell response induced in the mouse by each additional candidate vaccine; and determining the efficiency of each candidate vaccine to induce a T-helper cell response and T cytotoxic cell response by comparing the T-helper cell response and T cytotoxic cell response to each of the vaccines to be compared with each other. In some embodiments the T-helper cell response is an HLA-DR1 restricted response, and the T cytotoxic cell response is an HLA-A2 restricted response.

This invention also provides a method of simultaneously determining the humoral response, the T-helper cell response, and the T cytotoxic cell response of a mouse following its immunization with an antigen or a vaccine comprising one or more antigens. The method comprises administering the antigen or the vaccine comprising one or more antigens to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2+HLA-DR1+β2m°IAβ°, and assaying for a specific humoral response in the mouse to the antigen or vaccine comprising one or more antigens, assaying for a T-helper cell response in the mouse to the antigen or vaccine comprising one or more antigens, and assaying for a T cytotoxic cell response in the mouse to the antigen or vaccine comprising one or more antigens. In some embodiments the T-helper cell response is a TH HLA-DR1 restricted response. In some embodiments the T cytotoxic cell response is a CTRL HLA-A2 restricted response.

This invention also provides a method of optimizing two or more candidate vaccine compositions for administration to a human, based on preselected criteria. The method includes simultaneously determining the humoral response, the T-helper cell response, and the T cytotoxic cell response of a mouse following its immunization with the two or more candidate vaccine compositions, using a method comprising administering the antigen or the vaccine comprising one or more antigens to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2+HLA-DR1+ β2m°IAβ°, assaying for a specific humoral response in the mouse to the antigen or vaccine comprising one or more antigens, assaying for a T-helper cell response in the mouse to the antigen or vaccine comprising one or more antigens, assaying for a T cytotoxic cell response in the mouse to the antigen or vaccine comprising one or more antigens, and selecting an optimized vaccine by applying preselected criteria to the results. In some embodiments, the two or more vaccine candidates differ only in the ratio of antigen to adjuvant present in the vaccine. In some embodiments, the two or more vaccine candidates differ only in the type of adjuvant present in the vaccine.

In another aspect, the invention provides a method of determining whether a vaccine poses a risk of induction of an autoimmune disease when administered to a human. The method comprises administering the vaccine to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2+HLA-DR1+β2m°IAβ°, and assaying for an autoimmune response in the mouse, where observation of an autoimmune response in the mouse indicates that the vaccine poses a risk of induction of an autoimmune disease when administered to a human.

This invention also provides an isolated transgenic mouse cell comprising a disrupted H2 class I gene, a disrupted H2 class II gene, and a functional HLA class I or class II transgene.

In addition, the invention provides an isolated transgenic mouse cell comprising a disrupted H2 class I gene, a disrupted H2 class II gene, a functional HLA class I transgene, and a functional HLA class II transgene.

In some embodiments, the HLA class I transgene is an HLA-A2 transgene and the HLA class II transgene is an HLA-DR1 transgene. In other embodiments, the HLA-A2 transgene comprises the HLA-A2 sequence provided in the sequence listing and the HLA-DR1 transgene comprises the HLA-DR1 sequence provided in the sequence listing.

Further, this invention provides an isolated transgenic mouse cell deficient for both H2 class I and class II molecules, wherein the transgenic mouse cell comprises a functional HLA class I transgene and a functional HLA class II transgene. In some embodiments, the transgenic mouse cell has the genotype HLA-A2+HLA-DR1+β2m°IAβ°. In other embodiments, the HLA-A2 transgene comprises the HLA-A2 sequence provided in the sequence listing and the HLA-DR1 transgene comprises the HLA-DR1 sequence provided in the sequence listing.

BRIEF DESCRIPTION OF THE DRAWINGS

The invention will be more fully described with reference to the drawings in which:

FIG. 6 shows the T CD4 proliferative response to HLA-DR1 restricted epitopes following immunization of HLA-A2+DR1+CI–CII– mice with pcmv S2-S.

SEQUENCES

Figure 1A:
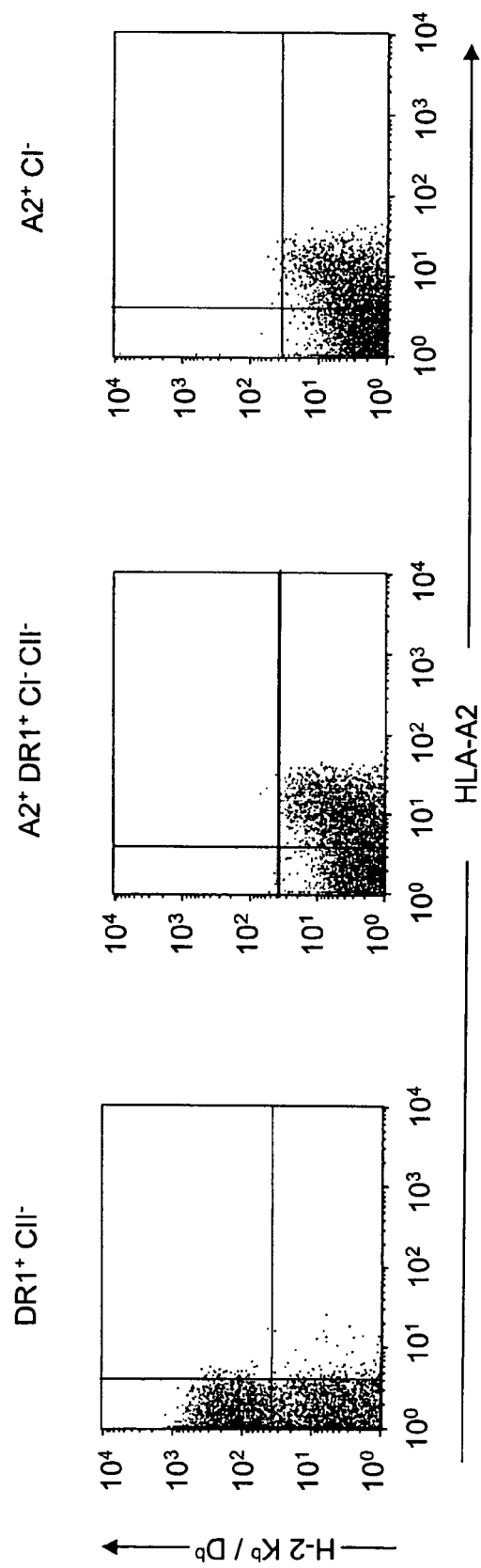
FIG. 1 shows a flow cytometric analysis of the cell-surface expression of the indicated transgenic molecules. (a) Splenocytes from HLA-DR1-transgenic H-2 class II-KO (DR1+ CII−, left panel), HLA-A2.1-/HLA-DR1-transgenic H-2 class I-/class II-KO (A2+ DR1+ CI− CII−, central panel), and HLA-A2.1-transgenic H-2 class I-KO (A2+ CI−, right panel) mice were stained with either FITC-labeled W6/32 (anti-HLA-ABC, in abcissas) or biotinylated 28-8-6S (anti-H-2$K^b$/$D^b$, in ordinates) m.Ab, the latter revealed with PE-labeled anti-mouse IgG. (b) B220+ splenic B lymphocytes from the same strains of mice, were stained with FITC-labeled L243 (anti-HLA-DR1, upper panels) and PE-labeled AF6-120.1 (anti-H-2 IA$\beta^b$, lower panels) m.Ab.

SEQ ID NO:1 contains the following subparts: Nucleotides 1-1205 comprise the HLA-A2 promoter; nucleotides 1206-1265 the HLA-A2 leader sequence; nucleotides 1266-1565 the human β2 microgobulin cDNA; nucleotides 1566-1610 a (Gly4Ser)$_3$ linker (SEQ ID NO:4); nucleotides 1611-2440 a segment containing exon 2 and part of intron 3 of HLA-A2; and nucleotides 2441-4547 a segment containing part of intron 3, exons 4 to 8, and part of the 3' non-coding region of the $H_2D^b$ gene.

SEQ ID NO:2 is the nucleotide sequence of the DRA*0101 gene. Nucleotides 1-15279 are the promoter located 5' to the HLA-DR alpha gene, nucleotides 15280-15425 are exon 1, nucleotides 15344-15346 are the ATG start codon, nucleotides 17838-18083 are exon 2, nucleotides 18575-18866 are exon 3, nucleotides 19146-19311 are exon 4, and nucleotides 20008-20340 are exon 5.

SEQ ID NO:3 is the nucleotide sequence of the DRB1*010101 gene. Nucleotides 7391-7552 are exon 1, nucleotides 7453-7455 are the ATG start codon, nucleotides 15809-16079 are exon 2, nucleotides 19536-19817 are exon 3, nucleotides 20515-20624 are exon 4, nucleotides 21097-21121 are exon 5, and nucleotides 21750-22085 are exon 6.

DETAILED DESCRIPTION OF THE INVENTION

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press:1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols.154 and 155 (Wu et al. eds.) and Vol.185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

This invention provides mice comprising (1) mutated H-2 class I and class II molecules; and (2) expressing HLA class I transgenic molecules, or HLA class II transgenic molecules, or HLA class I transgenic molecules and HLA class II transgenic molecules. Mice of the invention, which comprise a knock-out for both H-2 class I and class II molecules, and express HLA class I transgenic molecules and HLA class II transgenic molecules represent a completely humanized experimental mouse that can be used to simultaneously detect the presence of antigen-specific antibodies, an antigen-specific HLA-DRI restricted T cell response, and an antigen-specific HLA-A2 restricted T cell response. These mice are useful to study how mutual coordination operates between a CTL response, a TH response (in particular a $TH_1$ or $TH_2$ response), and, optionally, a humoral response. These mice represent an optimized tool for basic and applied vaccinology studies.

The invention provides transgenic mouse comprising a disrupted H2 class I gene, a disrupted H2 class II gene, and a functional HLA class I or class II transgene. In some embodiments, the transgenic mouse comprises a disrupted H2 class I gene, a disrupted H2 class II gene, a functional HLA class I transgene, and a functional HLA class II transgene. Such a mouse can be said to be a completely humanized experimental mouse, because it can be used to simultaneously detect the presence of antigen-specific antibodies, an antigen-specific HLA-DRI restricted T cell response, and an antigen-specific HLA-A2 restricted T cell response.

As shown, in part, in the Examples provided herein, and as is generally clear to one of skill in the art from the disclosure, HLA-A2.1-/HLA-DR1-transgenic H-2 class I-/class II-KO mice have the capacity to develop HBsAg-specific antibody, CD4$^+$ helper and CD8$^+$ cytolytic T cell responses following DNA immunization. These responses, observed in every single mouse tested, were directed at the same immunodominant epitopes as human responses and conferred to the immunized animals specific protection against a HBsAg recombinant vaccinia virus.

T helper cells are essential for full maturation of antibody responses (Katz, D. H. & Benacerraf, B., Adv Immunol 15, 1-94 (1972)) CTL priming against many epitopes (von Boehmer, H. & Haas, W., J Exp Med 150, 1134-1142 (1979); Keene, J. A. & Forman, J., J Exp Med 155, 768-782 (1982)) and CTL long-term maintenance (Matloubian, M., Concepcion, R. J. & Ahmed, R., J Virol 68, 8056-8063 (1994)). Both antibodies (Lefrancois, L., J Virol 51, 208-214 (1984)) and CTL (Zinkernagel, R. M. & Welsh, R. M., J Immunol 117, 1495-1502 (1976)) are critical components of protective immunity against viral infections. Potent HBsAg-specific antibody and CTL responses were in fact observed in HLA-A2.1-/HLA-DR1-double transgenic, H-2 class I-/class II-KO mice, but not in HLA-A2.1-single transgenic, H-2 class I-/ class II-KO mice. Thus, HBsAg-specific CD4+ T cell help is essential for generating efficient HBsAg-specific CTL and antibody responses. These results are consistent with studies on HBsAg-immunized mice (Milich, D. R., *Semin Liver Dis* 11, 93-112(1991)) and HBsAg-vaccinated humans (Celis, E., Kung, P. C. & Chang, T. W., *J Immunol* 132, 1511-1516 (1984)), which suggest that production of an anti-HBs antibody response is dependent on CD4+ T cells.

Transgenic mice expressing both HLA-A2.1 class I and HLA-DR1 class II molecules have already been derived (BenMohamed, L. et al. *Hum Immunol* 61, 764-779 (2000)). The authors reported that both the HLA-A2.I and HLA-DR1 molecules are functional restriction elements in vivo and that the product of the HLA-DR1 transgene enhances the HLA-A2.1-restricted antigen-specific CTL responses. However, the human relevance of the immune responses in these mice is dwarfed by the fact that they still expressed their own H-2 class I and class II molecules, which are usually preferentially and often exclusively used as restricting elements in response to antigens (Ureta-Vidal, A., Firat, H., Perarnau, B. & Lemonnier, F. A., *J Immunol* 163, 2555-2560 (1999); Rohrlich, P. S. et al., *Int Immunol* 15, 765-772 (2003)) (A. Pajot, unpublished results). The invention described herein overcomes this limitation by providing HLA-A2.1-/HLA-DR1-transgenic, H-2 class I-/class II-KO mice.

In some embodiments the HLA-A2.1-/HLA-DR1-transgenic, H-2 class I-/class II-KO mice express, in a β2m-KO context, a HLA-A2.1 monochain in which the human β2m is covalently linked by a peptidic arm to the HLA-A2.1 heavy chain. They further lack cell surface expression of conventional H-2 IA and IE class II molecules as a result of the inactivation of the H-2 IAβ$^b$ gene, since H-2 IEα is a pseudogene in the H-2$^b$ haplotype. The results provided herein demonstrate that such mice are deprived of cell surface expression of H-2 class I and class II molecules. However, it was reported in one case that a free class I heavy chain, in particular H-2 D$^b$, may exist on the surface of a β2m-KO mouse, and could induce an alloreactivity response. Even if this is so, because such mice are empty of peptide, they should not interfere in antigen-specific immune response (Bix, M. & Raulet, D., *J Exp Med* 176, 829-834 (1992)). This is supported by the report of Allen et al (Allen, H., Fraser, J., Flyer, D., Calvin, S. & Flavell, R., *Proc Natl Acad Sci USA* 83, 7447-7451 (1986)), in which they confirmed that H-2 D$^b$ is expressed at the cell surface even when there is no β2m present within the cell, but that such D$^b$ antigen is recognized by neither D$^b$-allospecific or D$^b$-restricted cytotoxic T lymphocytes. Furthermore, D$^b$ antigens are not recognized by most monoclonal antibodies of the native D$^b$.

Nonetheless, in HLA-DRα single transgenic mice, it was reported that unconventional HLA-DRα/H-2 IEβ$^b$ hybrid complexes may be expressed to some extent on the cell surface, at least in the absence of the HLA-DRβ chain (Lawrance, S. K. et al., *Cell* 58, 583-594 (1989)). In spite of this observation, these unconventional molecules were not detected serologically on cell surfaces in HLA-A2.1-/HLA-DR1-transgenic, H-2 class I-/class II-KO mice, even with mAb (17-3-3S), which is known to react with such hybrid molecules (Ozato, K., Mayer, N. & Sachs, D. H., *J Immunol* 124, 533-540 (1980)) (FIG. 1a and data not shown). In addition, the results obtained on studying HBsAg-specific and HIV 1-Gag-specific T cell responses of these mice were all indicative of exclusive usage of the HLA-A2.1 and HLA-DR1 molecules as restricting elements. This argues that the unconventional HLA-DRα/H-2 IEβ$^b$ hybrids were likely unstable compared to conventional HLA-DRα/HLA-DRβ molecules and that they may exist only in the absence of the HLA-DRβ chain. Mouse strains in which the entire (H-2 IAβ$^b$, IAα$^b$, IEβ$^b$) H-2 class II region has been deleted (Madsen, L. et al., *Proc Natl Acad Sci USA* 96, 10338-10343 (1999)), as well as the H-2 D$^b$ gene, are being analyzed to completely exclude this possibility. Preliminary analysis of splenocytes obtained from the first animals revealed a CD4+ T cell pool restoration similar to that observed in HLA-DR1-transgenic H-2 class II-KO (Iaβ$^{b°}$) mice, suggesting that the HLA-DR1-restricted CD4+ T cell responses of these new mice should be equivalent to those of the HLA-A2.1-/HLA-DR1-transgenic, H-2 class I-/class II-KO mice.

The peripheral CD8+ T lymphocytes of HLA-A2.1-/HLA-DR1-transgenic, H-2 class I-/class II-KO mice, compared to parental HLA-A2.1-transgenic H-2 class I-KO mice, are quantitatively and qualitatively similar with full diversification, at least in terms of BV segment usage, of the TCR repertoire. Partial restoration compared to wild-type animals, especially of the CD8+ T cell pool, has been a constant observation in single HLA-transgenic mice expressing a chimeric (α3 domain of mouse origin) HLA-A2.1 molecule (Pascolo, S. et al., *J Exp Med* 185, 2043-2051 (1997)). Regardless of the α3 domain substitution, the interaction remains suboptimal between mouse CD8 and HLA-A2.1 molecules, since co-crystal analysis has documented that human CD8 also contacts the HLA-A2.1 heavy chain α2 domain (Gao, G. F. et al., *Nature* 387, 630-634 (1997)). Suboptimal cooperation might also occur in the endoplasmic reticulum where many molecules (TAP, tapasine, ERp 57) assist MHC class I molecule biosynthesis. However, at this stage, the only documented functional difference between these mice and human endoplasmic reticulum molecules, namely the efficient transport by human but not mouse TAP of COOH-terminus positively charged cytosolic peptides (Momburg, F., Neefjes, J. J. & Hammerling, G. J., *Curr Opin Immunol* 6, 32-37 (1994)), is not relevant for HLA-A2.1 molecules which bind peptides with a hydrophobic C-terminus, since these peptides are transported efficiently by mouse and human TAP. Even though the number of CD8+ T lymphocytes is lower in both single HLA-A2.1-transgenic, H-2 class I-KO mice and in HLA-A2.1-/HLA-DR1-transgenic H-2 class I-/class II-KO mice, they respond efficiently against HBsAg and, importantly, the latter mice develop antibody, helper and cytolytic cell responses similar to humans.

One of the difficulties hampering the design of T-epitope-based vaccines targeting T lymphocytes is HLA class I/class II molecule polymorphism. HLA-A2.1 and HLA-DR1 molecules are expressed by a significant proportion of individuals in human populations (30 to 50% for HLA-A2.1, 6 to 18% for HLA-DR1). Even though the functional clustering of HLA class I molecules in superfamilies is based on significant redundancy of the presented sets of peptides[34], individual analysis of the responses elicited by each HLA class I isotypic or allelic variant remains desirable to identify the optimal epitopes they present. This is particularly important to devise a new reagent, such as tetramer (HLA-class I or HLA-class II) to monitor the immune response. For the same reason, it would be helpful to obtain strains of mice co-expressing HLA-A2.1 with other HLA class II molecules, even if the binding of peptides to HLA class II molecules is less restrictive than to class I molecules. Based on the disclosure herein, additional HLA class I-/class II-transgenic, H-2 class I-/class II-KO mice can be constructed for these and other purposes.

Whereas HLA-transgenic H-2-KO mice enable a detailed analysis and optimization of the immunogenicity of antigenic peptides with excellent transposability to humans (Rohrlich, P. S. et al., *Int Immunol* 15, 765-772 (2003); Loirat, D., Lemonnier, F. A. & Michel, M. L., *J Immunol* 165, 4748-4755

(2000); Scardino, A. et al., *Eur J Immunol* 31, 3261-3270 (2001)) this is less evident for vaccine adjuvant-formulation studies. This could be due to differences between the two species in the various effectors that are mobilized early in response to an antigenic challenge. Increasing fundamental knowledge of innate immunity might, in the future, lead to a more complete humanization of the mouse immune system.

In conclusion, the disclosure herein describes an optimized, humanized transgenic mouse model, whose H-2 class I (mouse β2m) and class II (H-2 IAβ$^b$) genes have been deleted and replaced with equivalent human genes HHD (HLA-A*0201), HLA-DRA*0101 and HLA-DRB1*0101. Cellular immunity in the HLA-A2.1-/HLA-DR1-transgenic H-2 class I-/class II-KO mice is completely restricted by the human HLA molecules, with a complete absence of immune responses restricted by the murine MHC molecules. The absence of competition between murine MHC and human (transgenic) HLA immune responses allows for use of these mice to characterize epitopes in human vaccines that require collaboration between HLA-restricted CD4$^+$ T helper and HLA-restricted CD8$^+$ T cytolytic cells.

"HLA" is the human MHC complex, and "H-2" the mouse MHC complex. The human complex comprises three class I a-chain genes, HLA-A, HLA-B, and HLA-C, and three pairs of MHC class II α- and β-chain genes, HLA-DR, -DP, and -DQ. In many haplotypes, the HLA-DR cluster contains an extra β-chain gene whose product can pair with the DRα chain, and so the three sets of genes give rise to four types of MHC class II molecules. In the mouse, the three class I a-chain genes are H-2-L, H-2-D, and H-2-K. The mouse MHC class II genes are H-2-A and H-2-E.

It is known in the art that genetic diversity exists between the HLA genes of different individuals as a result of both polymorphic HLA antigens and distinct HLA alleles. Accordingly, embodiments of the invention disclosed herein may substitute one polymorphic HLA antigen for another or one HLA allele for another. Examples of HLA polymorphisms and alleles can be found, for example, at http://www.anthonynolan.org.uk/HIG/data.html and http://www.ebi.ac.uk/imgt/hla, and in Genetic diversity of HLA: Functional and Medical Implication, Dominique Charon (Ed.), EDK Medical and Scientific International Publisher, and The HLA FactsBook, Steven G. E. Marsh, Peter Parham and Linda Barber, AP Academic Press, 2000.

A "disrupted" gene is one that has been mutated using homologous recombination or other approaches known in the art. A disrupted gene can be either a hypomorphic allele of the gene or a null allele of the gene. One of skill in the art will recognize that the type of allele to be used can be selected for any particular context. In many embodiments of the invention, a null allele is preferred.

"Homologous recombination" is a general approach for targeting mutations to a preselected, desired gene sequence of a cell in order to produce a transgenic animal (Mansour, S. L. et al., Nature 336:348-352 (1988); Capecchi, M. R., *Trends Genet.* 5:70-76 (1989); Capecchi, M. R., *Science* 244:1288-1292 (1989); Capecchi, M. R. et al., In: Current Communications in Molecular Biology, Capecchi, M. R. (ed.), Cold Spring Harbor Press, Cold Spring Harbor, N.Y. (1989), pp. 45-52; Frohman, M. A. et al., *Cell* 56:145-147 (1989)).

It is now be feasible to deliberately alter any gene in a mouse (Capecchi, M. R., *Trends Genet.* 5:70-76 (1989); Frohman, M. A. et al., *Cell* 56:145-147 (1989)). Gene targeting involves the use of standard recombinant DNA techniques to introduce a desired mutation into a cloned DNA sequence of a chosen locus. That mutation is then transferred through homologous recombination to the genome of a pluripotent, embryo-derived stem (ES) cell. The altered stem cells are microinjected into mouse blastocysts and are incorporated into the developing mouse embryo to ultimately develop into chimeric animals. In some cases, germ line cells of the chimeric animals will be derived from the genetically altered ES cells, and the mutant genotypes can be transmitted through breeding.

Gene targeting has been used to produce chimeric and transgenic mice in which an nptII gene has been inserted into the β$_2$-microglobulin locus (Koller, B. H. et al., *Proc. Natl. Acad. Sci. (U.S.A.)* 86:8932-8935 (1989); Zijlstra, M. et al., *Nature* 342:435-438 (1989); Zijlstra, M. et al., *Nature* 344:742-746 (1989); DeChiaba et al., *Nature* 345:78-80 (1990)). Similar experiments have enabled the production of chimeric and transgenic animals having a c-abI gene which has been disrupted by the insertion of an nptil gene (Schwartzberg, P. L. et al., *Science* 246:799-803 (1989)). The technique has been used to produce chimeric mice in which the en-2 gene has been disrupted by the insertion of an nptII gene (Joyner, A. L. et al., *Nature* 338:153-155 (1989)).

In order to utilize the "gene targeting" method, the gene of interest must have been previously cloned, and the intron-exon boundaries determined. The method results in the insertion of a marker gene (e.g., an nptil gene) into a translated region of a particular gene of interest. Thus, use of the gene targeting method results in the gross destruction of the gene of interest.

Significantly, the use of gene targeting to alter a gene of a cell results in the formation of a gross alteration in the sequence of that gene. The efficiency of gene targeting depends upon a number of variables, and is different from construct to construct.

The chimeric or transgenic animal cells of the present invention are prepared by introducing one or more DNA molecules into a cell, which may be a precursor pluripotent cell, such as an ES cell, or equivalent (Robertson, E. J., In: Current Communications in Molecular Biology, Capecchi, M. R. (ed.), Cold Spring Harbor Press, Cold Spring Harbor, N.Y. (1989), pp. 39-44). The term "precursor" is intended to denote only that the pluripotent cell is a precursor to the desired ("transfected") pluripotent cell, which is prepared in accordance with the teachings of the present invention. The pluripotent (precursor or transfected) cell can be cultured in vivo in a manner known in the art (Evans, M. J. et al., Nature 292:154-156 (1981)) to form a chimeric or transgenic animal.

Any ES cell can be used in accordance with the present invention. It is, however, preferred to use primary isolates of ES cells. Such isolates can be obtained directly from embryos, such as the CCE cell line disclosed by Robertson, E. J., In: Current Communications in Molecular Biology, Capecchi, M. R. (ed.), Cold Spring Harbor Press, Cold Spring Harbor, N.Y. (1989), pp. 39-44), or from the clonal isolation of ES cells from the CCE cell line (Schwartzberg, P. A. et al., Science 246:799-803 (1989), which reference is incorporated herein by reference). Such clonal isolation can be accomplished according to the method of E. J. Robertson (In: Teratocarcinomas and Embryonic Stem Cells: A Practical Approach, (E. J. Robertson, Ed.), IRL Press, Oxford, 1987), which reference and method are incorporated herein by reference. The purpose of such clonal propagation is to obtain ES cells, which have a greater efficiency for differentiating into an animal. Clonally selected ES cells are approximately 10-fold more effective in producing transgenic animals than the progenitor cell line CCE. For the purposes of the recombination methods of the present invention, clonal selection provides no advantage.

An example of ES cell lines, which have been clonally derived from embryos, are the ES cell lines, AB1 (hprt⁺) or AB2.1 (hprt⁻). The ES cells are preferably cultured on stromal cells (such as STO cells (especially SNC4 STO cells) and/or primary embryonic fibroblast cells) as described by E. J. Robertson (In: Teratocarcinomas and Embryonic Stem Cells: A Practical Approach, (E. J. Robertson, Ed., IRL Press, Oxford, 1987, pp 71-112), which reference is incorporated herein by reference. Methods for the production and analysis of chimeric mice are disclosed by Bradley, A. (In: Teratocarcinomas and Embryonic Stem Cells: A Practical Approach, (E. J. Robertson, Ed.), IRL Press, Oxford, 1987, pp 113-151), which reference is incorporated herein by reference. The stromal (and/or fibroblast) cells serve to eliminate the clonal overgrowth of abnormal ES cells. Most preferably, the cells are cultured in the presence of leukocyte inhibitory factor ("lif") (Gough, N. M. et al., *Reprod. Fertil. Dev.* 1:281-288 (1989); Yamamori, Y. et al., *Science* 246:1412-1416 (1989), both of which references are incorporated herein by reference). Since the gene encoding lif has been cloned (Gough, N. M. et al., *Reprod. Fertil. Dev.* 1:281-288 (1989)), it is especially preferred to transform stromal cells with this gene, by means known in the art, and to then culture the ES cells on transformed stromal cells that secrete lif into the culture medium.

As used herein, the term "transgene" refers to a nucleic acid sequence, which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can be operably linked to one or more transcriptional regulatory sequences and any other nucleic acid, such as introns, that may be necessary for optimal expression of a selected nucleic acid. Exemplary transgenes of the present invention encode, for instance an H-2 polypeptide. Other exemplary transgenes are directed to disrupting one or more HLA genes by homologous recombination with genomic sequences of an HLA gene.

A "functional transgene" is one that produces an mRNA transcript, which in turn produces a properly processed protein in at least one cell of the mouse comprising the transgene. One of skill will realize that the diverse set of known transcriptional regulatory elements and sequences directing post-transcriptional processing provide a library of options from which to direct the expression of a transgene is a host mouse. In many embodiments of the invention, expression of an HLA transgene under the control of an H-2 gene regulatory element may be preferred.

In some embodiments, the HLA class I transgene is an HLA-A2 transgene and the HLA class II transgene is an HLA-DR1 transgene. An example of an HLA-A2 transgene is one that comprises the HLA-A2 sequence provided in the sequence listing. An example of an HLA-DR1 transgene is one that comprises the HLA-DR1 sequence provided in the sequence listing.

In an embodiment, the invention provides a transgenic mouse deficient for both H2 class I and class II molecules, wherein the transgenic mouse comprises a functional HLA class I transgene and a functional HLA class II transgene. In some embodiments, the mouse has the genotype HLA-A2⁺ HLA-DR1⁺β2m°IAβ°. In other embodiments the HLA-A2 transgene comprises the HLA-A2 sequence provided in the sequence listing and the HLA-DR1 transgene comprises the HLA-DR1 sequence provided in the sequence listing.

The invention also provides isolated transgenic mouse cells. In some cases the cell comprises a disrupted H2 class I gene, a disrupted H2 class II gene, and a functional HLA class I or class II transgene. In others, the cell comprises a disrupted H2 class I gene, a disrupted H2 class II gene, a functional HLA class I transgene, and a functional HLA class II transgene. The HLA class I transgene can be an HLA-A2 transgene and the HLA class II transgene can be an HLA-DR1 transgene. In some cases, the HLA-A2 transgene comprises the HLA-A2 sequence provided in the sequence listing and the HLA-DR1 transgene comprises the HLA-DR1 sequence provided in the sequence listing.

In an embodiment, the invention provides an isolated transgenic mouse cell deficient for both H2 class I and class II molecules, wherein the transgenic mouse comprises a functional HLA class I transgene and a functional HLA class II transgene. The isolated transgenic mouse cells can have the genotype HLA-A2⁺HLA-DR1⁺β2m°IAβ°. The HLA-A2 transgene can comprise the HLA-A2 sequence provided in the sequence listing and the HLA-DR1 transgene can comprise the HLA-DR1 sequence provided in the sequence listing.

The isolated transgenic mouse cells of the invention can have the genotype of any mouse of the invention. However, the set of genotypes of the isolated transgenic mouse cells of the invention, and the set of genotypes of the mice of the invention are not necessarily entirely overlapping.

The isolated mouse cells of the invention can be obtained from a mouse or mouse embryo. In one embodiment, the mouse or mouse embryo has the same genotype as the cell to be obtained. In another embodiment, the mouse or mouse embryo has a different genotype than the cell to be obtained. After the cell is obtained from the mouse or mouse embryo, a gene of the cell can be disrupted by, for example, homologous recombination. Additionally, a functional transgene can be introduced into the genome of the cell by, for example, transfection. One of skill in the art will recognize that any suitable method known in the art can be applied to modify the genome of the cell to thereby obtain an isolated mouse cell having the desired genotype.

An additional object of the invention is an isolated transgenic mouse cell deficient for both H2 class I and class II molecules, wherein the transgenic mouse cell comprises a functional HLA class I transgene and a functional HLA class II transgene. In some embodiments, the transgenic mouse cell has the genotype HLA-A2⁺HLA-DR1⁺β2m°IAβ°. In other embodiments, the HLA-A2 transgene comprises the HLA-A2 sequence provided in the sequence listing and the HLA-DR1 transgene comprises the HLA-DR1 sequence provided in the sequence listing.

T cells play a central role in many aspects of acquired immunity, carrying out a variety of regulatory and defensive functions. When some T cells encounter an infected or cancerous cell, they recognize it as foreign and respond by acting as killer cells, killing the host's own cells as part of the cell-mediated immune response. Other T cells, designated helper T cells, respond to perceived foreign antigens by stimulating B cells to produce antibodies, or by suppressing certain aspects of a humoral or cellular immune response.

T helper cells (Th) orchestrate much of the immune response via the production of cytokines. Although generally identifiable as bearing the CD4 cell surface marker, these cells are functionally divided into Th1 or Th2 subpopulations according to the profile of cytokines they produce and their effect on other cells of the immune system.

The Th1 cells detect invading pathogens or cancerous host cells through a recognition system referred to as the T cell antigen receptor. Termed cellular immunity, Th1-related processes generally involve the activation of non-B cells and are frequently characterized by the production of IFN-γ. Nevertheless, although the Th1 system is primarily independent from the production of humoral antibodies, Th1 cytokines do promote immunoglobulin class switching to the $IgG_{2a}$ isotype.

Upon detection of a foreign antigen, most mature Th1 cells direct the release of IL-2, IL-3, IFN-γ, TNF-β, GM-CSF, high levels of TNF-α, MIP-1α, MIP-1β, and RANTES. These cytokines promote delayed-type hypersensitivity and general cell-mediated immunity. IL-2, for instance, is a T cell growth factor that promotes the production of a clone of additional T cells sensitive to the particular antigen that was initially detected. The sensitized T cells attach to and attack cells or pathogens containing the antigen.

In contrast, mature Th2 cells tend to promote the secretion of IL-3, IL-4, IL-5, IL-6, IL-9, IL-10, IL-13, GM-CSF, and low levels of TNF-α. In addition, the Th2 response promotes humoral immunity by activating B cells, stimulating antibody production and secretion, and inducing class switching to IgA, IgG, and IgE isotypes.

As used herein, an "antigen" comprises: 1) at least one HTL epitope, or 2) at least one CTL epitope or, 3) at least one B cell epitope, or 4) at least one HTL epitope and at least one CTL epitope, or 5) at least one HTL epitope and at least one B cell epitope, or 6) at least one CTL epitope and at least one B cell epitope, or 7) at least one HTL epitope and at least one CTL epitope and at least one B cell epitope. A "candidate antigen" is a molecule that is under investigation to determine whether it functions as an antigen.

A "humoral immune response" is antibody-mediated specific immunity.

An "epitope" is a site on an antigen that is recognized by the immune system. An antibody epitope is a site on an antigen recognized by an antibody. A T-cell epitope is a site on an antigen that binds to an MHC molecule. A TH epitope is one that binds to an MHC class II molecule. A CTL epitope is one that binds to an MHC class I molecule.

The antigen can comprise a polypeptide sequence or a polynucleotide sequence, which can comprise RNA, DNA, or both. In one embodiment, the antigen comprises at least one polynucleotide sequence operationally encoding one or more antigenic polypeptides. Used in this context, the word "comprises" intends that at least one antigenic polypeptide is provided by the transcription and/or translation apparatus of a host cell acting upon an exogenous polynucleotide that encodes at least one antigenic polypeptide, as described, for example in U.S. Pat. Nos. 6,194,389 and 6,214,808.

Antigens of the invention can be any antigenic molecule. Antigenic molecules include: proteins, lipoproteins, and glycoproteins, including viral, bacterial, parasitic, animal, and fungal proteins such as albumins, tetanus toxoid, diphtheria toxoid, pertussis toxoid, bacterial outer membrane proteins (including meningococcal outer membrane protein), RSV-F protein, malarial derived peptide, B-lactoglobulin B, aprotinin, ovalbumin, lysozyme, and tumor associated antigens such as carcinoembryonic antigen (CEA), CA 15-3, CA 125, CA 19-9, prostrate specific antigen (PSA), and the TM complexes of U.S. Pat. No. 5,478,556, which is incorporated herein by reference in its entirety; carbohydrates, including naturally-occurring and synthetic polysaccharides and other polymers such as ficoll, dextran, carboxymethyl cellulose, agarose, polyacrylamide and other acrylic resins, poly (lactide-co-glycolide), polyvinyl alcohol, partially hydrolyzed polyvinyl acetate, polyvinylpryrolidine, Group B Steptococcal and Pneumococcal capsular polysaccharides (including type III), *Pseudomonas aeruginosa* mucoexopolysaccharide, and capsular polysaccharides (including fisher type I), and *Haemophilus influenzae* polysaccharides (including PRP); haptens, and other moieties comprising low molecular weight molecules, such as TNP, saccharides, oligosaccharides, polysaccharides, peptides, toxins, drugs, chemicals, and allergens; and haptens and antigens derived from bacteria, rickettsiae, fungi, viruses, parasites, including Diphtheria, Pertussis, Tetanus, *H. influenzae, S. pneumoniae, E. Coli, Klebsiella, S. aureus, S. epidermidis, N. meningiditis,* Polio, Mumps, measles, rubella, Respiratory Syncytial Virus, Rabies, Ebola, Anthrax, Listeria, Hepatitis A, B, C, Human Immunodeficiency Virus I and II, Herpes simplex types 1 and 2, CMV, EBV, Varicella Zoster, Malaria, Tuberculosis, *Candida albicans,* and other *candida, Pneumocystis caringi, Mycoplasma,* Influenzae virus A and B, Adenovirus, Group A streptococcus, Group B streptococcus, *Pseudomonas aeryinosa,* Rhinovirus, Leishmania, Parainfluenzae, types 1, 2 and 3, Coronaviruses, *Salmonella,* Shigella, Rotavirus, Toxoplasma, Enterovirusses, and *Chlamydia trachomatis* and *pneumoniae.*

As used herein, a pharmaceutical composition or vaccine comprises at least one immunological composition, which can be dissolved, suspended, or otherwise associated with a pharmaceutically acceptable carrier or vehicle. Any pharmaceutically acceptable carrier can be employed for administration of the composition. Suitable pharmaceutical carriers are described in Remington's Pharmaceutical Sciences, 18th Edition (A. Gennaro, ed., 1990) Mack Pub., Easton, Pa., which is incorporated herein by reference in its entirety. Carriers can be sterile liquids, such as water, polyethylene glycol, dimethyl sulfoxide (DMSO), oils, including petroleum oil, animal oil, vegetable oil, peanut oil, soybean oil, mineral oil, sesame oil, and the like. Carriers can be in the form of mists, sprays, powders, waxes, creams, suppositories, implants, salves, ointments, patches, poultices, films, or cosmetic preparations.

Proper formulation of the pharmaceutical composition or vaccine is dependent on the route of administration chosen. For example, with intravenous administration by bolus injection or continuous infusion, the compositions are preferably water soluble, and saline is a preferred carrier. For transcutaneous, intranasal, oral, gastric, intravaginal, intrarectal, or other transmucosal administration, penetrants appropriate to the barrier to be permeated can be included in the formulation and are known in the art. For oral administration, the active ingredient can be combined with carriers suitable for inclusion into tablets, pills, dragees, capsules, liquids, gels, syrups, slurries, suspensions, and the like. Time-sensitive delivery systems are also applicable for the administration of the compositions of the invention. Representative systems include polymer base systems, such as poly(lactide-glycoside), copolyoxalates, polycaprolactones, polyesteramides, polyorthoesters, polyhydroxybutyric acid and polyanhydrides. These and like polymers can be formulated into microcapsules according to methods known in the art, for example, as taught in U.S. Pat. No. 5,075,109, which is incorporated herein by reference in its entirety. Alternative delivery systems appropriate for the administration of the disclosed immunostimulatory compounds of the invention include those disclosed in U.S. Pat. Nos. 6,194,389, 6,024,983 5,817, 637, 6,228,621, 5,804,212, 5,709,879, 5,703,055, 5,643,605, 5,643,574, 5,580,563, 5,239,660, 5,204,253, 4,748,043, 4,667,014, 4,452,775, 3,854,480, and 3,832,252 (each of which is incorporated herein by reference in its entirety).

Aqueous dextrose and glycerol solutions can also be employed as liquid carriers, particularly for injectable or aerosol solutions. For administration by aerosol, as by pressurized spray or nebulizer, suitable propellants can be added as understood by those familiar with the art. The immunological composition can also be formulated with solubilizing agents; emulsifiers; stabilizers; dispersants; flavorants; adjuvants; carriers; topical anesthetics, such as lidocaine, xylocaine, and the like; antibiotics; and known or suspected anti-viral, anti-fungal, anti-parasitic, or anti-tumor compounds.

An "adjuvant" is a composition that promotes or enhances an immune response to a target antigen. One of skill in the art can select an appropriate adjuvant for use in practicing the present invention in view of the disclosure herein.

The present invention encompasses methods of treating a patient in need of immune stimulation by administering a composition comprising one or more antigens of the invention. As used herein, treatment encompasses corrective, restorative, ameliorative, and preventive methods relating to any disease, condition, abnormality, or symptom. Treatment further encompasses the elicitation or suppression of an immune response in an experimental animal or ex vivo.

Thus, treatment comprises administering an immunostimulatory amount of any of the immunostimulatory compositions of the invention by any method familiar to those of ordinary skill in the art, commonly including oral and intranasal routes, and intravenous, intramuscular, and subcutaneous injections, but also encompassing, intraperitoneal, intracorporeal, intra-articular, intraventricular, intrathecal, topical, tonsillar, mucosal, transdermal, intravaginal administration and by gavage.

As is recognized by the skilled practitioner, choosing an appropriate administration method may contribute to the efficacy of a treatment, and local administration may be preferred for some applications. Acceptable routes of local administration include subcutaneous, intradermal, intraperitoneal, intravitreal, inhalation or lavage, oral, intranasal, and directed injection into a predetermined tissue, organ, joint, tumor, or cell mass. For example, mucosal application or injection into mucosal lymph nodes or Peyer's patches may promote a humoral immune response with substantial IgA class switching. Alternatively, targeted injection into a lesion, focus, or affected body site may be applicable for the treatment of solid tumors, localized infections, or other situs requiring immune stimulation.

Alternatively, cells of the immune system (e.g., T cells, B cells, NK cells, or oligodendrocytes) can be removed from a host and treated in vitro. The treated cells can be further cultured or reintroduced to a patient (or to a heterologous host) to provide immune stimulation to the patient or host. For example, bone marrow cells can be aspirated from a patient and treated with an HDR to stimulate global or specific immunity. High-dose radiation, or comparable treatments, can then be used to destroy the remaining immune cells in the patient. Upon re-implantation, the autologous stimulated cells will restore normal immune function in the patient. Alternatively, NK and/or T cells isolated from a patient suffering from cancer may be exposed in vitro to one or more antigens specific to the patient's cancer. Upon re-implantation into the patient, the antigen-stimulated cells will deploy a vigorous cellular immune response against the cancerous cells.

An immunostimulatory (efficacious) amount refers to that amount of vaccine that is able to stimulate an immune response in a patient, which is sufficient to prevent, ameliorate, or otherwise treat a pathogenic challenge, allergy, or immunologic abnormality or condition. An immunostimulatory amount is that amount, which provides a measurable increase in a humoral or cellular immune response to at least one epitope of the antigen as compared to the response obtained if the antigen is administered to the patient without prior treatment with the vaccine. Thus, for example, an immunostimulatory amount refers to that amount of an antigen-containing composition that is able to promote the production of antibodies directed against an antigenic epitope of interest or stimulate a detectable protective effect against a pathogenic or allergenic challenge or to promote a protective CTL response against an antigenic epitope of interest.

Treatment with an immunostimulatory amount of an antigen-containing composition of the invention comprises effecting any directly, indirectly, or statistically observable or measurable increase or other desired change in the immune response in a host, specifically including an ex vivo tissue culture host, comprising at least one cell of the immune system or cell line derived therefrom. Host cells can be derived from human or animal peripheral blood, lymph nodes or the like. Preferred tissue culture hosts include freshly isolated T cells, B cells, macrophages, oligodendrocytes, NK cells, and monocytes, each of which can be isolated or purified using standard techniques. Observable or measurable responses include, B or T cell proliferation or activation; increased antibody secretion; isotype switching; increased cytokine release, particularly the increased release of one or more of IL-1, IL-2, IL-3, IL-4, IL-5, IL-6, IL-9, IL-10, IL-12, IL-13, GM-CSF, IFN-$\gamma$, TNF-$\alpha$, TNF-$\beta$, GM-CSF, MIP-1$\alpha$, MIP-1$\beta$, or RANTES; increased antibody titer or avidity against a specific antigen; reduced morbidity or mortality rates associated with a pathogenic infection; promoting, inducing, maintaining, or reinforcing viral latency; suppressing or otherwise ameliorating the growth, metastasis, or effects of malignant and non-malignant tumors; and providing prophylactic protection from a disease or the effects of a disease.

Where the suppression of an immunological response is desired, for example, in the treatment of autoimmune disease or allergy, an effective amount also encompasses that amount sufficient to effect a measurable or observable decrease in a response associated with the condition or pathology to be treated.

The amount of an antigen-containing composition to be administered and the frequency of administration can be determined empirically and will take into consideration the age and size of the patient being treated, and the condition or disease to be addressed. An appropriate dose is within the range of 0.01 μg to 100 μg per inoculum, but higher and lower amounts may also be indicated. Secondary booster immunizations can be given at intervals ranging from one week to many months later.

The following examples demonstrate certain embodiments of the invention. One of ordinary skill in the art will recognize the numerous modifications and variations that may be performed without altering the spirit or scope of the present invention. Such modifications and variations are believed to be encompassed within the scope of the invention. The examples do not in any way limit the invention.

EXAMPLES

The following experimental techniques and reagents were used to demonstrate certain nonlimiting embodiments of the invention.

Transgenic Mice

The HLA-DR1-transgenic H-2 class II-KO (IA $\beta^{b°}$) mice were obtained at the Institut Pasteur of Lille by crossing HLA-DR1-transgenic mice (Altmann, D. M. et al., *J Exp Med* 181, 867-875 (1995)) with H-2 class II-KO (IA $\beta^{b\circ}$) mice (Rohrlich, P. S. et al., *Int Immunol* 15, 765-772 (2003)). The HLA-A2.1-transgenic mice, expressing a chimeric monochain (HHD molecule: α1-α2 domains of HLA-A2.1, α3 to cytoplasmic domains of H-2 $D^b$, linked at its N-terminus to the C terminus of human β2m by a 15 amino-acid peptide linker) were created (Pascolo, S. et al., *J Exp Med* 185, 2043-2051 (1997)). HLA-A2.1 (HHD)-transgenic H-2 class I-KO and HLA-DR1-transgenic H-2 class II-KO (IA $\beta^{b\circ}$) mice were intercrossed and progenies screened until HLA-A2.1$^{+/-}$/HLA-DR1$^{+/-}$ double transgenic H-2-class I (β2m$^\circ$)-/class II (IAβ$^\circ$)-KO animals were obtained and used for the experiments described herein. HLA-A2.1$^{+/-}$ single transgenic H-2-class I (β2m$^\circ$)-/class II (IAβ$^\circ$)-KO mice were used as controls in the protection assays. Mice were bred in the animal facilities at the Institut Pasteur, Paris; all protocols were reviewed by the Institut Pasteur competent authority for compliance with the French and European regulations on Animal Welfare and with Public Health Service recommendations.

Genotyping

The HLA-DRB1*0101, HLA-DRA*0101 and HLA-A*0201 transgenes were detected by PCR. Tail-DNA was extracted after overnight incubation at 56° C. in 100 mM NaCl, 50 mM Tris-HCl pH 7.2, 100 mM EDTA, 1% SDS and 0.5 mg/ml proteinase K, followed by the addition of 250 µl of saturated NaCl solution and isopropanol precipitation. The samples were washed (3×) in 70% ethanol and resuspended in 150 µl of 10 mM Tris-HCl, 1 mM EDTA pH 8. PCR conditions were: 1.5 mM MgCl2, 1.25 U of Taq Polymerase, buffer supplied by the manufacturer (InVitrogen, Carlsbad, Calif.), 1 cycle (7 min, 94° C.), 40 cycles (30 sec, 94° C.; 30 sec, 60° C.; 1 min, 72° C.), 1 cycle (4 min, 72° C.), using as forward and reverse primers, for HHD: 5'CAT TGA GAC AGA GCG CCT GGC ACA GAA GCA G 3'(SEQ ID NO:5) and 5'GGA TGA CGT GAG TAA ACC TGA ATC TTT GGA GTA CGC 3', (SEQ ID NO:6); for HLA-DRB1*0101: 5' TTC TTC AAC GGG ACG GAG CGG GTG 3'(SEQ ID NO:7) and 5' CTG CAC TGT GAA GCT CTC ACC AAC 3'(SEQ ID NO:8) and for HLA-DRA*0101: 5' CTC CAA GCC CTC TCC CAG AG 3'(SEQ ID NO:9) and 5' ATG TGC CTT ACA GAG GCC CC 3' (SEQ ID NO:10).

FACS Analysis

Cytofluorimetry studies were performed on red-blood cell-depleted, Lympholyte M-purified (Tebu-bio, Le Perray en Yvelines, France) splenocytes using FITC-conjugated W6/32 (anti-HLA-ABC, Sigma, St Louis, Mo.) and biotinilated anti-28-8-6S (anti-H-2 $K^b/D^b$, BD Biosciences, San Diego, Calif.) m.Ab. CD4$^+$ and CD8$^+$ T lymphocytes were stained using PE-labeled CT-CD4 anti-mouse CD4 (CALTAG, South San Francisco, Calif.) and FITC-labeled 53-6.7 anti-mouse CD8 m.Ab (BD Biosciences). Analysis of MHC class II molecule expression was performed on B220$^+$ B lymphocytes positively selected on MS columns (Miltenyi Biotec, Bergisch Gladbach, Germany). Following saturation of Fc receptors with 2.4G2 m.Ab, expression of HLA-DR1 and H-2 IA$^b$ was analyzed using FITC-labeled L243 (anti-HLA-DR) and PE-labeled AF6-120.1 (anti-H-2 IAβ$^b$) m.Ab (BD Biosciences). Paraformaldehyde fixed cells were analyzed with a FACS-Calibur (Becton Dickinson, Bedford, Mass.).

Immunoscope Analyses

CD4$^+$ and CD8$^+$ T cells from naive mice were positively selected on Auto-Macs (Miltenyi Biotec), RNA prepared using RNA Easy Kit (Qiagen, Hilden, Germany) and used for cDNA synthesis. The cDNA was PCR-amplified using forward primers specific for each BV segment family and a reverse primer shared by the two BC segments. PCR-products were subjected to a run-off-elongation with internal BC FAM-tagged primer. The run-off products were loaded on a 6% acrylamide/8 M urea gel for separation (7 h, 35 W) with a 373A DNA sequencer (Perkin Elmer Applied Biosystem, Foster City, Calif.). Data were analyzed using immunoscope software (Pannetier, C. et al., *Proc Natl Acad Sci USA* 90, 4319-4323 (1993)).

Peptides

The HLA-A2 binding peptides HBsAg$_{348-357}$ GLSPTVWLSV (SEQ ID NO:11) and HBsAg$_{335-343}$ WLSLLVPFV (SEQ ID NO:12), the H-2 $K^b$ binding peptides HBsAg$_{371-378}$ ILSPFLPL(SEQ ID NO:13), the HLA-DR1 binding peptide HBsAg$_{180-195}$ QAGFFLLTRILTIPQS (SEQ ID NO:14), the H-2 IA$^b$ binding peptide HBsAg$_{126-138}$ RGLYFPAGGSSSG (SEQ ID NO:15) and the preS2 peptide HBsAg$_{109-134}$ MQWNSTTFHQTLQDPRVRGLYFPAGG (SEQ ID NO:16) were synthesized by Neosystem (Strasbourg, France) and dissolved in PBS-10% DMSO at a concentration of 1 mg/ml. The numbering of the amino acid sequence of peptides starts from the first methionine of the HBV ayw subtype preS1 domain.

Immunization with DNA Encoding the S2-S Proteins of HBV

The pCMV-S2.S plasmid vector (Michel, M. L. et al., *Proc Natl Acad Sci USA* 92, 5307-5311 (1995)) coding for the preS2 and the S HBV surface antigens expressed under the control of the human CMV immediate early gene promotor was purified on Plasmid Giga Kit columns under endotoxin free conditions (Qiagen). Anesthesized mice were injected (50 µg each side) into regenerating tibialis anterior muscles, as previously described (Davis, H. L., Michel, M. L. & Whalen, R. G., *Hum Mol Genet* 2, 1847-1851 (1993)).

T Cell Proliferation Assay

Twelve days after the last immunization, red-blood cell-depleted, Ficoll-purified splenocytes (5.10$^6$ cells/25 cm$^2$ culture flask (Techno Plastic Products (TPP), Trasadingen, Switzerland)) were co-cultured with peptide-pulsed (20 µg/ml), γ-irradiated (180 Gy) LPS-blasts (5.10$^6$ cells/ culture flask) in RPMI medium supplemented with 10% FCS, 10 mM HEPES, 1 mM sodium pyruvate, 5×10$^{-5}$ M 2-mercaptoethanol, 100 I.U/ml penicillin and 100 µg streptomycin, as described (Loirat, D., Lemonnier, F. A. & Michel, M. L., *J Immunol* 165, 4748-4755 (2000)). On day 7, for proliferation assays, cells were plated (5×10$^5$ cells/well of flat bottomed 96 well microplates, (TPP)) with peptide-pulsed irradiated LPS-Blasts (2×10$^5$ cells/well) for 72 h in complete RPMI medium supplemented with 3% FCS. Cells were pulsed for the final 16 h with 1 µCi of ($^3$H)-thymidine per well before being harvested on filtermates with a TOMTEC collector (Perkin Elmer Applied Biosystem), and incorporated radioactivity was measured on a micro-β counter (Perkin Elmer Applied Biosystem). Results are given as stimulation index (SI)=cpm with specific peptide/cpm with irrelevant peptide.

Measurement of CTL Activity

Cytotoxicity assays were performed on the same immune splenocyte populations as the proliferation assays. Responder cells (5.10$^6$ cells/25 cm$^2$ culture flask, TPP) and stimulating peptide-pulsed (20 µg/ml), γ-irradiated (180 Gy) LPS-blasts (5.10$^6$ cells/ culture flask) were co-cultured for 7 days in the same supplemented RPMI medium as for proliferation assays. Cytolytic activity was tested in a standard 4 h $^{51}$Cr assay against RMA-S HHD target cells pulsed with 10 µg/ml of the experimental or control peptides. Specific lysis, in %, was calculated in duplicates, according to:

[experimental−spontaneous release]/[maximal−spontaneous release]×100, substracting the non-specific lysis observed with the control peptide.

Measurement of in vivo Antibody Production

At various times before and after DNA injection, blood was collected from mice by retrobulbar puncture with heparinized glass pipettes, and sera recovered by centrifugation were assayed for anti-HBs and anti-preS2 by specific ELISA. Purified recombinant particles containing HBV small S protein (1 ug/ml) or preS2 (120-145) synthetic peptide (1 ug/ml) were used as the solid phase. After blocking with PBST (PBS containing 0.1% Tween 20) supplemented with 10% FCS, serial dilutions were added. After extensive washing, the bound antibodies were detected with anti mouse Ig (total IgG) labeled with horseradish peroxidase (Amersham, Little Chalfont, UK). Antibody titers were determined by the serial end-point dilution method. Mouse sera were tested individually, and titers were the mean of at least three determinations. Serum dilutions below 1/100 were considered negative.

Antibody Titration

Sera from immunized mice were individually assayed by ELISA (Michel, M. L. et al., *Proc Natl Acad Sci USA* 92, 5307-5311 (1995)) on either purified HBV middle and small proteins or preS2 synthetic HBs$_{109-134}$. peptide, After blocking with PBS 1× supplemented with 0.1% Tween 20, 10% FCS and washings (×3), bound antibodies were detected with horseradish peroxidase-labeled anti-mouse IgG (Amersham, Little Chalfont, UK). Antibody titers (means of at least 3 determinations) were determined by the serial end-point dilution method. Titers below 1/100 were considered negative.

Vaccinia Challenge and Plaque Assay

DNA-injected mice were challenged intraperitoneally 12 days post last injection with $10^7$ PFU of recombinant vaccinia virus (Western Reserve strain) expressing either the HbsAg (Smith, G. L., Mackett, M. & Moss, B., *Nature* 302, 490-495 (1983)) or the HBx protein (Schek, N., Bartenschlager, R., Kuhn, C. & Schaller, H., *Oncogene* 6, 1735-1744. (1991)) kindly provided, respectively, by Dr B. Moss and Dr H. Schaller. Four days later, ovaries were assayed for rVV titers by plaque assay on BHK 21 cells (Buller, R. M. & Wallace, G. D., *Lab Anim Sci* 35, 473-476 (1985).

Example 1

Cell Surface Expression of MHC Molecules

Figure 1B:
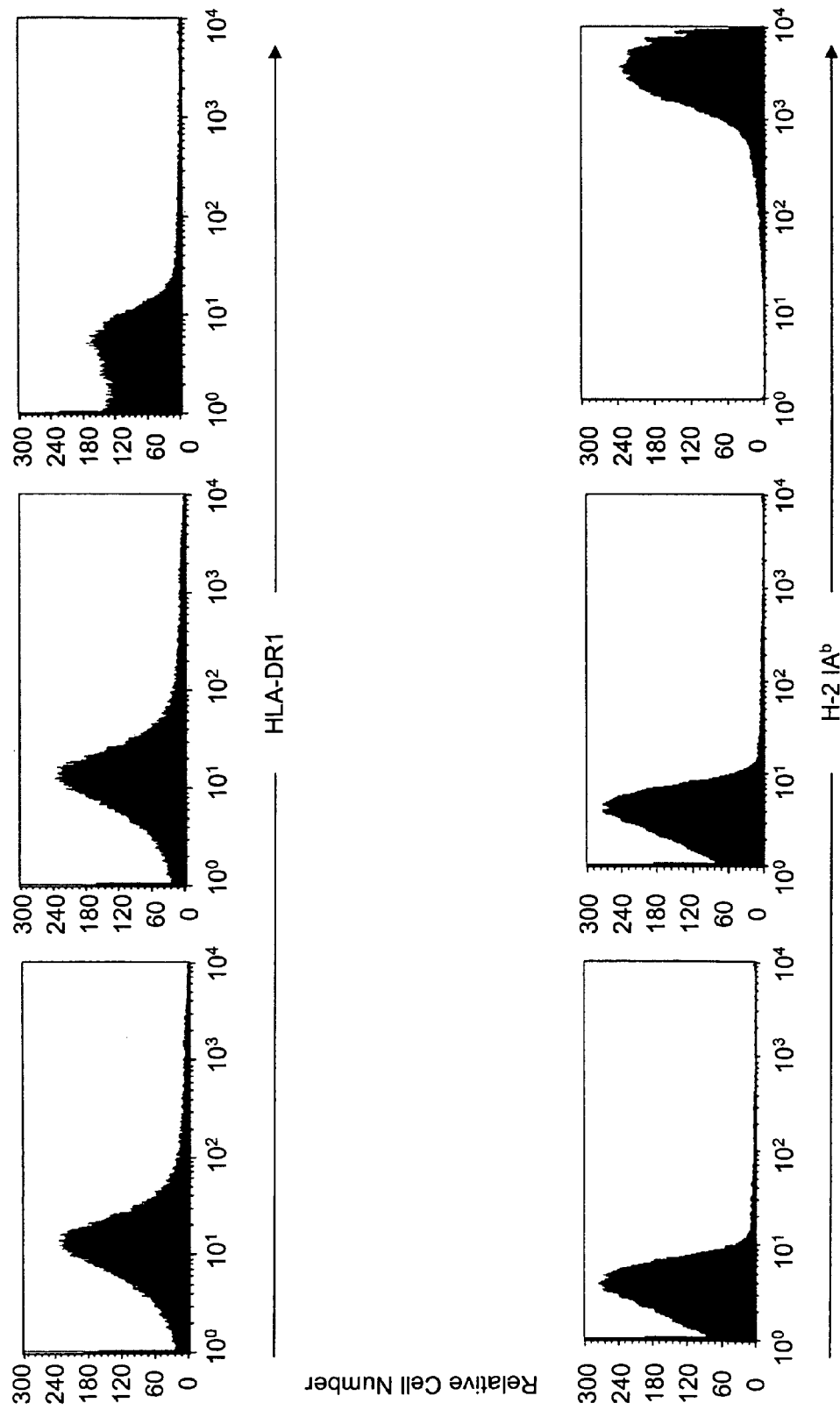

Cell surface expression of the HLA-A2.1, H-2 $K^b/D^b$, HLA-DR1, and H-2 $IA^b$ molecules was evaluated on splenocytes by flow cytometry. As illustrated in FIG. 1a, a similar level of HLA-A2.1 expression was observed in HLA-A2.1-/HLA-DR1-transgenic, H-2 class I-/class II-KO mice and HLA-A2.1-transgenic, H-2 class I-KO mice, while HLA-A2.1 was absent and H-2 $K^b/D^b$ expressed exclusively in HLA-DR1-transgenic, H-2 class II-KO mice. Cell surface expression of HLA-DR1 and H-2 $IA^b$ was measured on B220$^+$-enriched B cells. As shown in FIG. 1b, a similar level of HLA-DR1 expression was observed in HLA-A2.1-/HLA-DR1-transgenic, H-2 class I-/class II-KO mice and HLA-DR1-transgenic, H-2 class II-KO mice, whereas no expression was detected in HLA-A2.1-transgenic, H-2 class I-KO mice. Cell surface expression of the transgenic molecules (especially HLA-DR1) was, however, lower than the expression of endogenous H-2 class I and class II molecules.

Example 2

Peripheral CD4$^+$ and CD8$^+$ T Cells

Figure 2A:
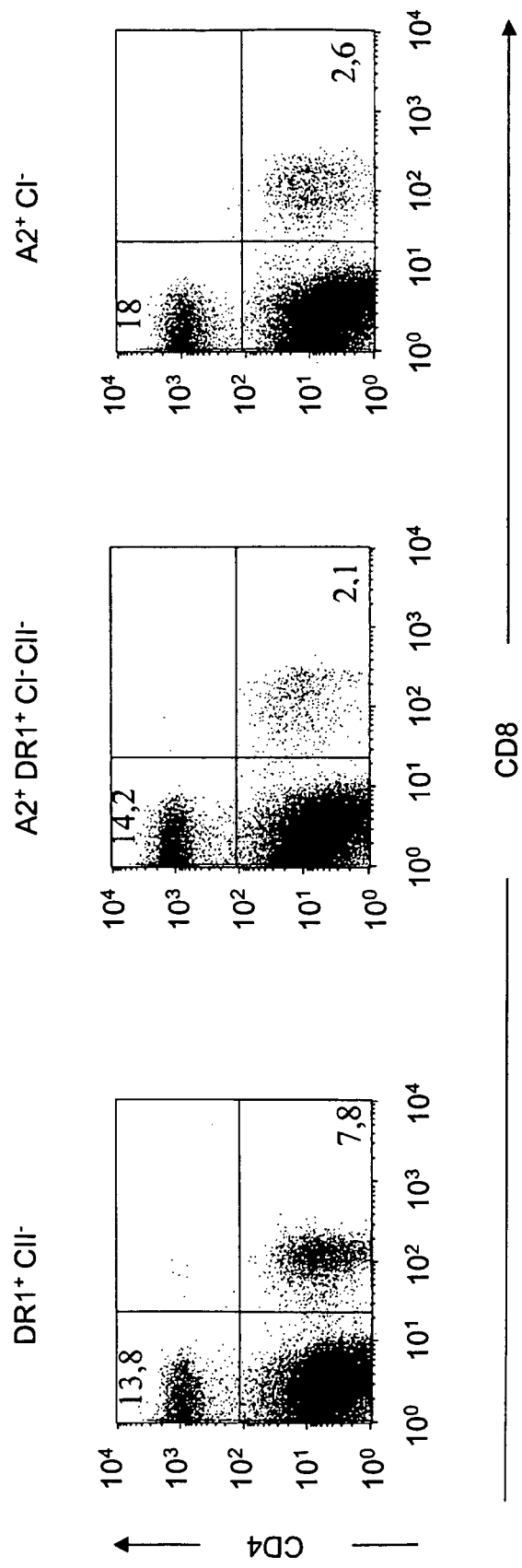
FIG. 2 shows CD8+ and CD4+ splenic T cell numbers and BV segment usage (based on an immunoscope analysis) in mice of the indicated genotypes. (a) Splenocytes from HLA-DR1-transgenic H-2 class II-KO (DR1+ CII−, left panel), HLA-A2.1-/HLA-DR1-transgenic H-2 class I-/class II-KO (A2+ DR1+ CI− CII−, central panel), and HLA-A2.1-transgenic H-2 class I-KO (A2+ CI−, right panel) mice were stained with PE-labeled CT-CD4 (anti-mouse CD4, in ordinates) and FITC-labeled 53-6.7 (anti-mouse CD8, in abcissas) m.Ab. Numbers correspond to percentages of CD4+ (upper left square) or CD8+ (lower right square) T cells in total splenocytes. (b and c) Immunoscope RT-PCR analysis of purified splenic CD8+(b) and CD4+ (c) T cells for BV segment family (1-20) usage using forward BV family (1-20) specific and reverse BC primers. A typical profile for a BV segment family productively rearranged includes a series of peaks with a Gaussian-like distribution differing in length by 3 nucleotides. The Figure illustrates the results obtained with a HLA-A2.1-/HLA-DR1-transgenic H-2 class I-/class II-KO representative mouse.

CD4$^+$ and CD8$^+$ splenic T cell numbers were determined by immunostaining and flow cytometry analysis as illustrated in FIG. 2a.

CD4$^+$ T cells represented 13-14% of the splenocyte population in both HLA-A2.1-/HLA-DR1-transgenic, H-2 class I-/class II-KO mice and HLA-DR1-transgenic, H-2 class II-KO mice. In contrast, only 2-3% of the cells were CD4$^+$ in H-2 class II-KO mice (data not shown), in agreement with the initial report on mice lacking MHC class II molecules (Cosgrove, D. et al., *Cell* 66, 1051-1066 (1991)). As expected, expression of transgenic HLA-A2.1 molecules led to an increase in the size of the peripheral CD8$^+$ T cell population, which reached 2-3% of the total splenocytes in both HLA-A2.1-/HLA-DR1-transgenic, H-2 class I-/class II-KO mice and HLA-A2.1-transgenic, H-2 class I-KO mice, compared to 0.6-1% in the β2 microglobulin (β2m)-KO MHC class I-deficient mice (Pascolo, S. et al., *J Exp Med* 185, 2043-2051 (1997)).

The results presented in Examples 1 and 2 show that:
(1) In the HLA-A2$^+$HLA-DR1$^+$β2m°IAβ° mouse, the expression of HLA-A2 molecules, the absence of expression of H2-K$^b$ molecules, the number of CD8$^+$ peripheral T-lymphocytes, and the diversity of the CD8$^+$ T repertoire are generally comparable to the HLA-A2$^+$β2m° mouse;
(2) In the HLA-A2$^+$HLA-DR1$^+$β2m°IAβ° mouse, the expression of HLA-DR1 molecules, the absence of expression of H2-IA$^b$ molecules, the number of CD4$^+$ T-lymphocytes, and the diversity of the CD4$^+$ repertoire are generally comparable to the HLA-DR1$^+$IAβ° mouse; and
(3) The HLA-A2$^+$HLA-DR1$^+$β2m°IAβ° mouse has all the characteristic advantages found in HLA-A2$^+$β2m° mice, and the HLA-DR1$^+$IAβ° mice.

Example 3

TCR BV Segment Usage

Figure 2B:
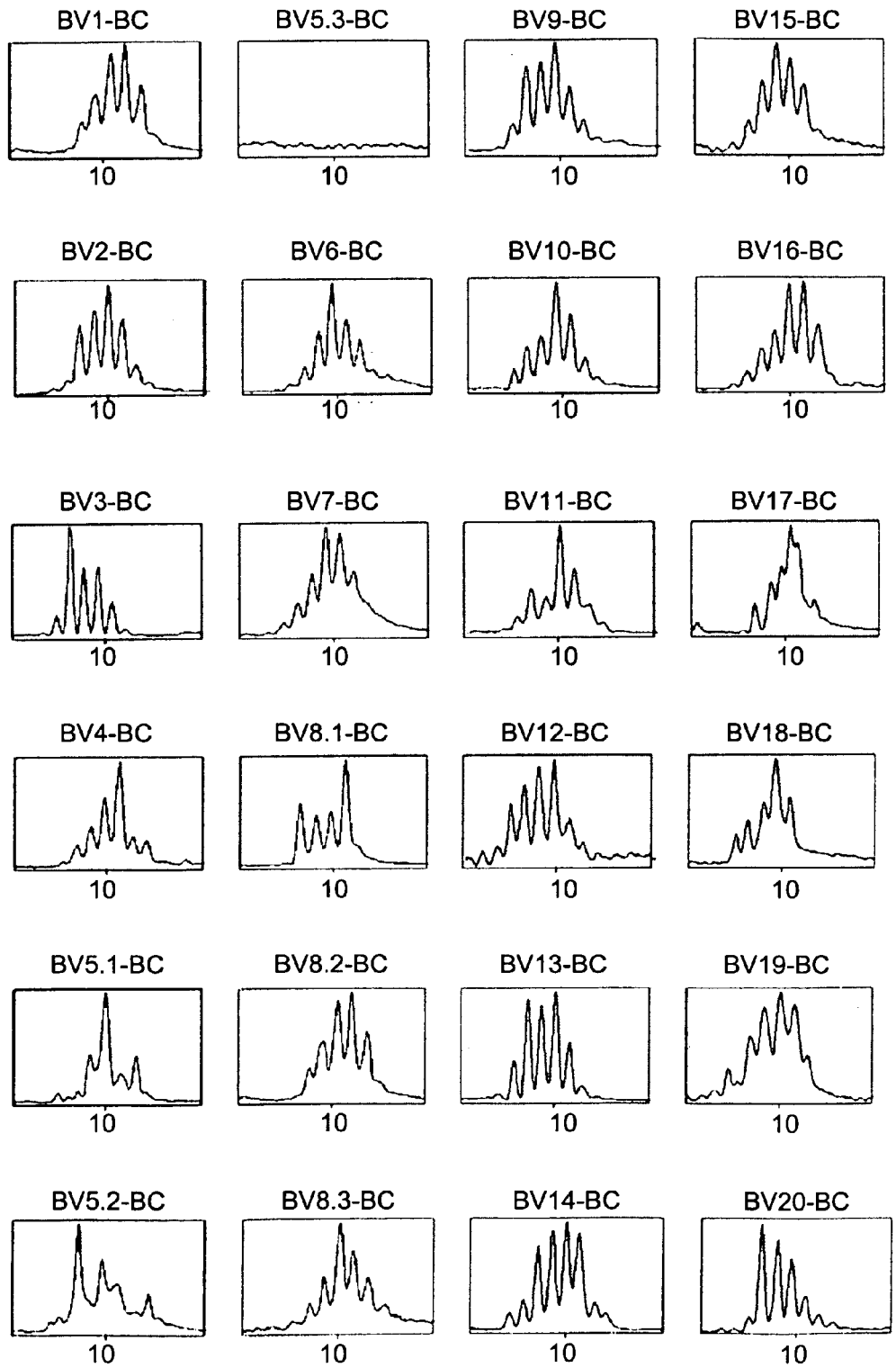
Figure 2C:
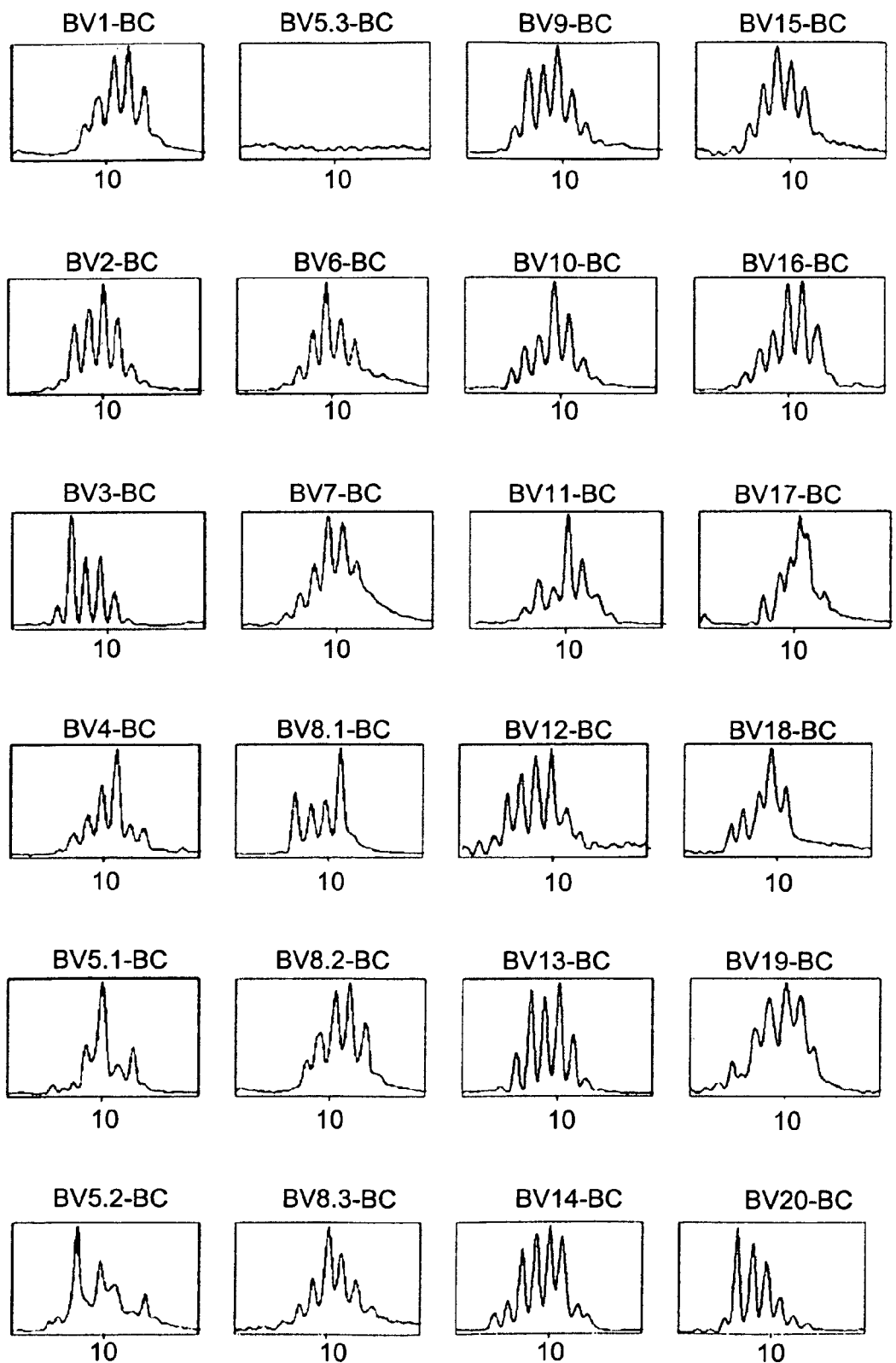

As the presence of a single MHC class I and single MHC class II molecule could diminish the size and diversity of the TCR repertoire, the expression of the various BV families and the CDR3 length diversity was studied as previously described (Cochet, M. et al., *Eur J Immunol* 22, 2639-2647 (1992)) by the RT-PCR-based immunoscope technique, on purified splenic CD4$^+$ or CD8$^+$ T cells. Peaks of significant magnitude with a Gaussian-like distribution were observed for most BV families (15 out of the 20 analyzed) in both CD8$^+$ (FIG. 2b) and CD4$^+$ (FIG. 2c) populations of T cells. Such profiles observed on peripheral T lymphocytes are typical of functionally rearranged BV segments with a 3 nucleotide length variation of the CDR3 subregions from one peak to the next (Cochet, M. et al., *Eur J Immunol* 22, 2639-2647 (1992)).

Absence of expansion (or profoundly altered profile) as observed for BV 5.3 and 17 were expected since these two BV segments are pseudogenes in C57BL/6 mice (Wade, T., Bill, J., Marrack, P. C., Palmer, E. & Kappler, J. W., *J Immunol* 141, 2165-2167 (1988)); Chou, H. S. et al., *Proc Natl Acad Sci USA* 84, 1992-1996 (1987). However, the altered profiles observed for BV5.1, 5.2 and 11 segments were due to a small subpopulation of corresponding BV-expressing T cells (they represent lower than 5% in C57BL/6 mice, and around 2% in HLA-DR1-transgenic H-2 class II-KO mice) (data not shown). Other than these instances, both CD4+ and CD8+ T cells in HLA-A2.1-/HLA-DR1-transgenic, H-2 class I-/class II-KO mice display, respectively, a pattern of TCR BV chain usage and CDR3 diversity, which is similar to that of non-transgenic C57BL/6 mice.

Example 4

Functional Characterization

Figure 5:
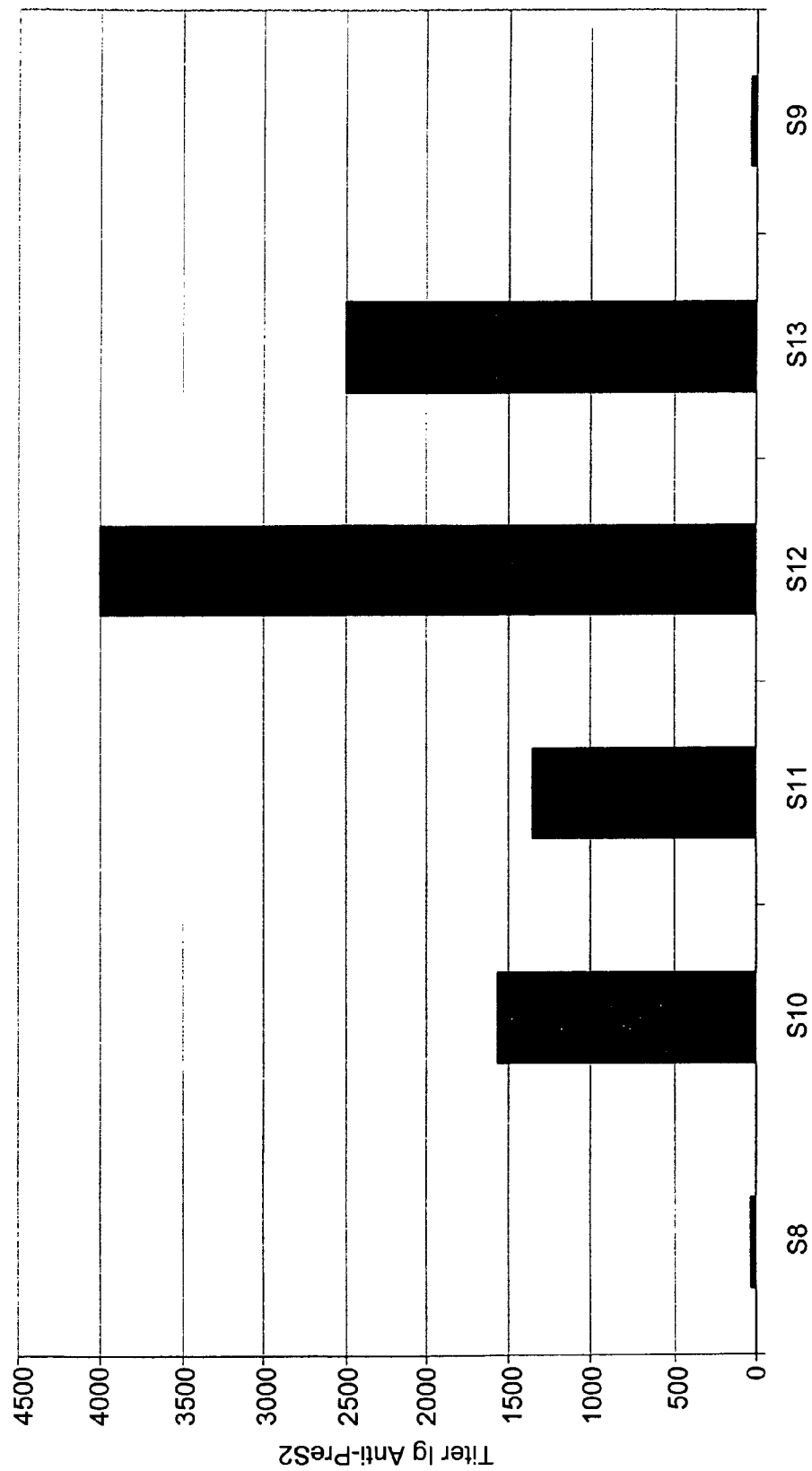
FIG. 5 shows the AC anti-Pre S2 response in HLA-A2+ DR1+CI–CII– mice following a pcmv S2/S immunization.
Figure 7:
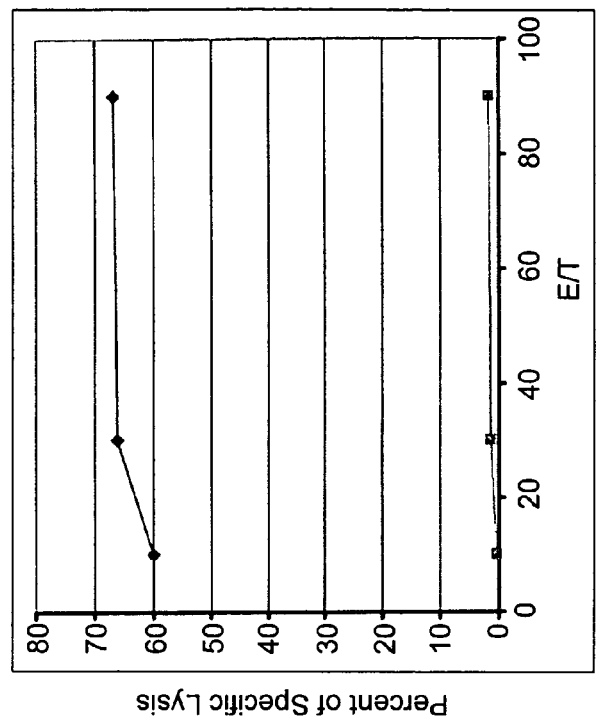
FIG. 7 shows the T CD8 cytotoxic response to the HLA-A2 restricted HBS (348-357) peptide following an immunization of HLA-A2+DR1+CI–CII– mice with pcmv S2/S.
Figure 7:
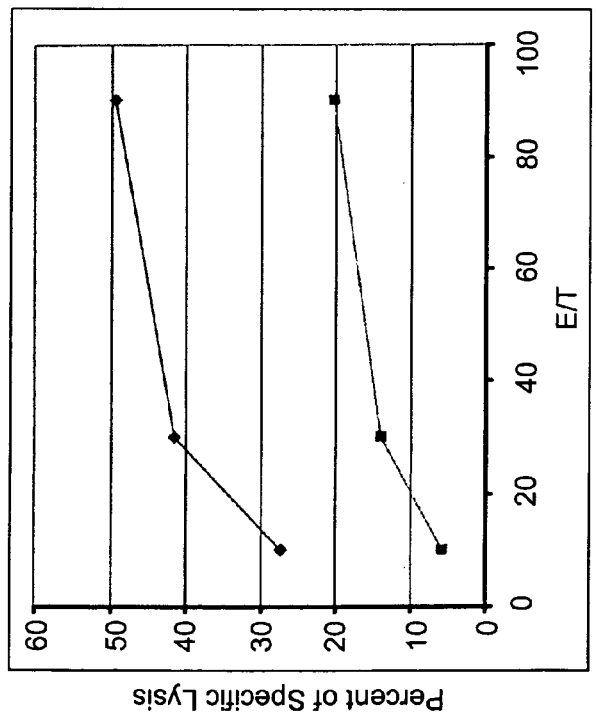

HLA-A2+HLA-DR1+β2m°IAβ° mice immunized with Ag HBs (hepatitis B envelope protein) were analyzed. FIG. 5 shows the specific humoral response, as indicated by the production of HBs S2 antibodies. FIG. 6 shows the specific DR1-restricted CD4+ T proliferation response of HBs$_{348-357}$. And FIG. 7 shows the specific HLA-A2-restricted CD8+ cytolytic T response of the HBs$_{348-357}$ or HBs$_{335-343}$.

These results show that the HLA-A2+HLA-DR1+ β2m°IAβ° mouse allows for simultaneous analysis of the specific humoral response, of the Ag-specific HLA-DR1-restricted response of CD4+ T helper cells, and of the cytolitic response of Ag-specific HLA-A2-restricted CD8+ T cells in an immunized individual.

Additional data obtained from these mice is provided in the following Tables 1-3.

TABLE 1

Proliferative responses of T CD4+ against HBV virus envelope HLA-DR1 epitopes from HLA-A2+DR1+H-2 CI-CII-transgenic mice injected with pcmv S2-S.

| Position | Amino Acid sequence | Responder/ tested mice | Stimulation index |
|---|---|---|---|
| 109-134 | MQWNSTTFHQTLQDPRVRGLY FPAGG (SEQ ID NO:16) | (12/12) | 3-4 |
| 200-214 | TSLNFLGGTTVCLGQ (SEQ ID NO:17) | (6/12) | 3-4 |
| 16/31 | QAGFFLLTRILTIPQS (SEQ ID NO:14) | (12/12) | 3-6 |
| 337/357 | SLLVPFVQWFVGLSPTVWLSV (SEQ ID NO:18) | (5/12) | 4-5 |

TABLE 2

Cytolytic response to HLA-A2+DR1+H-2 CI-CII-transgenic mice injected with pcmv S2-S.

| Position | Amino Acid sequence | Responder/ tested mice | Maximal lysis |
|---|---|---|---|
| 348-357 | GLSPTVWLSV (SEQ ID NO:11) | (12/12) | 20-70% |
| 335-343 | WLSLLVPVF (SEQ ID NO:12) | (4/12) | 30% |

TABLE 3

Anti-PreS2 Antibody response anti of HLA-A2+DR1+H-2 CI-CII transgenic mice injected with pcmv S2-S.

| Position | Amino Acid sequence | Responder/ tested mice |
|---|---|---|
| preS2 | MQWNSTTFHQTLQDPRVRGLYFPAGG | (9/12) |

Example 5

Immune Response to HBsAg-DNA-Vaccine

To evaluate the immunological potential of HLA-A2.1-/HLA-DR1-transgenic, H-2 class I-/class II-KO mice, and to compare their humoral, CD4+ and CD8+ T cell responses to those of humans, mice were immunized with an HBsAg-DNA plasmid. This plasmid encodes two hepatitis B virus envelope proteins (preS2/S middle and S/small) that self-assemble in particles carrying hepatitis B surface antigen. The currently used vaccine against hepatitis B comprises these two proteins.

Figure 3A:
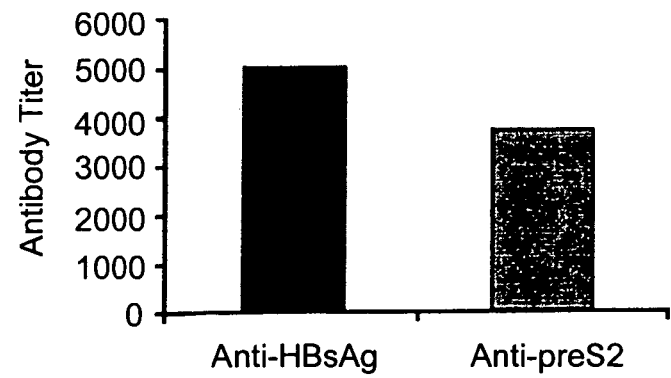
FIG. 3 shows HBs-specific antibody, cytolytic and proliferative responses. HLA-A2.1-/HLA-DR1-transgenic H-2 class I-/class II-KO mice were or not immunized by intramuscular injection of HBsAg-encoding plasmid-DNA and then individually tested. (a) Humoral (upper panel), cytolytic (middle panel) and proliferative (lower panel) responses and specificity controls of a representative HBsAg-DNA-immunized mouse. The antibody (IgG) titer against HBsAg particles containing both middle and small HBV envelope proteins and against the preS$_{210-134}$ peptide were determined in an ELISA assay. Cytolytic activity at different effector/target (E/T) ratios was assessed using RMAS-HHD target cells pulsed with either relevant (HBsAg$_{348-357}$, HLA-A2.1-restricted ♦) or control (HBsAg$_{371-378}$, H-2 $K^b$-restricted Δ, and MAGE-3$_{271-279}$, HLA-A2.1-restricted [ ]) peptide. Proliferative responses were detected using either relevant (HBsAg$_{180-195}$, HLA-DR1-restricted) or control (HBsAg$_{126-138}$, H-2 IA$^b$-restricted and HIV 1 Gag$_{263-278}$, HLA-DR1-restricted) peptide. (b) Similar evaluation of the antibody (IgG, upper panel), cytolytic (middle panel) and proliferative (lower panel) responses of 6 (1-6) HBsAg-DNA-immunized mice as compared to mean responses of 6 naive mice (0). Cytolytic activity at a 30/1 E/T ratio was assessed on RMAS-HHD target cells pulsed with either $HBsAg_{348\text{-}357}$, immunodominant (filled bars) or $HBsAg_{335\text{-}343}$, subdominant (grey bars) peptide.
Figure 3A:
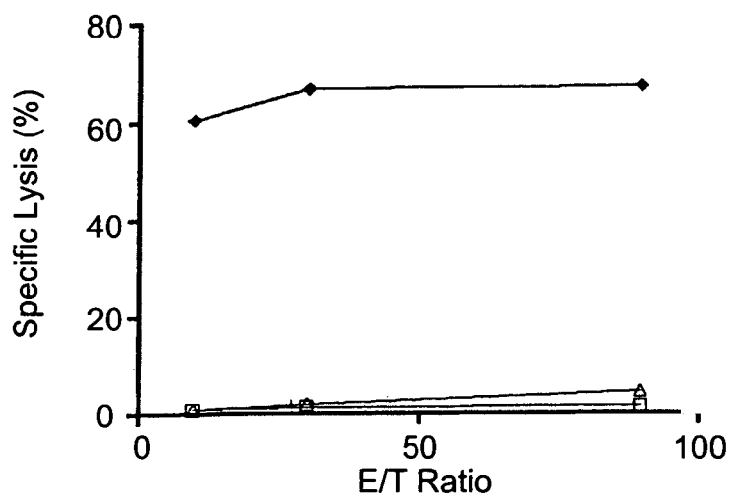
Figure 3A:
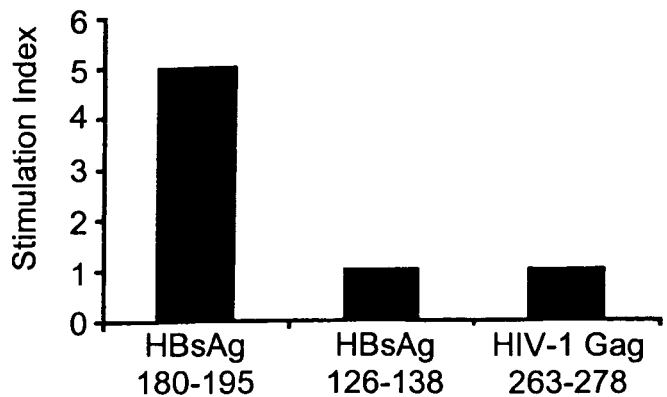

As illustrated in FIG. 3a for a representative mouse, HBsAg-specific antibodies were first detected at day 12 after injection of the HBsAg-DNA-vaccine (FIG. 3a, upper panel), and the titer of these antibodies increased up to day 24 (12 days after the second DNA immunization, data non shown). This early antibody response was specific for the preS2-B cell epitope (HBs$_{109-134}$) carried by the middle HBV envelope protein and for HBsAg particles, in agreement with a similar response reported in HBsAg-DNA-immunized mice (Michel, M. L. et al., *Proc Natl Acad Sci USA* 92, 5307-5311 (1995)) and in HBsAg vaccinated humans (Moulia-Pelat, J. P. et al., *Vaccine* 12, 499-502 (1994)).

The CD8+ CTL response to HBsAg was examined to determine whether the CD8+ T cells in the periphery of the HLA-A2.1-/HLA-DR1-transgenic, H-2 class I-/class II-KO mouse were functionally restricted by the transgenic human class I molecules. In HBV-infected HLA-A2.1+ humans, the immunodominant HLA-A2.1-restricted HBsAg-specific CTL response is directed at the HBsAg$_{348-357}$ (Maini, M. K. et al., *Gastroenterology* 117, 1386-1396 (1999)) and at the HBsAg$_{335-343}$ (Nayersina, R. et al., *J Immunol* 150, 4659-4671 (1993)) peptide (i.e., a multi-epitopic response is observed). In C57BL/6 mice, the H-2 K$^b$-restricted HBsAg-specific CTL response is directed at the HBsAg$_{371-378}$ peptide (Schirmbeck, R., Wild, J. & Reimann, J., *Eur J Immunol* 28, 4149-4161 (1998)). To evaluate whether the humanized mouse may respond as humans, splenic T cells were restimulated for 7 days, as described herein, with either relevant (HBsAg$_{348-357}$, HLA-A2.1-restricted), or control (HBsAg$_{371-378}$, H-2 K$^b$-restricted; MAGE-3$_{271-279}$, HLA-A2.1-restricted) peptide. FIG. 3a (middle panel) shows that HBsAg-DNA-immunization elicited a strong HBsAg$_{348-357}$-specific CTL response, but no response to either HBsAg$_{371-378}$ or the MAGE-3$_{271-279}$ peptide.

To determine whether the CD4+ T cells in the periphery of this HLA-A2.1-/HLA-DR1-transgenic, H-2 class I-/class II-KO mouse may be functionally restricted by the transgenic human class II molecules, the CD4+ T cell response to the HBsAg protein was examined. In HBsAg-vaccinated or HBV-infected HLA-DR1+ humans, an immunodominant HLA-DR1-restricted HBsAg-specific CD4+ T cell response is directed at the HBsAg$_{180-195}$ peptide (Mm, W. P. et al., *Hum Immunol* 46, 93-99 (1996)). In C57BL/6 mice, the H-2 IA$^b$-restricted HBsAg-specific CD4+ T cell response is directed at the HBsAg$_{126-138}$ peptide (Milich, D. R., *Semin Liver Dis* 11, 93-112(1991)). To compare the humanized mouse with humans and wild-type mice, splenic T cells were restimulated in vitro with either relevant (HBsAg$_{180-195}$, HLA-DR1-restricted) or control (HBsAg$_{126-138}$, H-2 IA$^b$-restricted; HIV 1 Gag$_{263-278}$, HLA-DR1-restricted) peptides. FIG. 3a (lower panel) shows a strong proliferative response directed against the HLA-DR1-restricted HBsAg$_{180-195}$ peptide, while the H-2 IA-restricted peptide was not efficient at stimulating a response, as expected. Similarly, no response was induced by the HIV 1 Gag$_{263-278}$ peptide. Moreover, an additional in vitro recall with the HBsAg$_{180-195}$ peptide increased several-fold the specific proliferative index (data not shown).

Figure 3B:
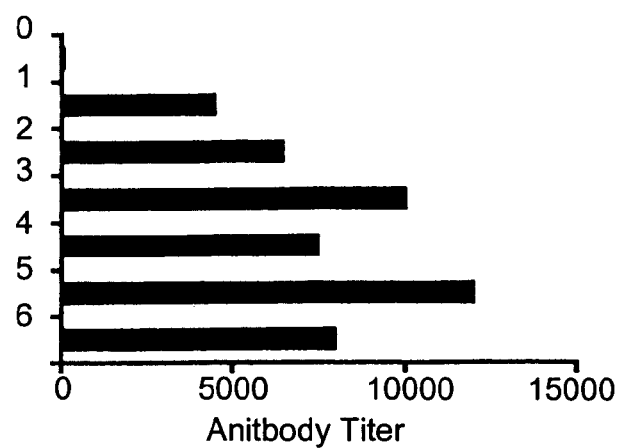
Figure 3B:
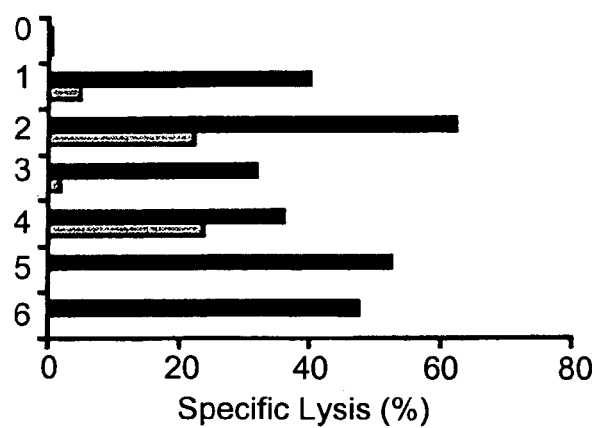
Figure 3B:
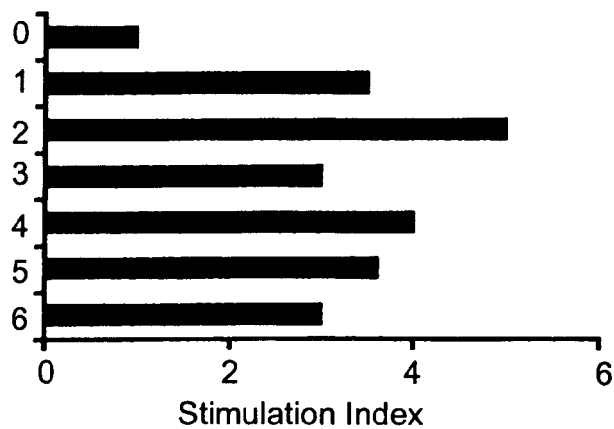

Having documented in a first HBsAg-DNA-immunized HLA-A2.1-/HLA-DR1-transgenic H-2 class I-/class II-KO mouse the development and the specificity of the HBsAg-specific antibody, proliferative and cytolytic T cell responses, 6 additional HBsAg-DNA-immunized and 6 naive control HLA-A2.1-/HLA-DR1-transgenic H-2 class I-/class II-KO mice were also tested individually for the same three responses. As illustrated in FIG. 3b, the three reponses were simultaneously documented in the 6 immunized animals tested and not in control naive mice. Interestingly, 2 immunized mice were able to develop CTL responses against both HBsAg$_{348-357}$ and HBsAg$_{335-343}$ HLA-A2.1 restricted peptides (FIG. 3b, middle panel).

Example 6

Protection Assays

The above examples document the induction of HBsAg-specific humoral, CD4$^+$ and CD8$^+$ T cell responses in HLA-A2.1-/HLA-DR1-transgenic, H-2 class I-/class II-KO mice, and show that they are directed at the same immunodominant epitopes as those of naturally-infected or HBsAg-vaccinated humans. This example tested whether these responses conferred protection to vaccinated animals. Since mice are not permissive to HBV, a HBsAg-recombinant vaccinia virus (rVV-HBsAg) was used for these experiments. Mice were immunized twice intramuscularly with 100 µg of HBsAg-DNA. Twelve days after the last immunization, mice were challenged intraperitoneally with 10$^7$ PFU of rVV-HBsAg. Four days later, virus titers were determined according to published methods and recorded as rVV PFU/ovary (Buller, R. M. & Wallace, G. D., Lab Anim Sci 35, 473-476 (1985)).

Figure 4:
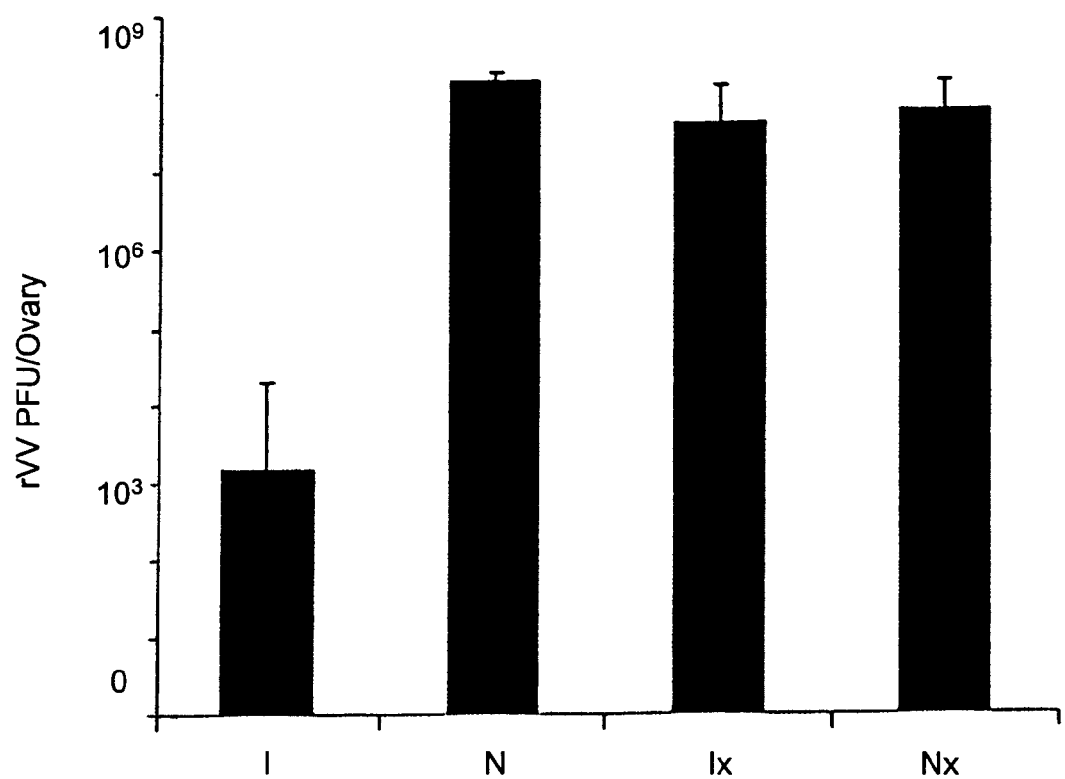
FIG. 4 shows results of protection assays. HLA-A2.1-/HLA-DR1-transgenic H-2 class I-/class II-/KO mice were or not immunized twice with plasmid DNA encoding HBsAg. Fifteen days after the last immunization, they were challenged intraperitoneally with $10^7$ PFU of rVV expressing either the HBsAg or the HBx protein. Four days later, animals were tested individually for viral titers in ovaries. The results (rVV PFU/ovary in log 10) are given for the HBsAg-DNA-immunized mice challenged with rVV-HBsAg (I, n=10), naive mice challenged with rVV-HBsAg (N, n=6), HBsAg-immune mice challenged with rVV-HBx (Ix, n=6) and naive mice challenged with rVV-HBx (Nx, n=6).

The results are illustrated in FIG. 4. Naive animals that had not been immunized with HBsAg-DNA showed evidence of rVV-HBsAg replication after challenge. In contrast, the virus titers in mice immunized with HBsAg-DNA were more than 4 orders of magnitude lower. These results strongly suggest that vaccination with HBsAg-DNA induced protective HBsAg-specific immune responses that controlled the infection with rVV-HBsAg.

The specificity of the protection conferred by HBsAg-DNA-vaccination was documented by challenging HBsAg-DNA-immunized mice with another HBx-recombinant VV (encoding hepatitis B x protein). No reduction of rVV-HBx replication was observed in HBsAg-DNA-immunized mice compared to unimmunized controls.

Example 7

HLA-DR1-Restricted CD4$^+$ T Cells Are Critical for Antibody and CTL Responses and Protection Against Viral Infection To evaluate whether HLA-DR1-restricted T helper lymphocytes contribute to antibody and CTL responses in the humanized mice, the immune response and the efficiency of viral infection were compared in single (HLA-A2.1) and double (HLA-A2.1/HLA-DR1) transgenic, H-2 class I-/class II-KO mice. As shown in Table 4, a potent HBsAg$_{348-357}$-specific CTL response was observed in HLA-A2.1-/HLA-DR1-double transgenic, H-2 class I-/class II-KO mice, but not in HLA-A2.1-single transgenic H-2 class I-/class II-KO mice. Furthermore, anti-HBs antibodies could not be detected in HBsAg-DNA-vaccinated HLA-A2.1- single transgenic H-2 class I-/class II-KO mice. As a consequence, HBsAg-DNA-immunized HLA-A2.1- single transgenic H-2 class I-/class II-KO mice were not protected against rVV-HBsAg infection.

TABLE 4

Table 4 Antibody, cytolytic, and proliferative responses of HBsAg-DNA-immunized mice, and protection against rVV-HBsAg-challenge

| | Mice | Specific Lysis (%) | | Proliferation (SI) | Antibody Titer | rVV-HBsAg PFU/ovary (log10) |
|---|---|---|---|---|---|---|
| | | 348-357 | 335-343 | 179-194 | | |
| A | 1 | 0 | 0 | 1 | 0 | $2.5 \cdot 10^8$ |
| | 2 | 0 | 0 | 1 | 0 | $2.5 \cdot 10^8$ |
| | 3 | 0 | 0 | 1 | 0 | $10^8$ |
| | 4 | 0 | 0 | 1 | 0 | $2.5 \cdot 10^8$ |
| | 5 | 0 | 0 | 1 | 0 | $10^8$ |
| | 6 | 0 | 0 | 1 | 0 | $1.5 \cdot 10^8$ |
| B | 1 | 30 | 15 | 4.7 | 2000 | $10^4$ |
| | 2 | 14 | 0 | 3.9 | 3000 | $3 \cdot 10^3$ |
| | 3 | 30 | 11 | 4 | 7500 | $4 \cdot 10^3$ |
| | 4 | 5 | 0 | 2.5 | 6500 | $7.5 \cdot 10^3$ |
| | 5 | 50 | 30 | 6.3 | 13000 | $7.5 \cdot 10^2$ |
| | 6 | 40 | 18 | 4 | 16000 | $5 \cdot 10^2$ |
| | 7 | 6 | 7 | 2.9 | 1500 | $2 \cdot 10^4$ |
| | 8 | 5 | 5 | 3 | 2500 | $1.5 \cdot 10^4$ |
| | 9 | 24 | 36 | 4.5 | 3000 | $<10^2$ |
| | 10 | 23 | 14 | 5 | 15000 | $5 \cdot 10^3$ |
| C | 1 | 0 | 0 | 1 | 0 | $10^8$ |
| | 2 | 0 | 0 | 1 | 0 | $2 \cdot 10^8$ |
| | 3 | 0 | 0 | 1 | 0 | $1.5 \cdot 10^8$ |
| | 4 | 0 | 0 | 1 | 0 | $10^8$ |
| | 5 | 0 | 0 | 1 | 0 | $2.5 \cdot 10^8$ |
| | 6 | 0 | 0 | 1 | 0 | $10^8$ |

Naive HLA-A2.1-/HLA-DR1-double transgenic H-2 class I-/class II-KO mice (A 1-6), HBsAg-DNA-immunized HLA-A2.1-HLA-DR1-double transgenic H-2 class I-/class II-KO mice (B 1-10) and HBsAg-DNA-immunized HLA-A2.1-single transgenic H-2 class I-/class II-KO mice (C 1-6) were challenged intraperitoneally with 10$^7$ PFU of rVV-HBsAg. Four days later, PFU per ovary, cytolytic and proliferative splenic T cell responses and serum antibody titers were assessed individually using either HBsAg348-$_{357}$, (immunodominant) or HBsAg$_{335-343}$ (subdominant), HLA-A2.1-restricted peptides-loaded RMAS-HHD target cells (E/T ratio 30/1) for cytolytic assays, HBsAg$_{179-194}$ HLA-DR1-restricted peptide for proliferation assays and preS2$_{109-134}$ peptide for the determination of antibody (IgG) titers.

The entire contents of all references, patents and published patent applications cited throughout this application are herein incorporated by reference in their entirety.

What is claimed is:

1. A transgenic mouse comprising:
   a) a disrupted H2 class I gene;
   b) a disrupted H2 class II gene;
   c) a functional HLA-A2 transgene; and
   d) a functional HLA-DR1 transgene,
   wherein the transgenic mouse has the genotype HLA-A2$^+$ HLA-DR1$^1$β2m°IAβ° and the phenotypes of (i) complete restriction by the HLA transgenes, and (ii) complete absence of immune responses restricted by the H2 genes.

2. The transgenic mouse according to claim 1, wherein the HLA-A2 transgene comprises the HLA-A2 sequence provided by SEQ ID NO: 1 and the HLA-DR1 transgene comprises the HLA-DR1 sequences provided by SEQ ID NOs: 2 and 3.

3. An isolated transgenic mouse cell comprising:
a) a disrupted H2 class I gene;
b) a disrupted H2 class II gene;
c) a functional HLA-A2 transgene; and
d) a functional HLA-DR1 transgene
wherein the transgenic mouse has the genotype HLA-A2$^+$ HLA-DR1$^+$β2m°IAβ° and the phenotypes of (i) complete restriction by HLA transgenes, and (ii) complete absence of immune responses restricted by the H2 genes.

4. The transgenic mouse cell according to claim 3, wherein the HLA-A2 transgene comprises the HLA-A2 sequence provided by SEQ ID NO:1 and the HLA-DR1 transgene comprises the HLA-DR1 sequences provided by SEQ ID NOs: 2 and 3.

* * * * *

SEQUENCE LISTING

<160> NUMBER OF SEQ ID NOS: 18

<210> SEQ ID NO 1
<211> LENGTH: 4547
<212> TYPE: DNA
<213> ORGANISM: Homo sapiens
<220> FEATURE:
<221> NAME/KEY: promoter
<222> LOCATION: (1)..(1205)
<223> OTHER INFORMATION: promoter HLA-A2 gene
<220> FEATURE:
<221> NAME/KEY: misc_feature
<222> LOCATION: (1206)..(1265)
<223> OTHER INFORMATION: leader sequence HLA-A2
<220> FEATURE:
<221> NAME/KEY: misc_feature
<222> LOCATION: (1266)..(1565)
<223> OTHER INFORMATION: human Beta2 microglobulin cDNA
<220> FEATURE:
<221> NAME/KEY: misc_feature
<222> LOCATION: (1566)..(1610)
<223> OTHER INFORMATION: GlySer linker
<220> FEATURE:
<221> NAME/KEY: misc_feature
<222> LOCATION: (1611)..(2440)
<223> OTHER INFORMATION: exon 2 and partial intron 3 from HLA-A2 gene
<220> FEATURE:
<221> NAME/KEY: misc_feature
<222> LOCATION: (2441)..(4547)
<223> OTHER INFORMATION: intron 3 partial-exon 4-exon 8-3'non codant
      gene

<400> SEQUENCE: 1

```
gaattcttag gtttaaatac attgttttat ggatttttaat acatccatct acagagccta      60
gcagggtgtc cttggcagtt gtcttttaat acctcatgtg ggtctgccta aaaactaatt     120
ttttatgtta atcaggttta aaaaatacta agtgttccta taaatatac acaacactta      180 gaagtggata cttcctaaaa acaggcagtg catgagcact agtgagggc attgtgagtg      240 cattgaacag ttgcaacttt gaggtgaata aagcctgtaa tcgcttctgg ttgcaacata     300
taggaacaca gtcgctactt tgtattgagg agatgtcctg gactcacaca gaaactcaga     360
gctatggaat gatggtaaat ttaaaatact acaaccagga gtcacagata cattgtctgg     420
gaaactgcaa cttagtagct ttgtgagtcc tgttgtaagg cttttggaca catttataca     480
tcaaggggct aaagtcacat ttttttaccta ttagattcct gatcattcag gggttaccaa    540
gattctgcta cccactgtag ttaataaaca aagagcaaat tggtctctat tctgtctcat     600
gcactcaggc gcaactcttc ccgattaaaa acaaaaacaa caacaacaaa aatctacacc     660
tccattccca gagcaagctt actctctggc accaaactcc atgggatgat tttttcttcta    720 gaagagtcca ggtggacagg taaggagtgg gagtcaggga gtccagttca gggacagaga     780
ttacgggata aaaagtgaaa ggagagggac ggggcccatg ccgagggttt ctcccttgtt     840
tctcagacag ctcttgggcc aagactcagg gagacattga cagagcgc ttggcacaga      900 agcagagggg tcagggcgaa gtcccagggc ccaggcgtg gctctcaggg tctcaggccc     960
cgaaggcggt gtatggattg gggagtccca gccttgggga ttccccaact ccgcagtttc    1020 ttttctcccct ctcccaacct atgtagggtc cttcttcctg gatactcacg acgcggaccc   1080
agttctcact cccattgggt gtcgggtttc cagagaagcc aatcagtgtc gtcgcggtcg    1140
cggttctaaa gtccgcacgc acccaccggg actcagattc tccccagacg ccgaggatgg    1200
ccgtcatggc gccccgaacc ctcgtcctgc tactctcggg ggctctggcc ctgacccaga    1260
```

```
cctgggcgat ccagcgtact ccaaagattc aggtttactc acgtcatcca gcagagaatg   1320
gaaagtcaaa tttcctgaat tgctatgtgt ctgggtttca tccatccgac attgaagttg   1380
acttactgaa gaatggagag agaattgaaa aagtggagca ttcagacttg tctttcagca   1440
aggactggtc tttctatctc ttgtactaca ctgaattcac ccccactgaa aaagatgagt   1500
atgcctgccg tgtgaaccat gtgactttgt cacagcccaa gatagttaag tgggatcgag   1560
acatgggagg tggcggatcc ggcggaggcg gctcgggtgg cggcggctct ggatctcact   1620
ccatgaggta tttcttcaca tccgtgtccc ggcccggccg cggggagccc cgcttcatcg   1680
cagtgggcta cgtggacgac acgcagttcg tgcggttcga cagcgacgcc gcgagccaga   1740
ggatggagcc gcgggcgccg tggatagagc aggagggtcc ggagtattgg acgggcgaga   1800
cacgaaaagt gaaggcccac tcacagactc accgagtgga cctggggacc ctgcgcggct   1860
actacaacca gagcgaggcc ggtgagtgac cccggcccgg ggcgcaggtc acgacctctc   1920 atccccacg gacgggccag gtcgcccaca gtctccgggt ccgagatccg ccccgaagcc   1980
gcgggacccc gagacccttg ccccgggaga ggcccaggcg cctttacccg gtttcatttt   2040
cagtttaggc caaaaatccc cccaggttgg tcggggcggg gcggggctcg ggggaccggg   2100
ctgaccgcgg ggtccgggcc aggttctcac accgtccaga ggatgtatgg ctgcgacgtg   2160
gggtcggact ggcgcttcct ccgcgggtac caccagtacg cctacgacgg caaggattac   2220
atcgccctga agaggacct gcgctcttgg accgcggcgg acatggcagc tcagaccacc   2280
aagcacaagt gggaggcggc ccatgtggcg gagcagttga gagcctacct ggagggcacg   2340
tgcgtggagt ggctccgcag atacctggag aacgggaagg agacgctgca gcgcacgggt   2400
accaggggcc acggggcgcc tccctgatcg cctgtagatc ctgtgtgaca tacctgtacc   2460
ttgtcctcca gagtcagggg ctgggagtca tttctctgg ctacagactt tgtgatggct   2520
gttcactcgg actgacagtt aacgttggtc agcaagatga ccacaatggt tgagtctcag   2580
tggtgggacc cttccagtag catatgcccc taattttgat atgaactcaa acagatatta   2640
aattacttat tttccattcc ctattccatt ctgtgactat ctctctcatg ctattgaaca   2700
tcacataagg atggccatgt tcacccactg gctcatgtgg attccctctt agcttctttg   2760
tcccaaaaga aaatgtgcag tcctgtgctg aggggaccag ctctgctttt ggtcactagt   2820
gcaatgacag tgtagtgtca aatagacaca tagttcactc tcatcattga tttaactgag   2880
tcttgtgtag atttcagttt gtcttgttaa ttgtggaatt tcttaaatct tcccacagaa   2940
ttccccaaag gcacatgtga cccatcaccc cagatctaaa ggtgaagtca ccctgaggtg   3000
ctgggccctg gcttctacc ctgctgacat caccctgacc tggcagttga atggggagga   3060
gctgacccag gacatggagc ttgtggagac caggcctgca gggggatggaa ccttccagaa   3120 gtgggcatct gtggtggtgc ctcttgggaa ggagcagaat tacacatgcc gtgtgtacca   3180
tgaggggctg cctgagcccc tcaccctgag atggggtaag gaggtgtgg gtgcagagct   3240 ggggtcaggg aaagctggag ccctctgcag accctgagct ggtcagggat gagagctggg   3300
gtcataaccc tcaccttcat ttcctgtacc tgtccttccc agagcctcct ccgtccactg   3360
actcttacat ggtgatcgtt gctgttctgg gtgtccttgg agctatggcc atcattggag   3420
ctgtggtggc ttttgtgatg aagagaagga gaaacacagg taagaaaggg cagggtctga   3480
gttttctctc agcctccttt agaagtgtgc tctgctcatt aatgggaac acagccacac   3540 cccacattgc tactgtctct aactgggtct gctgtcagtt ctgggaattt ccagtgtcaa   3600
gatcttcctt gaactctcac agcttttctt ttcacaggtg gaaaaggagg ggactatgct   3660
```

-continued

```
ctggctccag gttagtgtgg ggacaggatc gtctggggga cattggagtg aagttggaga    3720
tgatgggagc tctgggaatc cataatagct cctccagaga aatcttctag gggcctgagt    3780
tgtgccatga agtgaataca ttcatgtaca tatgcatata catttgtttt gttttaccct    3840
aggctcccag agctctgaaa tgtctctccg agattgtaaa ggtgacactc tagggtctga    3900
ttggggaggg gcaatgtgga catgattggg tttcagggac tcccagaatc tcctgagagt    3960
gagtggtggg ttgctggaat gttgtcttca cagtgatggt tcatgactct cattctctag    4020
cgtgaagaca gctgcctgga ctgtactgag tgacagacga tgtgttcagg tctctcctgt    4080
gacatccaga gccctcagtt ctctttacac aacattgtct gatgttccct gtgagcttgg    4140
gttcagtgtg aagaactgtg gagcccagcc tgccctgcac accaggaccc tatccctgca    4200
ctgccctgtg ttcccttcca tagccaacct tgctgctcca gccaaacact gggggacatc    4260
tgcatcctgt aagctccatg ctaccctgag ctgcagctcc tcacttccac actgagaata    4320
ataatttgaa tgtgggtggc tggagagatg gctcagcgct gactgctctt ccaaaggtcc    4380
tgagttcaaa tcccagcaac cacatggtgg ctcacaacca tctgtaatgg gatctaacac    4440
cctcttctgc agtgtctgaa gacagctaca gtgtacttac atataataat aaataagtct    4500
ttaaaaaata atttgaaagt gacccttgat tgttaacatc ttgatct                  4547
```

```
<210> SEQ ID NO 2
<211> LENGTH: 29133
<212> TYPE: DNA
<213> ORGANISM: Homo sapiens
<220> FEATURE:
<221> NAME/KEY: promoter
<222> LOCATION: (1)..(15279)
<223> OTHER INFORMATION: promoter 5' from HLA-DR alpha gene (HLA-DRA
      gene)
<220> FEATURE:
<221> NAME/KEY: gene
<222> LOCATION: (1)..(29133)
<223> OTHER INFORMATION: HLA-DR alpha gene (HLA-DRA gene)
<220> FEATURE:
<221> NAME/KEY: misc_feature
<222> LOCATION: (15280)..(15425)
<223> OTHER INFORMATION: exon 1
<220> FEATURE:
<221> NAME/KEY: misc_feature
<222> LOCATION: (15344)..(15346)
<223> OTHER INFORMATION: ATG start
<220> FEATURE:
<221> NAME/KEY: misc_feature
<222> LOCATION: (17838)..(18083)
<223> OTHER INFORMATION: exon 2
<220> FEATURE:
<221> NAME/KEY: misc_feature
<222> LOCATION: (18575)..(18866)
<223> OTHER INFORMATION: exon 3
<220> FEATURE:
<221> NAME/KEY: misc_feature
<222> LOCATION: (19146)..(19311)
<223> OTHER INFORMATION: exon 4
<220> FEATURE:
<221> NAME/KEY: misc_feature
<222> LOCATION: (20008)..(20340)
<223> OTHER INFORMATION: exon 5

<400> SEQUENCE: 2
```

```
aaaaaattaa gtatataaag tttaaaaagt tagagtaagc taaggttaat tattgtagaa      60
aaacattttt cataaattta atgttgtctt agttacagta tttataaagt ctacagtaat     120
gtatagtaat gccttaggcc ctcgcattca ctcaccactc actcactgac tcatcagggc     180
aacttccagt cctgcaagct ccattcatgg taagtgtcct agaaagatct accatttaaa     240
```

-continued

```
aatctttcat atggtatttt caccacacct tttgtatgtt tagatacata aacagttagc    300
attgtgttac aattaccaat agtattcaat acagtcacat gctgtacagg tttgtcgcct    360
aggggtaata gggtgtacca tatagcctaa atgtatagta ggctataaca tctagtttgc    420
gtaaggacac tctgtgatgt tcacacaaag atgaaatcac ctaatgacac atttcttaga    480
gcttgtccct ttagctaagt gatgcatgac ttcagttttg ccccatttct agagcatagt    540
cctcaatgac tttcaatgaa aaacccgata gctttcatct tctcaatcct gaagagctga    600
aggagattta ggctgaactt aaagaaattt tcagcttagc tcattagtct tctactccat    660
acatcttcaa catttaacaa gtgttttgaa aaagacacct acaaagtgct tgaagtcatc    720
aactctcaaa tcttgtcatt gcagcaccac gtcaaatgac aaaacacttg ctattttctt    780
agtccactgg aggagcctat tgtcagaggc caaacctgga ttattagctc caaacaagca    840
ctcagatcag taagtgtcct caggtgataa gtggttgttg ctacttggca tcaattcacc    900
agttcttctg aaacttacgt ctgttttgtt ttagggccct tatcaatggt aggtctttgt    960
ttcctcaaca ccactggaca gtgaaagatt ttgcactgcc tttcagaagt tgacactta    1020
gttttttgtt ttaccttcta ccgtagcatc agaagttaac caacgtgttt tgaagaaacc    1080
agagtgtttg agatgcctca gttttctagt tacatcacac tggccccata attgctgctg    1140
atttctttct tacagcagaa aactgtagga aaattgtagc agaaaacttt tctacagcag    1200
aaaacggtag cagaaaaatg gcactaaaac gcagcgtaca cttgcaaaca gcaaatgcta    1260
ccaagagaaa cagtgatgtc caaacgtcag cttacatttg catggttctt ctttggaatt    1320
tttattcatc tagtcctatt tactttctta gctaaacaat gctttttaaa aatataccat    1380
taaaatttta tccatttttt gtagttgttg ccagtgggac aatttgtcct actgtgaccc    1440
taatgcatct tatactgtgg tggaaaaaag aataagattt taaattgtgc tttctgaaaa    1500
actggatata gaaacagaca atggccagac catatataaa aataggcctg gctgggcacg    1560
gtggctcacg cctgtaatcc cagcactttg ggaggccaag gcggatggat catgaggtca    1620
agagatcgag accatcctgg ccaacatggt gaaacccctg cctctactaa aaatacaaat    1680
ttagctgggc atggtggcgc gcagctgtag tcccagctac tcgggaggct gaggcaggaa    1740
aatcacttga gccaggagg tggaggttgc agtgagctga gatcgtgcca ctgcactcca    1800
gcctggcgac agagcaagac tccatctaag aaaaaaaaaa aaaaaataga cctttgaccc    1860
acagcctaca gcagcctgcc tggggaacca attcccttat cttcaataaa caatccagca    1920
aggtagtctg cttaagtccg acttgcagga agtcagattg ctgtctctag taacaatcca    1980
ggaggctaaa taataacttt tataacaatt gttttaaaat ggccaggact tgattaataa    2040
ctgacagttc ccccaatatt tgtgcctgct tccaacttag gaccaaccag ggaaagctaa    2100
atatgcatcc tacccaatta cataggatac tccacttcta gttacccctt aagcattccc    2160
catgccaaca gcctccaatc aggtcctttt taaccactat aaagtttcct acttctttgc    2220
ctgtctttga gtctctgcca aaatgcaaaa gatggtggct gactcctttg ttatagcaat    2280
ttgtgaataa ttttttgctct tttcatttgg ttgatcttca tgtatttca cattattaag    2340
ctttatataa attaaaatcc aagaggctaa catttaatta atgacattta agatcttcta    2400
tatcggataa tgctatacat tatattaggt ttaatatttc tattaaatat agattagta    2460
aattactaaa aatgctaaaa attcatcaaa tatatatgta agtacaaata aggaaaatgc    2520
aaagagagat attagaaagg ggtaatatat tcaggaataa atattcaaga tattttaagt    2580
```

-continued

```
tggagatatt gtctgttggt actaaatcaa tttccccctg ttttgtgctt ttttccatat    2640
cacttggggt tgaagcctgg acaccacttc ttccagagtc cctttcttag gaaggcactc    2700
acttgcgatt agaaggcagt ggaaaattgc tgtcattctg cttctgacag caagtagcag    2760
cagctgccag gagtgtgggt tgtttagtg ctgcagggcc aatagtagct tcctgcagtt     2820
cctgaccttt ggaagcacaa ttttgctttt tctgtcctta caaaacttttt gcaatgcact   2880 tcactgtatt acatctctct gggcttaaaa taccttgagt gtgttttttc cccettgtaa    2940 atctgggcta gactgaataa tcttgtaagt atgtaaatat aagcaactat tttaaaataa    3000
cctgggtttt taaatgtaat acagatgctc ttcaacttat gatggggtta actcccaata   3060
aatccagtgt aaattgaaaa tattgtgagt tgaaagtgta gagtataagt tgttcacctt    3120
catgatcatg tggctgaggc tgcctggcat tgtgaaagag tatcttactg agtatcgctg    3180
gtctggaata agatcaaaat ttaaagtatg gtttatacag aatggatatt gcttttacac    3240
cattgaaaag tcaaaaattc ctaagtcaaa ccatcttaag tcaggtgtgt ctgtagtttt    3300
aaaaaaatta caaataaaga atatccagtg ttgttgggag tgcagagaag atttacaagg    3360
taaacattga tttgtttaaa gtttgagaga aaaaattaga taatatgctt tatgattttt    3420
aaatgttaat ttcaaagtaa ttatacattc acaggagttg atgaaaatag tacagagagg    3480
tcccttgtac ccttcaccca gtttccccca atggttacat catacataac tatagcacaa    3540
tatcgaaaca aggaaatcga cactgataca atgtatttgc agttttctac tttatcacat    3600
gtgtagattc atgtaaccac cactgtgatc aaaatacaga actatattcc atcaccacaa    3660
agatcttcct catgccactc gccctcctta agagtcacac cattcccccca cccccaccat   3720 ccctacactg tgccaaccac taatttgatt ttcatctgta taatttatc atttagaaaa     3780 tgttatataa atggaattat actatatgtg accttccgag actggcattt tgtactcaga    3840
ataatgccct tgggatctgt attaggtgct ccagagcgt tgtactaaca ggatatgtat     3900
atatagaaag atatttcttt taaagaattt gctcacatga ttgtggaagc ttactgagtc    3960
caaattctga tggaagaggc cagcagtgga ggagactggg acagagttgc agtttgagcc    4020
caaaggtagt ctgctgtgga accaggaaga gccaggattg cagatggagt ctgaggcaat    4080
ctgttggaga gttccctctt atgctagtca ggcattcaac tgattaaatg aggggaaccc    4140
agttatggag ggcaatgtac tttacttaaa atctactgac ttaaatatgt aactctcacc    4200
ccaaaactgc cagattatgt gaaattccat gtcctctact tggctccatt gacactcaga    4260
tggagtagat taaacaacag acatttactg aaagtcctca cttaacatca tcaataggtt    4320
cttagaagct gtgactttaa gcaaaatgac atataataaa actaatttga ccataggcta    4380
attcagcgat ccccaacatt tttggcacca gggactggtt ttgtggaaga aaattttgcc    4440
atggatgggg gttggggact agcggtggca gggagtggga tggcacaacc tagatccctc    4500
gcatgggcag tccacaatac agttcacaaa ggtttgcact cctgtgagaa tccaatgcct    4560
ctgccgatct gacagcaggc cattagtggt ctgtggccca ggggttggga acccctgggc    4620
taattgatgc gaacaagatt taagttccta tggcttattt ctggtcacaa acacatcacc    4680
aaactcctaa ataaagactc agaacacttc taatattaaa cattaaaata aatgggaact    4740
atatatacat ttaaggtagg tttataataa caagtaagat aattaattat ccagtttttg    4800
gtgaattagt gagtgatggt ggtcacagtg gtggtgggtt acattaagga acaaatgttt    4860
gtaaaatgaa aatggtaagg agcacctcct gccaccacac agctcaaacg caaagaagaa    4920
caaatacgtt gaactcactg agtactttg taccccattg tttactattg tacagttgta    4980
```

-continued

```
tgaatatcat gtactttaca aattttatt ttagaaacat ttctattcat tcgcttattc      5040
attttccaac ctgcttattc cagttcaagg tcatggatga ctggagccta tcccggcagc      5100
tcaaggacaa gagaggaacc aaccttgtat aggatgccat cccatccatt gtgggatgca      5160
gacacacaca cacatacaca cacacacaca cacacacaca aagtcactct gctgggacaa      5220
tttagactca ccaattaacc taacatgcat gtctttggga tgtgggataa aactcaaata      5280
cacaaagaaa acccatgcgg acgtggggag aacacacaaa ctcctcatgg ccagtggccc      5340
tggccaggaa cctatttatt ttctcaccaa cattgtaaca aaacgttgaa caaaacaatg      5400
ctataggagg accctctgtg tttctcacag tcctggaggc tgggaagtcc aagatcaaga      5460
tgctgacagg ttcaattcct ggtgaactta aactgaagg ctctctggca ggggtgcctt       5520
gtggctgcag gctgggtata gaaactcagg ctccccacta ggcctccact tacagaatcc      5580
tgactgggag ggagagggtc tcatcagcgc tcccacatgg cctctactga caccaggaag      5640
ggagaagtgc ctccttacac ctggacagtg gtgaaagtcc cagctttcta cttggcctcc      5700
tctgacaaca ccttggcaaa gtgggtgagg agtgcttcct tgcaacaggg caggtggaag      5760
tccaggctct tcacatgggc ttcactaaca ccacagtgtg gaggtggctg attactgata      5820
ggcaggggca aaagtcctag gtccccagtt ggcttcctct gacataagcc tgatgggtct      5880
aggtagtgtc tcattatcgc caggcaatgg gataagacaa agctcctcac tcagtgtttg      5940
ctgactgagg cgggatggaa gcccctgatt tttctgtatt tgactggagt agtgcggtta      6000
ctgtcagtta tctgcctggt aggctgctct ttcttgttcc cttggataga gaaacatgct      6060
ttccttagga tattttttgtc tgtgactact gatgtttcct gttttccagt ttctccagca     6120
ctcattcctg gatatattag gcagaaagaa gacctatgaa actcaccact ctgtcattcc      6180
ccaatcccat ggtctgaggc caacctgctt ctcctctcca tcattcaagg cttttttatg     6240
tctgtctgta gctgtactta gcaggaagaa taggaagaat tgtacctact tcatcttgtc      6300
ttagaaccag aaatctctca ccatattttt taaaatatgt ttttgtcata tattaaaata      6360
ttatacatct atccttagat ccttaaataa acatataatc tatccttaga gttaagttaa      6420
tttggtaaca aaaataaaac aagactaaaa ctattaattg tgttaaagcc ataaaaaata      6480
tgcaaatttt tgcccaaaat atgggaaatg tgcgtgtgtg tgtgtgtatc tcctatgtat      6540
acacataaaa aaagacataa aatgaaaatt gctgatgtat caataccccgg gggcagggag     6600 tattctcagg tttaactaag tactcatatt caagttttta ccataggcca cacctggctc      6660
tcagattcac ttagaaggat attagacagg agtcaaagta tgccaaagtg ctgaatcagg      6720 tcttttttctt cagtgggaga agttcttgaa acagttcata atttattcca ggtgctagtt     6780
tcatcctctg cccccatccc ccaagtgaca actcaggtac aaggagctga atttacacct      6840
gtggaagttg tgtccaccgt agcttagaat cctcatgtca tctacgagct agtacctctt      6900
ataacaaacc catgggcaca gcttccagag tccccgtaaa gggcatgctc agttacaagg      6960
gtcactgcat ttggaaatac ccaaactatg ggtccccgtc atttgttacg gttcatgaaa      7020
tattcttccc agtaaagata caaaatgcca accagaagcc atttgtgcca taagcaatgt      7080
tgtctaaaaa tccagctgac attcttcctc catcaggttt ccagaaaaca gctagaaaat     7140
tagcctaaga ttaaatacat catggagaag tagaaagggt gttataaagc atttatccac      7200
aagattcaaa atgaaataca gttaattttg tccgttttaa gacattattt caaccttcaa      7260
attatttaaa agaagtacat cctatatttt gtgtgcttat tcaaaaaagg catggtaata      7320
```

```
cttataaaaa gactttaaat attttttataa gttttaaata ttttataagt aattttataa    7380
atgaaattac aaaccattta agtgacctaa ttaaatcaaa cacactttga gtatgcacac    7440
aagaaaaaaa ttagttgaag catcctgact taagaaatcc ttgatctttc ataaggtgtc    7500
tgaatactca atgtcaaaaa cacttatgaa gaattaaaca ctgttgacca caagagggaa    7560
acctagtccc agttatacta taaattagaa aatcaaggga aaaatatgtg tcctgagaac    7620
ttttgaaata gtcacatata aacatagtat acaagaaaaa accaaccgtc atccctaccc    7680
aaggatatgt ttgtggtatg agtggtttta gtgttttgag tggactggtt cttggactcc    7740
acatattatt ggctacagag atagagactt gatttagaaa atcacagttg ccactttcta    7800
agtaagccct tgaccaaaag actagatttc tttaaaccca gttttctcag gtaaaatgga    7860
aatacaacta ttatctaata aatataagta agctttagtg tcatagtcat agcagtagta    7920
ttttcaattg gtaaaaagaa actggacccc aaaaaagaat tcagtgaaaa gcagtaacag    7980
tcttctggca tatttctcac ctttctttct accttaaagg ttcaaagttc ctaagtaatc    8040
tcagaaacct aaaatagttt attctctatc ctcactattg gttttaaaa acatttttgc    8100
agcatggacc actgctcatg tacagatgct ctccaactta acaataggt tatgtcccaa    8160
taaacccatt ataacttgaa aatatcttaa gctgaaaatg catttaatac accaataaac    8220
ccatcataaa gttgaacaat cataagccaa attataagtc agagaccatc tgtattagct    8280
taagtcttgg aatggtttat ttttagatg ccatttagcc acttatattc tcttctattt    8340
tattgtgaga actaattccc ctcttacatt ctgtgcttga cccatgctat acttagtgtg    8400
aacaagagcc accttcttct catgacttct attttttgt gaaaatttcc ttcactcatt    8460
cacgacattt ggatttgaaa tcttacctac ttaagtactt taaaaaatca ttttctacca    8520
tctttcttat caggagcctc tagtgattcc ttctccacac ttctaacttc tcatcttcac    8580
actccttgtc ttcctaactt cactacagta agtgttttac atgtttagaa ctcagctcct    8640
ttactatgat tgctaaccat gtaccttaaa taaaccgtct tctagttttt tgtttcttac    8700
tctcaattat accttttaga aaagaattaa gagtagaaaa agactgctac atagacattc    8760
ttatgatctt cagaaatgag cacagatcat gcttaatgaa aaaagatttc caaataatgc    8820
tgcatatgtc cagagaaaag gtggcagaaa tgactgtcgt ttgggggcac tattgtctgg    8880
acatggccag ttctcagaac tccagtccct aaattccctt ctaactaaag gaaaagcctc    8940
ttaagggtct tatagaaatc ctgccacttt cacctgaaag aataatcttc agttatgtgg    9000
cacatggcca agagtaaaag tctttagtca cttggaagca gacagacact gtaatgctaa    9060
ataattggac ataacatgga acttactgag gcctcaaata tcaatttta ctttgggaaaa    9120
agagcagcaa ctttaaaagt gattgaaagt aactcaagtt tattccttaa cagagtgatg    9180
cttaatctaa caaaaaacat gttatatgca cactcttctc cattaccttg taagaaaact    9240
ggactaggaa acacagctga aatggccagt tctgcctcca tttcctaaac cgtgttataa    9300
ttatgtctat gtgaccagta acagacaatg accatgattt atacttttc atatgtttgt    9360
tgttttgttt tcaatgtttg tggtctttcc tcagtatcag ctaagaggcc attaacacag    9420
atatctattt atggacatgc gagactgttg ttcacctctt ttgcagaatt cataaagaaa    9480
tgatggggaa aacacatcaa agatagagtg ataaagcaa atgtgccaca tatacaccat    9540
ggaatactat gcagccatga aaagaatga gttcatgtcc tttgcaggga catggatgaa    9600
gctggaaacc atcattctca gcaaaataac acaggaacag aaaaccaaac actgaatttt    9660
ctcactcata agtgggagtt gaacaatgag aacacatgga cacaggggcc tgttgggggg    9720
```

```
gtgggggca   aggggaggag   agcattagga   caaatacca   gtgcttgagg   agcttaaaac    9780
ctagatgacg   ggttgatggg   agcagaaaac   caccacggca   catgtatacc   tatgtaacaa    9840
acctgcatgt   tctgcacatg   tatcccagaa   cttaaagtag   aataaaataa   ataagtaaat    9900
aaggaatgat   gggacaaaca   agtttctgtt   attgtctctc   tactgaccaa   agggtggtca    9960
gagagtatag   gatgaagcag   atttgtgata   tccttgaata   gatctgctct   ttactatgaa   10020
ttctatcatc   tactcccagc   gtatgtggga   aagggaccaa   cttacttgcc   tggaatttag   10080
tgaaattgtt   ttctagggggg  accaagagtt   tcctctactt   gatatgaagt   tgggtggttg   10140
aagatgatag   gattggcttc   tgcttccatc   agaatcctaa   agggcagggt   atatggacta   10200
gttggtattg   gatcttggaa   actgtgatgc   attgggaatg   gtcacactcc   cagagtttgt   10260
ggacacaaag   aatgttttag   tgttccctac   acaccagaca   cgggccatga   aggaatctga   10320
agagcctacc   aaaccttgca   caagagaaaa   gctttacttg   gaacatcatc   caggctcaga   10380
gaacacaaat   atttcatttc   cagtaagacg   tttctggtct   ttttctcttc   ctcccttcc    10440
ctgaacctac   cctagatgag   ctatggcctc   aaagtgccag   tagaacgtaa   gaaggaagga   10500
gaaccacact   cattcctgcc   ttcaacaatt   tacacaggga   tagaaagaga   tttatattaa   10560
atcaagttgg   gactttcaat   tattatatag   taccaaacaa   tctaattgct   gaactaagat   10620
atacttgtgc   aatttaaggg   aattgtagaa   tagcatatta   attagaatca   agaaaataat   10680
tcatgaagta   tgctataatt   cctacccaag   cgcaggggaa   tagcatctct   aatgaaattc   10740
tctaaagagg   caagagcagg   cacaatgagt   ttttgtttga   ttaaagattc   catttagtgc   10800
ttatccaacc   tagcaattac   atttgtatgc   ttcagatgtt   tttaaaaaaa   taaacaaaag   10860
aaagtacctt   aaataaagaa   taggatcaaa   tagtatttaa   acaattgagt   aaattaaaaa   10920
attatatgaa   ttagattgat   tgaaattgat   actttcctaa   ttctcctcct   tcaacacaca   10980
gacacacaca   cacacacaca   cacacacaca   cacgtatgca   tacaaacaca   tctgaattct   11040
ataaaatcat   tctgaccttg   atgagattcc   atagtttact   catgcaacag   aacataatgt   11100
ctaaatgaag   tttctggtct   ctgttttaca   tggatgattg   agtaaaatca   ttccctattc   11160
ctggaagaat   agctaagaaa   ggattcacag   gtgaggacat   gcgttttttc   agaagatgag   11220
aacaaagatg   agaagatgag   agcaacagaa   tgtcctatat   cctaatgctc   tgtgctgact   11280
tcggagtggc   caatatgata   gagatggaag   gaactctgaa   aacaaattgc   cagaatttct   11340
aaggaacagg   atgttgag    tgagtgaatc   aagccatgga   ctggctgtat   gggggcagct   11400
attagagaca   actacccta   gacttctttg   gtgattggtc   aagctaatct   tttccttcag   11460
agtctctcaa   ttataagact   tagcttgtgc   catttagaac   agacaagaac   acagagaatt   11520
atagaacaat   ctgactacag   gttcttaagt   tatagcaatg   aaacttgtag   ttggccggca   11580
ggaaaatatt   ctgagatgtg   gattcaaagt   ttctaagtgt   gcacacgtac   acacacacac   11640
ccctacctgc   atgcgttttc   taatttacaa   agactactca   agtaaagagg   ggtaatttca   11700
cacccagga   ggtctgtata   aagataactc   tggtctttaa   agcatcgggt   ttcaggtaga   11760
ggtgaagaga   gaatgaatca   aactcaaact   gccatcctcc   caggttaaag   atgagtccag   11820
tcattgtgga   gccctctatt   aacacaggac   atgctaggaa   ggcccattaa   cccactgccc   11880
tagcacattt   gttaacgtcc   tagtgcattt   gttgatatca   acagttcaca   gttttattc    11940
tgatagggat   ctattccagc   agaccagctt   ctgtgacctc   tcaggatgcg   aaaaagtaac   12000
acaagaaaag   cttcttatgt   agtgaattga   gaaggaaata   cctagatcaa   tattccctca   12060
```

```
gcacctctgg taggaagtcc ttagtaggag aaaaacacca tgaagaccct tagtgcagaa    12120
ggaaaagggg gtaggggggtg gtggaaggga agctaaaaga aggggctgga ggttctcaga    12180 attcaaaccca cacaaacaaa tgaagtattg aggtcccaga cttgatctgg gcccagtgtg    12240
aaagccctaa cttatttctc cagaagaata tgtcctctgg ttttagactt ggcactgtgg    12300
ggagaaccag agtgatctat ggtggatata cacacaaaca tagacacaca tatttgcatt    12360
tagtaatttt tgtaaaattt ccatttgctt ctctgatcct gtctgtatct ttgggaatag    12420
atgtaagaat attacatctc tcaggcttgc tctgccccag gtttctgaac gtggaataca    12480
tttctccagg gaaactcagt attatgagat ttgggaggtg gaagttaggc cacagccatc    12540
tcagggacag gtttcacaga catgagtttt ggcagcagcc ttgtgttcta aagacattta    12600
ctcctagggg ctctagagga tctgcaacat cagcagaggc ttcctgtggg ttcctgatct    12660
tttaaaatta gggttctgca gtgacttctg ctcctccaga ccccctaaca gttttaaggg    12720
ctaattccct gtaatatatt cagttctgct tagactgatt acagggattc ctatttcttg    12780
actgaattct catggctata gtggctcgtc accatttgac atcaccaaga agtcctcatt    12840
caggtgcctt tggaaattcc ctcaaacaca caggaaatta gagtttgaaa gaaaacggag    12900
aaccatgagc actgtccaaa taggaacttc tctcctatca cagagaaagg gaactgaaag    12960
tcatttctca agtctcccaa atttagtaat ctcacaagaa gaaccaatca gtgttctagg    13020
actaaacagt gtcataagtt gctgagcaac aacttggatt gaagatgcta ttataatata    13080
tgaaatgtct ttgaatttac catgtttttc tcaagcacca tttaagaaca aggcattatg    13140
gcagccagca aagggcagac atagaaaatt atacatggtt ttgcctctaa aagaggagat    13200
gacaagctta aatcatagga tcagactctt agcacagact gataccatag gctctcatct    13260
ggcccattct cctgactctt tacctttcag gaaaggtatt cctgaaaaat tgcaggagag    13320
accatgctgt aggtctcttt ctagcgatct aggagttaat gccacagtgt gttcaaagcc    13380
ctttgatgcg atcagataat cagtaatgta tggaatattt gtgttcataa cttgtgagaa    13440
cggctgcatg gcaggacaag acccccagcac aacagtatgg aaaatccacc ctaagcagac    13500
atgtcatgac tgatgttgaa caatggactc accagccagg cacggtggct catgcctgta    13560
atcccagcac tttgggaggc agaagcaggc agatcacgag gtcaggagat caaaaccatc    13620
ctggttaaca tggtgcaacc ccgtctctac tgaaaataca aaaaaaaaa aaaaaaaatt    13680 ggccgggcat ggtggcgggt gcctgtagtc ctagctactc gggaggctga ggcaggagaa    13740
tggcgtgaac ccaggaggca gagctttcag tgagccgaga tcgtgccact gcactccagc    13800
ctgggcgaca gagcaagact tccgtctcga aaacaaaaca acaacaaaaa aaacaatgga    13860
ttcaccatcc gatgggctcc ctcactgcca ggtcactctt catggaagta tttgtattcc    13920
agtcctttct gtggaaagaa cttaacattc tccttttcat aacactgtat cttcagaaac    13980
aagagagtcg aagtctccta attttcagga gtgtctatgt tgaacatcaa aatatattct    14040
ttagagcaga tctttaataa tcatatgaca agagaaaaac tttcataatc ttatgacatg    14100
agggaaggaa tattaaagcc gttctgtggg ttattatctc taacgttccc aatagaatag    14160
gctttgccag ctgggtgcgg tggctcatgc ctgtaatccc agcactttga gaggccaagg    14220
cgggcaaatc acgaggtcag gagtctgaga ccagcctgac aacatggtg aaaccccgtc    14280 tctactaaaa atacaaaaat tagccgggca tggtggtggg cgcctgtaat cccagctact    14340
caggaggctg aggcaggaga atcgcttgaa cccgggaggc ggagattaca atgagctgag    14400
atcacgccac caactccagc ttgggcgaca gagcaagact ctgtctaaaa aaaaaaaaaa    14460
```

```
aaaaaaaaaa aaaaaaaaaa aaaaaaaaat aggctttgcc cattatactc tctcatattc    14520
attgacctga atcctcaaat gaggtgtgtc cattagtcaa ctccaatctc ttgtcatata    14580
taagatggta gagatgagaa gaaggtagct cctttacagc ccactatttc cactaactac    14640
tacctgtgtt tcaagataca gcctttcatc cttctccagt gttgagagtg ttgaacctca    14700
gagtttctcc tcttattttc tctaaatgag atacaatgcc agccatccca agctcttggc    14760
ctgagttgtt catcttgaag tctaggactc caagaagcat gaaagagctt ctttagtgaa    14820
gctatgtcct cagtactgcc aaaattcaga caatctccat ggcctgacaa tttaccttct    14880
atttgggtaa tttattgtcc cttacgcaaa ctctccagct gtcatggcac agacatatga    14940
tctgtattta gctctcactt taggtgtttc cattgattct attctcacta atgtgcttca    15000
ggtatatccc tgtctagaac tcagattggg gttaaagagt ctgtccgtca ttgaccaaca    15060
gtcttaaata cttgatttgt tgtcgttgtt gtcctgtttg tttaagaact ttacttcttt    15120
atccaatgaa cggagtatct tgtgtcctgg acccttgca agaacccttc ccctagcaac    15180
agatgcgtca tctcaaaata tttttctgat tggccaaaga gtaattgatt tgcattttaa    15240
tggtcagact ctattacacc ccacattctc ttttctttta ttcttgtctg ttctgcctca    15300
ctcccgagct ctactgactc ccaacagagc gcccaagaag aaaatggcca taagtggagt    15360
ccctgtgcta ggatttttca tcatagctgt gctgatgagc gctcaggaat catgggctat    15420
caaaggtagg tgctgaggga atgaaatctg ggacgataga ctacgaagca ttggagaaaa    15480
gacctatgga catttggaag ataatgtgtg gagtgaaaga atagtgtgac aggtattatg    15540
tggtctcgac agaaagtata acaaattgtg gtttggtgga gttcttccct caccacaaac    15600
tgaagtaagt caaatttggt ttagaggatc aaaactgagt tgtgtattga tgaatagcaa    15660
ggtcctgcta caagccaaac tgggggtggg ggtggggtg gggaggaag aatattttct    15720 ggcaagcatt aacaagttat atttctgggc tttaattatt ct тт ст ggaa aattagtaaa    15780 attaaaaact aaaaaccaca catagttttg ctagaattaa atgaaaaaaa aagttatt ag    15840 ccctgttctt atctgaatac atgatacagt agttattttt tggagtgtaa atcctgtcgg    15900
tatatattga gcacatatat tgtgttgaag attactagaa ggaaaagtca tcaaaaagca    15960
acaatttacc ccaggaaaag gggagggaag gcatgctgat atgagttgcc tcatgggaca    16020
gtgatagcca ttccctgcct tcccatctcc atggtacagc agatcttata tcatgttaac    16080

ttagtaatat ttccaagaga gtagaaaaat gagtaaggaa atgggaaatc tgatattatt    16140
ctctctcatc tccagagcaa cattggtgct gttgtaaaga tgtactgtag aaaagtattc    16200
ttcacccagc atgaccccca cagaaggtgt caggtagact tgaaataagc aaagtaataa    16260
cccagctccc atacccatag tggcaattgt agatttctat tgccccaaaa gagccataca    16320
tagggatact tacctagaaa gacagaggct cttcctt ggg tttgtgaaga ggcagctagt    16380
atatttgtgt gtgtttgcat agatgcaaac ggtaaataaa ttcctaggtt tatcaataca    16440
cagtcaaaca ttaaagtctc tcatcttggc tgggcacggt ggctcacgcc tgtaatccca    16500
gcactttggg aggccgaggc aggcggatca cgaggtcaag agatcgagac cgtcctgggc    16560
aacatggtga acccccgtct ctactaaaaa tacaaaaaat tagctgggta tggtggcaca    16620
cgcctgtagt cccagctact cgggaggctg aggcaggagg attgcttgag cccaggaggc    16680
ggaggttgca gtgagctgag atggtgccac tgcactccag cctggcgata gagcaagact    16740
ccgtctcaaa caaccaaacc aaaacaaaac aaaatatctc accttatctt tgaagactaa    16800
```

```
ggaaaaaaaa atctcccact catcgataca ctccacagag gcagcatact ctccaagtgt    16860
agctttctct tttcatgttc attattccct tggtgttggt tattctcaat gtcaatcata    16920
acagaacatc ttccataata acagtcccaa tttaaggagc attaagataa aaggtggaat    16980
tgccaaggtc aatccagacg agaaccttct catagaggta accaccgtgt gggtttggat    17040
gctgggaagc aggggggacta tgacgctaca aggtctcagt cttaattttt ggagtatttc    17100
agtccccagg tatattttcc atagatttgg cccttaaata aaaagaagct tctgactcta    17160
aaatgtaaac agtgcttgtt acagtcttgt tgatatatta agaaattact caccttatct    17220
catttaatct taaaaacaaa cccctgacag gatcaaaacc acagcagggc tacataaatag    17280 gaaaactata cataaatagg tagaataatc tgctcaggat cactaggtaa gttgctgaat    17340
aagaattcaa gatgtttttg atcccagagt ttaaaaccca acctttcaaa cagcgtttct    17400
ttcttcttag agtacaatgt tctgagaaag agatcctctg gaattctggc ctaagtgtat    17460
ttaatgcccg ggtaaagaaa gtgagagaac atttctcttt aggggctgct gctggatttc    17520
taaaaagaaa ataatttctc agctagtaac atggagccaa acaacagctt cacaagactc    17580
tgggttcttt agccctcatc tccttcaatc caccctcttt ataaccagtc cttcttgttt    17640
ttcccctccc agctttgttc agcagcatgc ccttcaccca gaccttgtct tgtcactcat    17700
ccctactcgc catcattctt tcattcctct tggcccaatc tctctccacc acttcctgcc    17760
tacatgtatg taggttattc atttccctct cttgattccc cccacccaac tctctttctc    17820
cacttctcgc ctttcagaag aacatgtgat catccaggcc gagttctatc tgaatcctga    17880
ccaatcaggc gagtttatgt ttgactttga tggtgatgag attttccatg tggatatggc    17940
aaagaaggag acggtctggc ggcttgaaga atttggacga tttgccagct ttgaggctca    18000
aggtgcattg gccaacatag ctgtggacaa agccaacctg gaaatcatga caaagcgctc    18060
caactatact ccgatcacca atggtacctc cctctctgct gcactcctgg acatgggaat    18120
ccatagtttg aaagtagttg cttcagctct ttgtgttaga ttattgtaac tgattttccc    18180
tccaagggcc taaccttgcc attaacaagc cccaaattct catgccagag gtctgagaac    18240
tttatgggtt tgatcctatc ttgttgtgct caagtcttgt ctctgtcatc catggtctcc    18300
tacaaagtca ttgccctaag ttcatgctgg gggagccaga agggaagtcc ttggatatct    18360
tatacctcaa tattggctca atttcttggg gaggggtgc tgtcagagat tgttatctga    18420
ggatgtgaca tagatttctc agggcacaat ttcaactact ttttcagctt tagggtttt    18480 agatacgttt gtaccacaat tgagcatggg agggagaggg tgagcctaa gcagtgatgg    18540 ctgatttctg tcatgtctgt catgtgtccc ccagtacctc cagaggtaac tgtgctcacg    18600
aacagccctg tggaactgag agagcccaac gtcctcatct gtttcataga caagttcacc    18660
ccaccagtgg tcaatgtcac gtggcttcga aatggaaaac ctgtcaccac aggagtgtca    18720
gagacagtct tcctgcccag ggaagaccac cttttccgca agttccacta tctccccttc    18780
ctgccctcaa ctgaggacgt ttacgactgc agggtggagc actggggctt ggatgagcct    18840
cttctcaagc actgggggtat ggaccaacac tcaatctcct ttatttcaag gtttcctcct    18900
atgatgcttg tgtgaaactt ggtgttctaa ctgtttcata atatctgcta caattaatat    18960
aactgtcttc tcctactatc cagcttccgc cttttttaa tctgtaattc tctcaataca    19020
tcattctgtc ttcctcttct ttaatctatg aataactttt ctctttatta agaaccctac    19080
atttgattct gagtgttact tcttcccaca ctcattacca tgtactctgc cttatttccc    19140
cccagagttt gatgctccaa gccctctccc agagactaca gagaacgtgg tgtgtgccct    19200
```

```
gggcctgact gtgggtctgg tgggcatcat tattgggacc atcttcatca tcaagggatt    19260
gcgcaaaagc aatgcagcag aacgcagggg gcctctgtaa ggcacatgga ggtgagttag    19320
gtgtggtcag aggaagacat atatggagat atctgaggga ggaaaacagg gtggggaaag    19380
gaaatgtaat gcatttaaga gacaaggtag gaacagatgt ggctcttgat ttctctttgc    19440
tagaacgaat cagacattgg tatcatctgg tatcccaaag cttcagggtc tgtcatccct    19500
ttctatagac gggcaccttg atcacggctc cagtcttaga aatcatctcc agtacctaaa    19560
accattgttt cacattagaa tactgagtct agggatctag aaaatactga gtctagggat    19620
ctagaaaaat aagcctcaag atttgggcac atcctagctt gtatttcctg gggcaggtca    19680
tcagttcaga agcatttcca gatcctggct cctttcaggt tagggtcaat tcattgcatg    19740
aaatgggaat ctcttagagg ccaatgcctg cttttgcttc tttagtctca aatgtagtat    19800
gagaaactct aaaaaaaggt aaagcatggt tgcttattat gttcagttgg agagtagggt    19860
atacagttag ttcatgttgg aaaggttaga tgaacattga agaattttg caaagtcaaa     19920 ggattaagag agaagaggaa ggaatctgaa gcaaggagct caaaactgat cttaaactcc    19980
ttggtaacta tgtgtgtctt gctataggtg atggtgtttc ttagagagaa gatcactgaa    20040
gaaacttctg ctttaatggc tttacaaagc tggcaatatt acaatccttg acctcagtga    20100
aagcagtcat cttcagcatt ttccagcct atagccaccc caagagtggt tatgcctcct     20160
cgattgctcc atactctaac atctagctgg cttccctgtc tattgccttt tcctgtatct    20220
attttcctct atttcctatc attttattat caccatgcaa tgcctctgga ataaaacata    20280
caggagtctg tctctgctat ggaatgcccc atggggcatc tcttgtgtac ttattgttta    20340
aggtttcctc aaactgtgat ttttctgaac acaataaact atttttgaaga tcttgggtgg   20400 aattttggt gtttaagcca gttctttggg tggcggtggg gggtgggag tcggtcctgg      20460 ggaatatatg tgatccttc ccggtaaaat atctgaatgt tgaatttatc ttataaattc     20520
tagaattcat cagacatatc ccggttcatt tgggcttggt ctcattttgt gcatctgcag    20580
gcaaccctct tgttgtggtc tagtcctcat caggaaaacc taaagtgggg ttggtttgtt    20640
gggagatctc tactgagcaa tgatataact ctatcttcag tagagtgaat ctgaaacccc    20700
aaggtatgga tctcagaatg catgggatgg aggggagcag atggggttag agtgggagag    20760
aggaagacag aagaatccat aaacattgca ggatttacat atcaacatcg ttcattccag    20820
atttaatgag caaagagatt ggacactgaa gactggcctt acccattctg ttagacatag    20880
tctcagatgc ctatttatt accgagagag tagtctgact gattcttgaa accaccttat     20940
atttgaagat gtgtctttga gtggaaaagc tgagtgaaat ttggggttgg ggagaaagat    21000
atgacattaa gatgagagga aggaatattt gaaacacgat gaactgttgc tcatttgtct    21060
ataaaactat gacttgatat ttatctctaa aatagtttct agaacctgcc ataaaccact    21120
aagataaact attcatgata gtgtggtaga ctgcaaataa atgctgttga aatgagttag    21180
gcttgggttt catcttggct gtatcattta ctagctatgt tttcactggt atcttactta    21240
acttagcctc acattactca tgaaaatact ggtgttaatt tttactacat tgaattaata    21300
tcagaattaa aaggaaaacg caagcaaagt aattagatac atgcttagtg ataataaaat    21360
attgcaaaaa attatacatt ctgttgtttt tctcaaaatt tctatagagt gatgataaaa    21420
atctaagaga agctaaacaa aacaaggata aaccaaagca tcatgacctt ctaagcctta    21480
ctaataaata agaagtttct cggctgggca cggtggctca cgcctgtaat ccagcacttt    21540
```

```
gggaggccga ggtgggcgga tcacaaggtc aggaaatcaa gaccatcctg gccaacatgg   21600
tgaaacccca tctctactaa aaatacaaaa attagccagg cgtggtgata ggcgcctgta   21660
atcccagcta ctctggaggt tgaggcagga gaatctcttg aatccgggag gcagaggttg   21720
cagtgagccg agatcgcacc actgcgctcc tgcctggcaa cagactgaga ctccgtctca   21780
aaaaaaaaaa aaaaaaaaaa aaaagtttc tctactgttg gttcagagaa tcaaagcaga   21840
atcttgagac tactgacggt agaataggta tgaatgtctt tcttacatga ctacaaactt   21900
tattataaaa taaatagctt aacacagaga atacactaaa acttagacaa gcatggatta   21960
agaaagcaaa aagtaaaccc atatactacc atgtaagaaa accatttttg gccaggcgtg   22020
gtggctcacg cctgtaatcc cagcactttg ggaggccgag gcgggcggat cacgaggtca   22080
ggagatcgag accatcctgg ctaacatggt gaaaccccgt ctctactaaa aaaaaaaaa   22140 aaaattagcc gggtgtggtg gcgggtgcct gtagtcccag ctactcgaga gttgaggca   22200 ggaaaatggc gtgaacccaa gaggcagagc ttgcagtaag ccgagatcgc accactgcac   22260
tccagcctgg gcgacagagc gagactccat ctcaaaaaaa agaaaaaaaa aaaaaaaaa   22320 aaaggaaaac cattttaata gacttttatt tttagagctg ttttaagcta acagaaaaat   22380
tgcagaaatt gtatacagag ctcccccacc cccagtttct acaatgctta acatcctgta   22440
ttaatgtggt acacttgtta caattgatga accaatacta ataattatta ttaactaaaa   22500
ttcatagtta tacgagggtt cactctgtat tacacagtta tatgggttct gacaaataca   22560
taatatcata tatccaccat tacaggatta aacaaaatag cttcactgat ctaaaaatga   22620
cccaggctcc atctactcat ccttccttcc tccctctgaa ccattggcat tctctgagct   22680
atttactagt gttttgcctt tttcagaatg tcacatactt gtaatcatac agcatagagc   22740 ttttttcagat gagattcttt tgcttagcca tatgcataca ggtttcctgc gtatattgtc   22800
atagcttgat agcttatttt tctttaatgt taaataatac tccattgtat aaatgtacta   22860
tggtttattt acccattaat ctattgaagg acatcttggt tgcttctaat ttttggcaat   22920
tatgaataaa gctgctataa acatccatga acagatgttt gtgcagacac aagttttcca   22980
ctttggataa atacatagaa gggcagttgc tggatcatat ggtaagagta tgtttagctt   23040
tgtaagaaac aactagaata tcttccaaaa tggctgtatc attttgcatt cctaccagca   23100
acgaatgaga gtccctgttg ttctatatcc ttgccagcat ttggtattct ggggtttggg   23160
atttcagcaa gaaagccatt ttaatatttt tttattttaa aataattata gattcagggg   23220
aaattgcaaa gacagtatag agacattctg catacgcctt cacccagttt ctccaaatgt   23280
ttatatttta agtaattata gcacagtagc aaaaccaaga aaatacccttg atacaatgtg   23340 tatgtatagt tttatgcatg tcttaccaca tttgtagatt catgtaacca ccaccacaat   23400
caagcacaga gctattccat atcacagaga tcttcatcat gcttcccttt atagccaaat   23460
tccccccaca caatcacctt aacaacttaa aaccactaat ttctttgcta ttaatctcta   23520
gaatagtgtc attttgaaaa tactagttaa atggaatcat gcagtatgtg actggtgttt   23580
ttcacttagc ataatacacc tgagatccat ccaagctgct gcatatatca acaatctttt   23640 ttttttttatt gctaagtagt attccatggt ctaaatgcag cacagtttgc ttaactattt   23700
gcctattgaa ggacattttg gctgtttcta gtttggggtc actataaata aggctgtttt   23760
gaacatgtgt ttaaggtttt tctatgagca tgagttcatg agttttcatt tctctggtat   23820
aaatgtctgg gatataattc atgggcatat ggaaatatat gtttagtttt tcaagaaact   23880
gccaaactta gccaagtatg atggcttata cctgtaatcc cagcactttg ggaggccaag   23940
```

```
gaggaaggat aaattgaggc caggaatttg aggccagccc cagcgtctac acttttttt    24000
ttttttgaga cagagtctcg ctctgttgcc agactggagt gccatgatgc gatctcggct    24060
cactgcaacc tccgcctccc aggttcaagc aattcttctg cctcagcctc tcgagtagct    24120
gagactacag gtgcacacca ccacgcccaa ttaatttttg tattttagt agagacaggg    24180
tttcaccatg ttggccagga tggtcttgac ctcatgacct cgtgatccgc ttgccttggc    24240
ctcccaaagt gctgagatta caggcatgag ccaccgtgcc cggccaaatg ttttgttttg    24300
tttttgtttt ttgttttttt gtcaggtgga tgaggtggca tgcccctata gtcacagcta    24360
cttgggaggc tgaggtggga ggattgcttg agcccaggaa ttcgaggctg cagtgagcca    24420
ctgcacttca gcctatctga cagagcaaga tcctgtctcc aaaaggaagg aagggaggga    24480
agaagcaagg aaggaaggaa ggaaggaagg aaggaaggaa ggaaggagaa aaagaaggt    24540
agggagggag gaaggaaggg agggagggag gaaaaagaa agaagaaagg aagttaaaaa    24600
gaagggaggg agggaggaag gaagaaagga aagatggaag aaaggaagga agggagggag    24660
gagaaagaga aagaaaaaga aggaaggaag aagggaagga gggagggaag ggaggaaggg    24720
agggagggtg aaaggaagga aagaaggaag gaaggagaaa gaaaaggaag agagaaagag    24780
aaagaaaaaa gaaagaagaa agaaagaaga agaaagagaa gagaaggaaa ggaaagaagg    24840
aaggaaagga aagaaagaaa aagaaaaagg aaggaaggaa agaaggaagg aagaaagaaa    24900
aagaaagaaa gaaggaagga aagaaagaaa gaaagagaaa gaaagaaacc gataaactat    24960
tctctaattg ctttgtggga gtatggccac tttcatcata ttgattttc ctttttttt    25020
ttttttttt tttttgcga tagagtctgg ctctgtcgcc caggctggag tgcaatggcg    25080
tgatttcggc tcactgaaac ctctgcctcc tgggttcagg tgattctcct gcctcagcct    25140
ccctagtagc tgggattaca ggtgcacacc atcacgcctg gataatttt ttgtatttt    25200
actagagatg gggtttcacc atgttggcca ggttggtctc aaattcctga cctcaggtga    25260
ttcgcctgcc ttggcctccg aagtgctag gattacagat gtgagccacc gcgcccagac    25320
aatattgatt cttccttttc catgaacatg atattttttt ccatttattt gtgtcatctc    25380
tgagttcttt gagcagtggt ttgtagtttt ccttgtagag atctttctcc tccctagtta    25440
gctgtattcc taggtatttc gtgtgtgtgt ggcaatcgtg aatgggatta cgttcctgat    25500
ttggctctca gcttgactgt tgtggtgtat aggaatgtta gtaatttttc cacattaatt    25560
ttgaatgcca agacttcgct gaagttgtta attagcttaa agagctttg ggctgagact    25620
atggggtttt cttgatatag gatcatgcca tctgcaaata ggcatagttc aatttcctct    25680
cttcctgttt ggatgccttt aattcttttt cttgcgtgtt gccctggcca agacttccaa    25740
tactatgttg gataggagta gtgagagagg gtatccttgt cttgcgctgg ttttcaaggg    25800
gaatgcttct agcttttcc catttagtat ggtattagct gtggggttgt cacagaaggc    25860
tcttattatt ttaagttatg ttcacttact actcagttta ttaagagttt ttaaatgaag    25920
ggatattgaa ttttatcaaa aaccattcct gcatctattg agctaatcat gtggcttctg    25980
tctttagtac tgcttatgta atgaatcaaa tttattgatt tgcatatgtt gaactaacct    26040
tgcatcacca agataaagca tacttgatca ttgtagatta gcttttaat gtactgctgg    26100
attcagtttg ccagtatttt gtggaggatt tttgcataaa tcttcatcaa taatatttgc    26160
ctgaagtttt cttttgtgtg tgtgtctgcc aggttttggt gctgatcctg atgatgctgg    26220
cctcatagaa tgagttagag aggtatccct cttcctcaat ttttttggact aattataaca    26280
```

```
ggaatggtac cagctcttct ttgtacatca ggcagaattc agctgtgaat tattctagtc    26340
ctaggggttt ttttgtttg gtagtctact tattactgat ttaatttctg agatcattat     26400
cagtctgttc agggattgaa tttcttcctg gttctgtctt gggagggtgt acgtgtccag    26460
aaatttatca atttcttcta gttttcctag tttatgtgca tagaggtgtt tttaatattc    26520
tctgatggtt atttgtgttt ctgtggggtc agtggtaata tccccattgt aatttctgag    26580
tgtgattatt tgaatcttct ctcttttctt ctttattagt ctaactagag gtctttttt     26640 tttattaatt ttttttagg aaaccaattc ctggactcat tgatcttttg agtgttgttt     26700 tttttctgt ctcaatctcc tttagttcag ctctgatttt ggttatttct tgtcttctgc     26760
tagccttgat attggtttgt acctggttga ccagttcttt tagttgtgat gttaggttgt    26820
taaattgagg tctttctttt tcatgtgggc atttgatgca taaatttccc acttaacact    26880
gccttagctg tgtcccagag attctggtat gttgtatcgt tgttctcatc agttttaaag    26940
aacttctcaa tttcttcctt aatttcatta tttacacaaa agtcattcag gagcaggcgg    27000
ttcaacttcc atgtaattgt agggttttga atgaatttct tagtcttaat ttctaatttg    27060
attgcactgt tgtctgaaag attgttttt atgatttcag ttcttgtgca tttgctgagg     27120
agtatttgac ttccgattat gtgatcaatt ttagagtaca tgccatgtgg tgatgagaag    27180
aatgtgtata ctgttgtttt ggtgtggata attctataga tgtctatcag gtccatttga    27240
ttcagtgctg agttcaagtc ctgaatatct ttgttaattt tttgtctcga tgatctgtct    27300
aatattatca gtgagttgtt aacatctcca agtattattg tgttggagtc taagtctctt    27360
tgaaggtccc taagaacttg ctttatgaat ctgggtgttc ctgtgttggg tgctgatctg    27420
gtttggctgt gttcccattc aaatctcacc ttgaattgta gctcccacaa ttctcacatg    27480
ccacgggagg cacctggtgg gaggtaattg aatcatgggt gcgggtcttt cccatgctat    27540
tctcatcata gtgaataagt tcatggagat ctgatagttt tataaagagg agtttccctg    27600
cacaagttct cttgtcttgt ctgccaccat gtgagatgtg atttcacct tccatcatga    27660 ttgtgaggca tccctagcca tgtggaactg tcagtcaatt aaatttcttt cttttgtaaa    27720
ttgcccagtc tcaggtacat ctttgtcagc agcataacag actaatagag gagagtggag    27780
cactgctgaa aagatatctg aaaatgtgga agtgactttg gaactgggta acaggcagag    27840
gttgaaacag tttggagggc tcagaagaag ataggaaaat gtgggaaatt ttggaacttc    27900
ctagagactt gttgaatgcc tttgcccaaa atgctgatgg tgatgtggac aataatgtcc    27960
aggctaaggt agtctcagat ggaaatgagg aacttgttgg gaactggagc aaaggtgact    28020
cattatgctt tagcaaagag actggtggca ttttgtccct gtcctagaga cttgtggaac    28080
tttgaacttg agagagatga tttagggtat ctggcagaag atatttctaa gcagcaaagc    28140
attcaagagg ttacttgcgt gctgttaaag ccattcagtt ttataaggga agcagagcat    28200
aaatgtttgg aaaatttgca gcctgacaat gcaatagaaa agaaaatcca atttctgag    28260 gataaattca agctggctgc agaaatttca tgggtaacga ggagctgaat gttaattatt    28320
aagacaatgg ggaaaatgtc tccaaggcat gtcagaggtg tttttttttt ttttccagag    28380
tctcgctctg tcgcccaggc tggagtgcag tggtatgatc tcagctcact gcaagctctg    28440
cctgccaggt tcatgccatt ctcctgcctc agccttccaa gtagctggga ctacaggcat    28500
ccgccaccac acctggctaa ttttttgtat ttttagtaga cacggggttt caccatgtta    28560
gccaggatga tctcgatctc ctgacctcat gatccaccca cctcggcctc ccaaagtgct    28620
gggattacag gtgtgagcca ccatgcctgg ccatgtcaga ggtcttgatg gcagccctgc    28680
```

```
ccatcacagg cctggaggcc taggaggaaa gaatggtttc ttgggctggg cccagtgtcc      28740
ccgtgctgta tgcggtcttt ggacttggtg ccctgtgtct cagccgctcc agctgtgact      28800
aaaaggggcc aacatagagc tcaggccacg acttcagagg atgcaagccc caagccttgg      28860
cagcttccat gtggtgttga gcctacgtgt acacagaagt caagagttga ggtttgggaa      28920
cctccaccta gatttcagag gatgtatgga aatgcctgga tgtccaggca gaagtttgct      28980
gcctgggcag ggcactcatg tggaacctct gctagggcag tgcagaaagg aaatgtggag      29040
tgggcaccct cacacagagt tctcaatggg gcagtgccta gtggagtttt gaaaagagga      29100
acaccatcct ccagactcca gagtgatgga tcc                                  29133

<210> SEQ ID NO 3
<211> LENGTH: 22485
<212> TYPE: DNA
<213> ORGANISM: Homo sapiens
<220> FEATURE:
<221> NAME/KEY: gene
<222> LOCATION: (1)..(22485)
<223> OTHER INFORMATION: HLA-DRB1*010101 gene
<220> FEATURE:
<221> NAME/KEY: misc_feature
<222> LOCATION: (7391)..(7552)
<223> OTHER INFORMATION: exon 1 - HLA-DRB1*010101 gene
<220> FEATURE:
<221> NAME/KEY: misc_feature
<222> LOCATION: (7453)..(7455)
<223> OTHER INFORMATION: ATG codon start
<220> FEATURE:
<221> NAME/KEY: misc_feature
<222> LOCATION: (15809)..(16079)
<223> OTHER INFORMATION: exon 2 - HLA-DRB1*010101 gene
<220> FEATURE:
<221> NAME/KEY: misc_feature
<222> LOCATION: (19536)..(19817)
<223> OTHER INFORMATION: exon 3 - HLA-DRB1*010101 gene
<220> FEATURE:
<221> NAME/KEY: misc_feature
<222> LOCATION: (20515)..(20624)
<223> OTHER INFORMATION: exon 4 - HLA-DRB1*010101 gene
<220> FEATURE:
<221> NAME/KEY: misc_feature
<222> LOCATION: (21097)..(21121)
<223> OTHER INFORMATION: exon 5 - HLA-DRB1*010101 gene
<220> FEATURE:
<221> NAME/KEY: misc_feature
<222> LOCATION: (21750)..(22085)
<223> OTHER INFORMATION: exon 6 - HLA-DRB1*010101 gene

<400> SEQUENCE: 3
cttgttaact actattgtat tctctgcttc tatgagcttg agtattttag ttacctcata        60
taagaggaat tctgcaatat ttgtcttcct gtaactggct tatttcactc agcataagcg       120
aaactaaaaa gcttttgcat agcaaagaaa acaataaaca gaatgaaaag ataacctgca       180
gaatggaaga aaatatttgc aaaccatata tttgataagg ggttaatttc aaaaatgtat       240
aaggaactca tacaactcaa gagcaaaaca accaaccaaa caacaagct gattaaaaaa        300 tgggcaaagg acttgaacag atatgtcttg gaaaagatg ttatagacta aatgtttgtg        360
ttccctccta atcatatgtt aaatcctaag ccccaatatt ataggattag aaggtgggcc       420 cttttggaagg aattaggtct agagtctatc tagataaaca ctccaattaa ttgcccatat      480
gggaacacaa attggtttct gatggtgtaa agttattaag gaaaaataat aacaataaat       540
ggataaacag gatcaatttc ttccttaccat ggagggagga tatgtatcct caacagaaga     600
ctgtgccatt taaaggccat attagtattc atcagagttg ataggaccct ttcctgtaag      660
```

```
atttcagcaa tgtcatccat cgaggaactt tgggtggagc cagtctttgc accatggcac    720
tatctaggtc atggctgtaa gtctacaagt gaaaaaacca tggtcaatat taatgatatt    780
gcaattagta tcagcaatac cactgaagga acgttgaca gttaaaataa tttaggaggc     840
tgggcacagt ggctcacgcc tgtaatccca gcactttggg aggccaaggt caagagatag    900
agaccatcct agccaacatg gtgaaacccc atctccacta aaatacaaaa aattagctgg    960
gcatggtcgt gtgcacctgt agtcccagct actcgggagg ctgaggcagg agaatagcct   1020
gaacccagga ggcagaggtt gcagttagtc aagatcacgg cactgcactc cagcctggca   1080
acagagccag actctgtctc aaaaaaaaaa aaagaaaaa aagaaaaaa aaagaattta     1140
gtgtttaaat cctgttctgg agagaaaata aacccatgcc tatgtatttt gcctcagtgg   1200
cagaaccagt tgcttttaga actgattctt gttatgcttt tttgttttc atagctttag    1260
aacttgtaat agcaataaag attcctcact tctggaaaaa ctcaaaaatt tctaataatc   1320
cttatattat cttctgctgt ggttattata agtattttc ctctggttaa taatatagct    1380
atggcttaga ttatttttta ctagctggta ccttttttct tattctaaca gttgactaga   1440
catctcttta aggtcaaatc caaaattgtg aactatggac actgacaggg ttttgtttgc   1500
acccaaatca tctttagcat ctctagatgg atacttaata gtaccaagtt ttacaccttt   1560
atcttgctgg tgtaaccct tgaatgacca catgaccaac acaggatgc tagcaatagt     1620
tagtgtggtt cttatgcttc attttctca gaattgctgt atgatactga gagttgcttt    1680
gtttgacagg cacacagggt aggaagagat gtcatgacaa aaggattagc taattctttt   1740
gcacacacat aagttgattt tatttaggta aaatgttgtt aacataaata agtactagta   1800
agttacttt ttcaagataa taaattgtct gcaaggatga gctattagaa aaataactgg    1860
taaaagattt tattatttat tttaaataaa ataagcaaca aaccaggcac acacttcaca   1920
ggacagattg caaagaggtt ggtacagctc aacaggttca tcaatgtctt cactgtccac   1980
actgcagtca ctggggagtg ggctagtgga gcaccaaaat gaaattttga aaaataacct   2040
ggcctatttt ggactggata gatagttgga tacttaccac agcacaatta acataagagc   2100
tagaaagata aatcaaaaga aaattctttg tacttacaat attagtagaa aggcctatgg   2160
gaattctagt tgttttctct atatgcaatg gcaagcattc tgttataaaa cagctaagtt   2220
gagccaaaga atgacatttg gaagttaaag aagtcctgtc aactgaccta gatagtgtca   2280
tggtgtaatg attggcgcta ccaaagtttc ttaatggagg acattgctga gattttactg   2340
gaaagggtcc tatcaagtgt gatgaatact aataaggcct ctaaatggca cagttttctg   2400
ttcaggatac atatcttcca tgctgagaag aaactggttc tgtttatcca tttattgtta   2460
ttgtcatttt ttcttttagat ataaggatta gtaatctgct ttttacttta aattccagat   2520
agcagtggtt gctttctgaa aactcctgag aacattttgt gactgcttgg acaagtgaca   2580
gacattctat gataaccagg gcttgctgat agccaaaaaa gcctattttt ccaaaatgtg   2640
ttgcaagctt tcagccttac tgcaagtgag ccccattctg tgacaatcgg taggactcaa   2700
gacattctgt aatcctacca atgtcaacct gcctgttgtt cagcaaaagt ctgtgcttct   2760
gattttacct gtttagtcct gagaatgctg ggatttattt cctgtaaaac caagcctatg   2820
gtttcattca tcaagaccag agaccatgca acttccgtac ggaaaccac tttcttccag    2880
aaaccaattt aattgccatt tcctcaggaa ataagctctc gtatttgaca cctctcacac   2940
acagcagagt tgagaggatt cttctcttgt tttcagtgca aaagttcagc ctagagatca   3000
cctgtacgat tgatggtttg gtgacagttg ctacattgtt tagcctgaac tatgcttata   3060
```

```
ttgaatattg aaggaaagtg tgagatatat aatttaaaga agcatatctg ttatagttta    3120
agtgtgtcgc ctttaaaatt caggtaggac tcctcactga tgaatgggat taaggcccct    3180
gtaaaaaacg cttcacacag tttttagcct cttgtctttc caccttctac catgtgagaa    3240
cacagtattc atcccctctg taggatgcaa ggtgccatct tggaagtgga gagcatgccc    3300
tttgccagac attgaacctg ctggtgcctt aatcttggac ttctcagcct ccatgtattc    3360
tttataaatt acccagtcta ccgtatttta tcacagcaca aataaactaa gacaacatct    3420
ttgttactca taaatgtata aaacatacag aatttagttc attgccattg gccattttt     3480 aaatataaat ttgtatgatt tatgaatagc gtgtcaaatt tatataaaca aattttgaaa    3540
atttctcttt aactatattt tagtacattc ttgatgtaga attacttatt tttgcctctg    3600
catttatcct gtaataataa ggtgaacctt agcttccttt cctagattac cacaccacaa    3660
ttagttaatt agtaaattac gatttcctat tatcaaatga aatgtgatat tctcctggtt    3720
gcaattgcac aattgtcaat agtactgaat tatcactgta gtgtaggaac acagtttgtt    3780
ctcaaatcca gggacttcta cccaacctct ccaagaaatc ttcaactttc cacattaaca    3840
gaaatatatt tttccaaagt aaacgagaca ctattttttat tctattctga aatgatcaaa   3900
cttgcactac ttcgtgctga gaaattagaa atgatgattg agagtaataa accggagtta    3960
ggaatgttga ggctgttgtt atctttaata agaaggagat ttgtgcagga gctatgggtg    4020
tccttatgta acataaacgc aaactgtgtc atttccagag gagagtaacc atgatgatga    4080
ggggaatctt ttgaaggaac tagcattgct acacagtatc taccccaaag tctataaaat    4140
gttgccattc actaaaagaa gtagtcttac tgatttgcac agccatgaat taaagggata    4200
aaaataattt tagtataagg gacataattc tctttagaaa ttgaatgtga ggtagtataa    4260
tacaacagta gagcctgagg ggtttggaat cacatatata ataccttggt tcaatagagt    4320
tgacagaaaa actctgcttt aaaataatta atattttatg tgaagagtgt tcaatccctc    4380
attcctggct cccattatga tctcctcatt tgtttgaggc tatggcccct tactattcca    4440
cttctcttgt tttatcataa agggagatat aagaagactt tgctggccgg atgcactggc    4500
tcatgcctgt aatcccagca ctttgggagg ccgagttaca attctgagaa ttgctacaat    4560
tctgagtaca aagcaaaatg ctcaaaaatt gctgaagaaa ttttagtcat ttttattgca    4620
gcatggtgag tatcccaacc ctagaaacac taaggcacac aaggaaggag tgtgtatcag    4680
aactgtggta gggtgtgaat taatgcagaa ctttatctgt atagttgtac tttgaagtcc    4740
attctgaatc ttagatgcta catttatata aatataaagc ataataagta tctaaatgta    4800
gaattatatg tttaaaatta tatgattaca ttaactgatg taattcatag attttcccta    4860
gggttctgtt tcctgaacat tctgtaacgt attagttagc aaagtctttt ttttttttga    4920
aactgagtct cactctatcg accagactgg agtgcagtgg catgctcccg actcactgca    4980
acctctgcct cctggaatca agcaattctc gtgcttcagc ctcctgagta gctgggatta    5040
caggcatgca ccaccacacc cagctgattt ttgtattttt tctgttagta gagacaaggt    5100
ttcaccatgt gggccaggct ggtttcaaac tcctgacctc aagtggtcca cccacctcgg    5160
cctcccaaag tgctgggatt acaggcatga cccactgtgt cctgccagca aagtcttctt    5220
atatattccc ttatgataaa acaagagaag tggaacagta aagggccata gcctcaatca    5280
aatgaggaaa tcctaatggg aaccaggaat gagggattga acactcttca cataaaatat    5340
taattatttt aaaactattg ggggaaattc agccagatat caggcaaaat tcaccccga    5400
```

```
tatttcacgt agtttctttt ctatattccc taagtgtcgg ccggtctgag aaataaaggg    5460
acagagtacc aaagagagaa attttaaagc tgggtgtccc caggagacgt cacatgttgg    5520
caggttctgt gatgcccac aagccacaaa accagcaagt ttttattagt gattttcaaa    5580
aggggagggg gagtgtatga ataggggtgtg ggtcacagag atcacatgct tcacaaggta    5640
atagaatatc acaaggcaaa tggaggcagg gcgagatcac aggaccacag gaccggggcg    5700
aaattaaaat tgctaatgaa gtttcgggca ccattgtcat tgataacatc ttatcaggag    5760
acagggtttg agagcagaca accggtctga tcaaaaattt attaggcggg aatttcctca    5820
tcctaataag cctgggagcg ctatgggaga ctggggttta tttcatccct aagcttgacc    5880
acagaagacg gccacccct gaagcagcca tttcagaggc ctaacctcag ggaagtattc    5940
tctttctcag ggatgttcct tgctgagaaa aagaattcag cgatatttct cccatttgct    6000
tttgaaagaa gagaaatatg gctctgttcc acgtggctca ccagtggtca gagtttaagg    6060
ttatctctct tgttccctga acattgctgt tatcctgttc ttttttcaag gtgcccagat    6120
ttcatattgt tcaaacacac atgctctaca acaatttgt gcagttaaca caatcatcac    6180
agggtcctga ggtgacatac atcctcctca gattacaaag atgacaggat taagagatta    6240
aagtaaagac agggataga atcacaagg gtattgattg gggaagtgaa gtgtccatga    6300
aatcttcaca atttatgttg agagattgca gtaaagacag gtgtaagaaa ttataaaagt    6360
attaatttgg ggaactaata aacgtccatg aaatcttcac aatctatgtt cttctgccat    6420
ggcttcaggc ggtccctcca ttcggggtcc ctgacttccc gcaacaaaaa cagagttgtt    6480
ctgtcaacag ctgactttga gtccttgatc ggtctctcag accctgaat acttggattg    6540 cacagttgac cttatcacat tgttagggta agtgcataca aaggcaactt cagaccctcc    6600
attgcacata ggtggcccct gcaagccgct tgcctgtgtg tgttctggag ctgccactaa    6660
acttggggac agcatcagga gatacacttg aaaaaaccct ttttactcag attaaattat    6720
taacaaactt tccatttcct ttaacttact aaagaatctc tacctgtaaa taggtacaga    6780
ttaaactcgc tagtcaacag ctatcattct gtcatatcaa cagatactcg tggctgctgc    6840
tccttgaggc atccacagaa tcacagcatt ttccagtatt gaaagacctg aaagatcacg    6900
gtgccttcat tttaactgtg agacatgaag taattttccc aagtctacaa cagtaagata    6960
tggtgcaata aggaccagat taaagtctc ctgatttgca accatgttcc ctccatctcc    7020
tttactccta agcacactca cacactcact cctgcaaaca attctcttgt caagtgggaa    7080
atgaatgctc ttacaaggct caaatttgtg aacacatcac tgaccagcac agagctggct    7140
aacaataggg acacaattaa ggtgttttac acgcaactgg ttcaaacctt tcaagtacta    7200
aattaaaaca atcctttaaa gaaggaaatt gtttcagaaa aggaccttca tacagcatct    7260
ctgaccagcg actgatgatg ctattgtact cagatgctga ttcgttctcc aacactagat    7320
tacccaatcc acgagcaagg aaatcagtaa cttcttccct ataatttgga atgtgggtgg    7380
agaggggtca tagttctccc tgagtgagac tcacctgctc ctctggcccc tggtcctgtc    7440
ctgttctcca gcatggtgtg tctgaagttc cctggaggct cctgcatggc agctctgaca    7500
gtgacactga tggtgctgag ctccccactg gctttggctg ggacacccg acgtaagtgc    7560 acattgtggg tgctgaccta ctatggggtg gggaaaaaag ggagttgtgt taacattgtg    7620
cccaggccat gtcccttaag aaagtgtgac attttcttca gggattgccc atctttatca    7680 tatgatccc aaattattc caccacaaat ggaacttggc tacttgccct attcatgaga    7740
ctgtgtaaag ggcctttgta caggccatgt tttactttaa atctctacca ataaaaacctt    7800
```

```
tgcatcacat gtcctcaggg tctttagagg atttagaaat aaggatgcta aaataaattc    7860
ctcatacagc acttcccttt atcatgttga cttatgtcag acgaaacaag gttttgtttt    7920
gaaaattttg tgggagtcaa aggaattcaa agggtctctc ctagacgatc ctgtgttgtc    7980
ctccacagga cctgtggtgt tggcccctct tcctcatatg tgaggatgta cccagtggcc    8040
tccccattgt ttccttctt tttttctga actccagtgt ttataaagcc tgtatccctg      8100
tagcatatgt aggttctctg acagaagtta tacttagtgc tctttctttc ttatggggaa    8160
aaatccctgg atctgaaact gacatcttta gtacttggag tcaccctaca ggtaaagacc    8220
atttatgagg tattcattgg tgcctcctct tgatcggtct ctcagacccc tgaatacttg    8280
gatactcctc aagaacttaa ggcatcctct gaaaaactgg cccagattag tgcttattat    8340
taatctttta taacctttct atacttgttt ctcctgcatg ctctaactag acatgacaga    8400
agagattcaa ctaacatagg ataaattata tgaaattcta tttttgtaag tcaaaaatag    8460
tcaaatacca gaaaattaat aatgttcaaa ctatatactc tgtgtggggt taccgagacg    8520
acgtggacat tgttcacatc taatagggct gaaagtcaat gaagaagtcc tggaaactcc    8580
ttgtcttact ggggtcttgt cctaaatttc ataggttcac ccatcatgcc ctcagctttc    8640
cttaattagc catgtctgct tatctctacc tccagtttct ctctattttt ccccagctat    8700
gttgtcatca tttccagaaa tctctaaaac ttgcaaagat ccttagcact atgagatcca    8760
ttgaaagaga taattttttt cttttgaga cagggcttgg ttctgtcacc caggctgtag     8820
tgcagtggtg tgatctaggc tcactgcaac ctctgcttcc cacgctcaag tgatcctccc    8880
tcctcagcct ccagagtagc ggagactaca ggcaggcaaa catgtgcagc taattttcat    8940
gattttgtta gagatgagat tttgccatgt tgcccaggct gttcttaaac tcctggactc    9000
aagcaatcct cctgccttag cctcccaata tgctaggatt atagatgtga gccattgtgc    9060
ccaggcaaaa agagatgaac cttaatttaa aaatttcctt tttcttaaat cactgtttct    9120
ctatctgtga attcttcttc caactagaag gaggagaaag aagaagtttg cctgtatttc    9180
tcaccaggag gaggagtcta gtgtgatatc aaaatgaaag agtgctggag cttgatcccc    9240 ttcttgctttt ccaggatccc tgcagtgatc agttcccaca ccctggttta ttcatgtaaa    9300
gcacacttat ttttttcagc agctactctt tactgggctc cattctaagt tcaaatcatt    9360
ctatttgagt aagatagaga gggtcccgac tctcatggaa gttacacaag agtagaggag    9420
acagacacta acccaataag catttaacaa agaagaaaat gttagagaga catagtgcac    9480
tgaagaaaag acatcaggtt tgtgaaaaag agagacatgg attcacttac tttggttcat    9540
atgcttaggc agctataact gagaaagtga cattcagctg agacaacaaa ataaatagac    9600
agtcgtgaag atctaaagga cgaaagttcc agggagaatg aatggggggg aagctctggt    9660
gtgggaaatt atgtggaagg acagaaagaa ggctagaggg actgaactat agcaagcaag    9720
gaaatggaga ggcagaagat gaggtaggac acagagagga agtcaggagc ctcatcatat    9780
tagactctga tggccatggt aaaaaaattg aatttattt tatttttatt tatttttga      9840 gacggagatt tgttcttgtt gcccaggctg gagtgcaatg gcgcgatctc gactcactgc    9900
aacctctgcc tctgggttc aagtgattct cctgcctcag cttcccaagt agctgggatt     9960
acaggtgcct gcgaccatac tcggcttatt tttttgtatt tttagtagag acagggtatc   10020
accatgttgg ccaggctggt ctcaaactcc tgacctcaga taatctgcct ggcttcccaa   10080
agtgctgaga ttacaggcgt gagccaccat gcccaacctg aatttatttt gaatagatat   10140
```

```
gagaagctac tgtatggtta caaggacagt caatttatat tcgatttttt ttttttgaga   10200
cagagtcttg ctctgttgcc caggctagat tgcagtggta caatctcagc tcactgcaac   10260
ctctgcctcc tgggttccag caattctcct gcctcagcct cccaagtagc tgagaccaca   10320
ggtacatgcc actacacctg gctaattttt tgtatttta gtagagatgg ggtttcaccg    10380
tgttagccag gatggtcttg atctcctgac ctcgtgatcc actcccctcg gcctcccaaa   10440
gtgctgggat tacaggtgtg agccaccacg cccggcctat attcaattat taaaattaat   10500
tctagctact ctgtggggat tggattgttg ggtttcacaa gtggtcagga agactattta   10560
ggatcacagc agggaattct ccagggaaaa caggcttgtg gcttcataga gtgcattagt   10620
gataaagaca gtgaaaacga caaagtggac agactaggca tgtattttg cttagcttgt    10680
taatggatta ctctaaaggg ggtagaaaaa tcaagcttat tcctaaggat tttgttttga   10740
caaataagtg gatggtggtg tttattgaga taggaaaaac tgtgggagga atgatttga    10800
agtgggtggt tggaaataaa agttttgttt aaatttgaga tgatttattg acatttatgt   10860
ggagcaatcc gaaggtcaat ggcatttaag agactcatgg tgaggtgagg ccagggcttc   10920
aggtattat gttggcggca tcagtacgtg taatgtgtta aattccaggg agtggaagag    10980
gatacatagg gagatggatt gtgtggagaa aaagaagag ggtacaggcc agcaaagggg    11040
gctgagacag agcccaggga tgctggagaa acccaagag aacataatgg gtgtaagtca    11100
tggaaaatag attattttca aggagaaggg agaggtcaat tgtggtgagt accactaaga   11160
ggaggggggaa gtgagaacgt gacagagaag caagtgctgg gtttgctgga gttgatattt  11220
gcagtcaatg gagtatccag ggaggaaact ggattggacc atttgaagag caagtagaag   11280
tgaggacgag gttaagggtg actattttaa gtagagagct tcagggaagg actgtgctct   11340
gggttcaggg agcctgctgg atctaaagga aaagggctga agaggctgaa gagaaggagg   11400
aggacctgtg aaccagagat actgagttat tattagcaag gaaatactag agggtccctg   11460
tgtgcagtgc tgactgctca tgcaaaaggt cacacagaca atatttcaca cagccagtat   11520
ttattagtga catagaatat gccagttatt actctaggtc atgagaatag agtgataaat   11580
aaaatgaatc tggtcgccat cggtatatgc catgtaacat tttgcagtga ctgtgtacca   11640
ggcctatgaa tttcagtatg caatttcaat aacgatcctg ttgtatctgt ggtgtttaaa   11700
aacatataca tctctggaat ctaaaattga gaggatataa gtaaaccca gtattagaaa    11760
tttagtgctg gaaatcagac tgcagttaa atctgagcat atagaaagtc cctttcttct    11820
atgtcagcag atgccttttg tgtgaggttt aggtatacta cattattaga cataaaccag   11880
tgattctgcc ctatgttttc agaatgacaa ttctttatga aactaataga agaacagaag   11940
acaattgcaa aatcatgatg aagatgctag tggctttaga accaaggaat acaaaaaata   12000
atgtgagctg cagttatagg gattataaaa gttaaatgg gaatgcattt gagtgtttat    12060
tatgtgatca gtgctaataa gagtcatcat ttaattttac acttaacaat aatcctgtga   12120
ggattaagct attattaaat gcatttgata gattacaaaa aggcttaccg ttggtaaaaa   12180
ttgacccaag gggaagaggt cacatttta ttcagatttt ctgattctag agtttgagag    12240
tctgtccatc attagtgagt agtgacaata ctgtgtctaa attatcgaca gaatttctga   12300
tattcatatg tactatgttg tttcttagag tgtgggcaga gattcagggc tgctagttcc   12360
aatgtatagg agaaactttc attcattgtg catttatcat tttaaaagtt ctaggctggg   12420
tgcggtggct catgcctgta atcccagcac tttgggaggc caaggcgggc agatcacgag   12480
gtcaggagat gaagaccatc ctggctaaca tggtgaaacc tcgtctctac taaaaataca   12540
```

```
aaaaattagc tgggcgtggt ggtgtgcacc tgtagtccca gctacttggg aggctgaggc    12600
aggagaatgg catgaacctg ggaggcggag cttgcagtga gctgagatcg tgccactgca    12660
ctccagctcc accctgggca aaagagcgaa actccgtctc aaaaaaaaaa aaagttcta     12720 tatgtctgtc atggcatatg ttgaagaaca caaggaagta ttaaatcact ccttctgagg    12780
tttgtctagc aagttgggct aggattgcca aataaaatac aggtttctag ttaaatctga    12840
atttcagata cacaactata atttactgaa aatccaaatg taacttggca tcctctgatt    12900
ttatttgcca aatctgtcaa ccctacatga gacacatgag catggattac ggtgttaccc    12960
atggaagcca cagccacagt gacagcgact tcacacatgt ttattttta actttctctc     13020 tgtaaagaaa gtgcttagat aatttaggga taaaaagata gacattgttt gatccaggat    13080
gcactcctct ctgccatcgt ttctaaaggg caaagagaga tttccacagg tcttactcac    13140
agtctgactc acagtctggg gacctgctca tgctttgaaa ctgtctgtat gagaatgtca    13200
ttttcttggt ttctcccttt ctgagggggac ttgactacaa aactgagagt tctacctctg   13260
gccaaggctg gaaatttgat gcctgctagt attgttggga atgggagact gaaataaatg    13320
agttagttgg ggcattaaac aggaataaaa tagctgtggt tgtgattcat tactacaatt    13380
agtggactag tggcagagaa attaagaaag aagatgatgt gagagataaa ttatatgatt    13440
tggtaaggca agggaatcag taaatcttgg ttctgaacaa gttcatttc  tggaaagata    13500 gcactgtact gggaccagaa ttctacaaaa catccgtttt atgtaagacc aagattttca    13560
acaaatattt ttcaatgcag ttctcagctg ctccataact aatagtgact tattcaacac    13620
agatattttc agatggttca cacccatgtt tcttacccag ggacagttca ccacccctcc    13680
ccttccctcc catcactctt gaggaacatg tggcaatgtt agaataattt ttggttgtca    13740
caacaggggt ttcttctgat atttaatgag cagaagccag ggacactgct agagaaccca    13800
caatgttcag aatagactcc atcaccaacc aagatttatc tcgtccaaaa tgtcaatagt    13860
gctgaggctg gaagcattgg ttcacactgt gctctttctg aaaaatgtag actcgctttt    13920
tttttttttt ttttgagat ggggtcttgc tctgtcgccc agactggagt gcagtggctc     13980
catctcagct cactacaacc tctgcctccc aggttcaagc gattctcctg tctcagcctc    14040
cccagtagct gggattacag gtgcaccctg ccatgcccgg ctaatttttt gtattttagt    14100
agagatgggg tttcaccatg ttgcccaggc tggtctcgaa ctcctgagct caggcaatcc    14160
acccgctttg gtctcccaaa gtgctaggat tacacgcatg agccaccgcg cccggcctag    14220
actcacatct tttatacact tactgcccaa ttcagttctt tatggtttat ttttgcttgt    14280
ttcattataa aaactagac agttgcataa attcaaccac ttacttgttg aatccattta     14340
gtcaatgcaa gctcaacatt ttcatattta tttttgcct  tatgcaatat tgttcaacat    14400
tttcataagt tgttggtcag cactatctct attaactttc aacagtttgc ccttctaagt    14460
cacaaatagt gatgctgctg caattatttt tcactaacat gcctcagatt tctgtagtga    14520
ttctacattt gatattattc acaatgtaaa atgcttctat ttattcattt cacttttacc    14580
cacaggatta ttttaagtt attttgtca ttttcacact tcaaccaaac ataaagacaa      14640
aaacatcaaa aatatgtaca tagtgttata cataggtgta tatttacaca catatatgca    14700
catatgttta tatgtattga aactacagaa gcacatgtca ccaataagag ctctgagaca    14760
cctttgacca cttacccta tcagatgaga tttgccaaat gagttttggg aacaaatttc     14820
ttttaactga atttctgagc tttgtggatt tagaaatgca actgaaagtt tgtggacatt    14880
```

-continued

```
tacgaggatc atagttttat tctccttaaa actcttcaat actttcccat tgtctttagt   14940
aaatccaaaa tcctaacacc actcacgagg cttttcaaca cctggcttct tgtgatttct   15000
ccaatctaac cttttaccct ccttcccctc agcctctctg ctttagtgaa ctttgttcta   15060 gtttttgaa gttcatcatc aattcaagct tttgtacatg ggatttccta aacctgaaat   15120
gtgcctccgg ttttgtccaa acagacacac aggctccact ctgccccctg gctcacacct   15180
gcttaacttg ttaagtcaca tctgtaactg tcactcttct ctggcaccct aaaggaattg   15240
agatcatcct attattctct gttctagaac tccacacttc tgaaatttct cattcctgtc   15300
taagctcttg tgtgtttggt ttttggccat cactttcact gctcttaaag ctcccccagc   15360
ggagtggaga ggtctgtttt cccgtgtttg gattcctaga ggcagcgcag gcctggcaca   15420
aggtcatcac taaggaagtg ttcacaggat gaaagcggtg cgtgctgttt aaggaaaggg   15480
taaagccttt aaatggtaaa gggttgagag aaggagcaaa gtgcctttgg ggtggaggct   15540
cccaggagga ggcggcgcgg gctgcggtgc tggacggatc ctcctccagc tcctgcctgg   15600
aggtctccag aacaggctgg aggcagggag ggggtcccaa aagccttggg atcagaggta   15660 gttttttccac ctggtccccc agaccccgt ccgcctcaga aagacagagg atgagcccct   15720
gggctgcgtg ttgtcggggt tgcgggtggg gccagatagt gtcttccccg gaggccgctt   15780
ctgtaaccgg atcgttcttg tccccccagc acgtttcttg gagcaggtta acatgagtg   15840 tcatttcttc aacgggacgg agcgggtgcg gttcctggac agatacttct atcaccaaga   15900
ggagtacgtg cgcttcgaca gcgacgtggg ggagtaccgg gcggtgacgg agctggggcg   15960
gcctgatgcc gagtactgga acagccagaa ggacctcctg gagcagaagc gggccgcggt   16020
ggacacctac tgcagacaca actacggggt tggtgagagc ttcacagtgc agcggcgagg   16080
tgagcgcggc gcggggcggg gcctgagtcc ctgtgagcgg agaatctgag tgtgtgtgtg   16140
tgtgtgtgtg tgtgtgtgtg tgtgtgtgtg tgtgagagag agagagagag agagagagag   16200
agagagcgcc atctgtgagc atttagaatc ctctctatcc tgagcaagga gttctgcggg   16260
cacaggtgtg tgtgtagagt gtggatttgt ccgtgtctgt gaggctgttg tgggagggga   16320
ggcaggaggg ggctgcttct tattcttgga gacttctgtg gggaggtgac aagggaggtg   16380
ggtgctgggg gctggagaga gaggcgacct tgattgtctc gggtccttag agatgcaagg   16440
aagggaaatg tatgggtgt gtggttgggg tgaaggttta ggggaggaga gctgaggggt   16500
aaggaaggtt tgggataatg tgaagaggcc agtttcagac tgtccctggc acacacctt   16560 catgtaatct ctgaaataaa agtgtgtgct gtttgtttgt aaaagcatta gattaacttc   16620 tagggggaatt gagtagacct ctgaggcacc tctgaagctt ctttaggtat aaatttcttg   16680
ctagtttttt gtttttcttag tgttatattt ttacatagtt gaaatgactg tgaaactaac   16740
tttttgaatt aaagtttgaa aacactgtta ctatttttatt ataatgctaa taatttcata   16800
gttacttttt aaatatataa tagttgtgac acaaattacc tcacttttctt tgtttttttt   16860 tttcttacac tttaagtttt agggtacatg tgcacaacgt gcaggtttgt tacatatgta   16920
tacatgtgcc atgttggtgt gctgcaccca ttaactcgtc atttaacatt aggtatatct   16980
cctaatgcta tccctcccca ccccccccacc ccacaacagg ccccagtgtg tgatgttccc   17040
cttcctgtgt ccatgtgttc tcactgttca attcccacct atgagtgaga acatgcggtg   17100
ttcggttttt tgtccttgcc atagtttgct gagaatgatg gtttccagct tcatccatgt   17160
ccctacaaag gacatgaact cattcttttt tgtggctgca tagtattcca tagtgtatat   17220
gtgccacatt ttcttaatcc agtctatcat tgttggacat ttgggttggt tccaagtctt   17280
```

```
tgctattgtg aatagtgccg caataaacat acatgtgcat atgtctttat agcagcatga    17340
tttataatcc ttgggttata tacccagtaa tgggatggct gggtcaaatg gtatttctag    17400
ttctagatcc ctgaggaatc gccacactga cttccacaat ggttgaacta gtttagagtc    17460
ccaccaacag ggtaaaagtg ttcctatttc tccacatcct ctccagcacc tgttgcttcc    17520
tgacttttta atgatcgcca ttctaactgg tgtgagatgg tatctcattg tggttttgat    17580
ttgcaattct ctgatggcca gtgatgatga gcatttttttc atgtgtcttt tggctgcata    17640
aatgtcttct tttgagaagt gtctgttcat gtcctttgcc cacttttttga tggggtatttt    17700 tgttttttttc ttgtaaatttt gtttgagttc attgcagatt ctggatatta gcccttttgtc    17760 atatgagtag attgcaaaaa ttttctccca ttctgtaggt tgcctcttca ctctgatggt    17820
agtttctttt gctgtgcaga agctctttag tttaattaga tcccatttgt ccattttggc    17880
ttttgttgcc attgcttttg gtgttttaga catgaagttc ttgcccatgc ctatgtcctg    17940
aatggtattg cctaggtttt cttctagggt ttttatggtt tcaggtctaa catttaagtc    18000
tttaatccat cttgaattaa ttttttgtata agcaaattac gtcactttcc ccattgatga    18060
cctttattat gacattcacc aatagttgaa aatgtatgtt tctggttaat ttttgattta    18120 tattttttg atttgtaatt attttgaatt attttgacct atttattggc cagttgtaat    18180
tactgctctg ctctacgaat tacctgttgt atttggtagg taatggacaa tgatctattg    18240
tctcttatct ttagggctta gtattttttct cagtgacttt gtgggtttgt tgtactgtaa    18300
gattattaac acttttattga tatttgattc agtattttct ccagtttgtg gtatgtatat    18360
tttgaaaatt cttttccatg ttaagaaattt gaacatttttt atttaataaa atatattgca    18420
aaatgttaat taatgattca caaactagct caagtctacc attttgtggt attgatgtct    18480
ccaggtttct ccttccttct taaaaaaaaaa tgtatttatt gagagtatgc tagtgtcagg    18540
gatttcccta ggcataagca ctccaagtaa tgagtcccag acactgcctt gatccaaatg    18600
tcattctgga aagaaaaatc attttacagt gataagccta ataatagtta tacttgtttt    18660
gcctgggaga tgcattgatc agctaaatgt aaatataaga actttcaaaa ctaaaatgac    18720
gttccttaat ctttctctct gctttaggaa tcatgctttc ttaggaactt aaagatttgg    18780
agaatcattt ctgtctgtcc caccttccca ggagcataac catttctgtg gtgttctaag    18840
gtgtgagtgc atgcagtag tattcctaaa aatccatatt cagtttcctc atgtgcccta    18900
ctccgtccct ttctctatcc acattgcttt aaatcatatt tttctctcaa ggtgtacaag    18960
gatgataaat aggtgccaag tggagaaccc aagtgtgacg agccctctca cagtagaatg    19020
gagtgagaag cttctgacc tcataaattg aaggctatcg taattcattc ttttatatat    19080
tttacttgca ttaatcctca tataacctca agaggtaaat taatataatt atcctccatt    19140
attggagaga aagttgagac acaaaagaat caaaaactct tccaggatca accagtaaaa    19200
ggcagacctt ggatttgaac caggcaacct ggctcagaag tcagttttaa ttaccacact    19260
ctgtactttc aaagatttgt aaacgctttg acaatgcatg tcaatttcaa gctatgaaga    19320
gccaaacata attttttcaca atatctctca atctaatgg gtccccacta taagattaa    19380 attccaggct gatgacactg tgaggccaca tggccagctg tgctggaggc ctgctcaagg    19440
ccagagccta ggtttacaga gaagcagaca aaaagctaaa caaggagact tactctgtct    19500
gcatgactta ttccctctac cttgttttct cctagtctat cctgaggtga ctgtgtatcc    19560
tgcaaagacc cagcccctgc agcaccacaa cctcctggtc tgctctgtga atggtttcta    19620
```

```
tccaggcagc attgaagtca ggtggttccg gaacggccag gaagagaaga ctggggtggt    19680
gtccacaggc ctgatccaga atggagactg gaccttccag accctggtga tgctggaaac    19740
agttcctcgg agtggagagg tttacacctg ccaagtggag cacccaagcc tgacgagccc    19800
tctcacagtg gaatggagtg agcagctttc tgacttcata aatttctcac ccaccaagac    19860
gcgaacttta ctaatccctg agtatcaggc ttctcctatc ccacatccta ttttcatttg    19920
ctccacgttc tcatctccat cagcacaggt cactgggggg tagccctgta atactttcta    19980
gaaacacctg taccccctgg ggaagcagtc atgcctgcca ggcaggagag gctgtccctc    20040
ttttgaacct ccccatgatg tcacaagtcg gggtcacctg ctgtctgtgg gctccaggcc    20100
ctgcctctgg gtctgagact gagtttctgg tactgttgct ctgagtcgtt tgttgtaatc    20160
tgagaagagg agaagtatag ggaccttcct gacatgaggg gagtccaatc tcagctccgc    20220
cttttattag atctgtcact ctaggcaact acttaacctc attgggtctc aggctttctg    20280
ttcatcagat gttgaagtcc tgtcttacat caaggctgta atatttgaat gagtttgatg    20340
actgaacctt gtaactgttc agtgtgattt gaaaaccttt ctcaagaaat ggtcagttat    20400
tttagttctt gcagagcagc cttctttctc attttcaaag ctctgaatct caaggtgtca    20460
attaaagagg ttccatttgg gataaaaatc actaaacctg gcttcctctc tcaggagcac    20520
ggtctgaatc tgcacagagc aagatgctga gtggagtcgg gggcttcgtg ctgggcctgc    20580
tcttccttgg ggccgggctg ttcatctact tcaggaatca gaaaggtgag gagcctttgg    20640
tagctggctg tctccatacg cttttctgga ggaggaacta tggctttgct gaagttggtt    20700
ctcagcatat gaatggccct ggataaagcc tctctactcc caaatgacct ccaatgttct    20760
gcaaatccag aaatcatcag tgcatggttg ctatgtcaaa gcataatagc ttgtggccta    20820
cagagataac agaaagatta acaggtatag gtgctttggt tgagatcgtg gagcaaatta    20880
aggaagagca actaaagcta atacaattac actggatcct gtgacagaca cttcacactt    20940
catgggtcac atggtctgtt tctgctcctc tctgccctgg ctggtgtggg ttgtggtgtc    21000
agagaactct caggtgggag atctggagct gggacattgt gttggaggac agatttgctt    21060
ccatatcctt taagtgtata tcttctcttt ttcctaggac actctggact tcagccaaca    21120
ggtaatacct tttcatcctc tttaagaaac agatttggag gccaggcgca gtggctcacg    21180
cctgtaatcc cagcactttg ggaggccgag gcgggcgaat catgaggtca ggagttcgag    21240
accagcctga ccaacgtggt gaaaccccgt ctctactaaa aatacaaaaa aaaatcagtc    21300
gggcgtggtg gtgtgcgcct gtaatcccag ctactcagga ggccaaggca ggagaatcgc    21360
tggaacccag gaggcagagg ttgcagtgag ccgagattgg ccactgcac tccagcctag    21420 gtgacagagt gagacccat ctcaaaaaaa caaaaaaag aaagaaagaa acagatttcc    21480
tttccctaga atgatggtag aggtaataag gcatgagaca gaagtaatag caaagacatt    21540
ggatccaaat ttctgatcag gcaatttaca ccagaactcc tcctctccac ttagaaaagg    21600
cctgtgctct gcaggagtat tgactcatgg agacttcaga acttgttttt cttcttcctg    21660
cagtgctctc atctgagtcc ttgaaagagg gcaaaataaa ctgttagtag agccaggtct    21720
gaaaacaaca ctttcttgcg tctctgcagg attcctgagc tgaagtgaag atgaccacat    21780
tcaaggaaga accttctgcc ccagctttgc aggatgaaac acttcccgc ttggctctca    21840 ttcttccaca agagagacct ttctccggac ctggttgcta ctggttcagc agctctgcag    21900
aaaatgtcct cccttgtggc tgcctcagct cgtacctttg gcctgaagtc ccagcattaa    21960
tggcagcccc tcatcttcca gttttgtgc tccccttac ctaatgcttc ctgcctccca    22020
```

```
tgcatctgta ctcctgctgt gccacaaaca cattacatta ttaaatgttt ctcaaacatg    22080
gagttaaaaa tcgtctggtc atttggcccc aaggacaaaa aataaaaaga aaagaaaaag    22140
tgaagattat ttcccgatag aataatggtt ttcatggata tgtcataagt atgtgagata    22200
gtgcatatgt taaataggtt gatttagaca ttttacacta caggcatata tcaaaacttc    22260
atgctgtatg acataaatgc acaattttta cttgtcaatt taaaagtaa acctaacgtt     22320 taaaaaggtg atgcataaaa actgagaaca gactataaga actgaaacaa acttggcaaa    22380
catgagatga taaaccagct agcaagtcaa tcagaactct ttctcaaccc cgtctacaat    22440
attgtgtgtc tataactgta aattagtata tagttttca ttcca                     22485
```

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      Gly-Ser Linker

<400> SEQUENCE: 4

Gly Gly Gly Gly Ser Gly Gly Gly Gly Ser Gly Gly Gly Gly Ser
 1               5                  10                  15

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
cattgagaca gagcgcctgg cacagaagca g                                      31

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
ggatgacgtg agtaaacctg aatctttgga gtacgc                                 36

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
ttcttcaacg ggacggagcg ggtg                                              24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer -continued

```
<400> SEQUENCE: 8
ctgcactgtg aagctctcac caac                                           24

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
ctccaagccc tctcccagag                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
atgtgcctta cagaggcccc                                                20

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Gly Leu Ser Pro Thr Val Trp Leu Ser Val
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Trp Leu Ser Leu Leu Val Pro Phe Val
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Ile Leu Ser Pro Phe Leu Pro Leu
1               5

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
                               Peptide

<400> SEQUENCE: 14

Gln Ala Gly Phe Phe Leu Leu Thr Arg Ile Leu Thr Ile Pro Gln Ser
1               5                   10                  15

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Arg Gly Leu Tyr Phe Pro Ala Gly Gly Ser Ser Ser Gly
1               5                   10

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Met Gln Trp Asn Ser Thr Thr Phe His Gln Thr Leu Gln Asp Pro Arg
1               5                   10                  15

Val Arg Gly Leu Tyr Phe Pro Ala Gly Gly
            20                  25

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

Thr Ser Leu Asn Phe Leu Gly Gly Thr Thr Val Cys Leu Gly Gln
1               5                   10                  15

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Ser Leu Leu Val Pro Phe Val Gln Trp Phe Val Gly Leu Ser Pro Thr
1               5                   10                  15

Val Trp Leu Ser Val
            20
```